(12) United States Patent
Soth et al.

(10) Patent No.: US 11,560,366 B2
(45) Date of Patent: Jan. 24, 2023

(54) BICYCLO[1.1.1]PENTANE INHIBITORS OF DUAL LEUCINE ZIPPER (DLK) KINASE FOR THE TREATMENT OF DISEASE

(71) Applicant: Board of Regents, The University of Texas System, Austin, TX (US)

(72) Inventors: Michael J. Soth, Sugar Land, TX (US); Kang Le, Sugar Land, TX (US); Philip Jones, Houston, TX (US); Jason Cross, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/075,400

(22) Filed: Oct. 20, 2020

(65) Prior Publication Data

US 2021/0115010 A1    Apr. 22, 2021

Related U.S. Application Data

(60) Provisional application No. 62/923,929, filed on Oct. 21, 2019.

(51) Int. Cl.
| | | |
|---|---|---|
| *C07D 401/04* | (2006.01) | |
| *A61K 31/4439* | (2006.01) | |
| *A61K 31/4545* | (2006.01) | |
| *C07D 401/14* | (2006.01) | |

(52) U.S. Cl.
CPC ........ *C07D 401/04* (2013.01); *A61K 31/4439* (2013.01); *A61K 31/4545* (2013.01); *C07D 401/14* (2013.01)

(58) Field of Classification Search
CPC ................ C07D 401/04; C07D 401/14; A61K 31/4439; A61K 31/4545
See application file for complete search history.

(56) References Cited

U.S. PATENT DOCUMENTS

| | | | |
|---|---|---|---|
| 7,163,924 B2 | 1/2007 | Burger | |
| 10,093,664 B2 | 10/2018 | Soth | |
| 10,428,057 B2 | 10/2019 | Soth | |
| 2005/0009764 A1 | 1/2005 | Burger | |
| 2009/0203705 A1 | 8/2009 | Biagetti | |
| 2011/0065727 A1 | 3/2011 | De Peretti | |
| 2012/0322795 A1 | 12/2012 | Berry | |
| 2015/0080367 A1 | 3/2015 | Cohen | |
| 2016/0002228 A1 | 1/2016 | Estrada | |
| 2016/0052940 A1 | 2/2016 | Estrada | |
| 2016/0257690 A1 | 9/2016 | Kinsella | |
| 2017/0081295 A1 | 3/2017 | Bunker | |
| 2018/0057507 A1 | 3/2018 | Soth | |
| 2019/0382396 A1 | 12/2019 | Jones | |
| 2022/0267311 A1* | 8/2022 | Soth | A61P 43/00 |

FOREIGN PATENT DOCUMENTS

| | | |
|---|---|---|
| CN | 104119340 | 12/2014 |
| WO | 2013174780 | 11/2013 |
| WO | 2014111496 | 7/2014 |
| WO | 2014177060 | 11/2014 |
| WO | 2014177524 | 11/2014 |
| WO | 2015091889 | 6/2015 |
| WO | 2015134710 | 9/2015 |
| WO | 2016142310 | 9/2016 |
| WO | 2016161160 | 10/2016 |
| WO | 2018044808 | 3/2018 |
| WO | 2018093577 | 5/2018 |
| WO | 2018107072 | 6/2018 |
| WO | 2019241244 | 12/2019 |

OTHER PUBLICATIONS

Siu; J. Med. Chem. 2018, 61, 18, 8078-8087. https://doi.org/10.1021/acs.jmedchem.8b00370 (Year: 2018).*
Berge, S. et al., "Pharmaceutical Salts", J Pharm Sci., 66(1):1-19, (1977).
International Application No. PCT/US2017/021784; International Search Report and Written Opinion of the International Searching Authority, dated Mar. 10, 2017; 12 pages.
International Application No. PCT/US2017/048941; International Search Report and Written Opinion of the International Searching Authority, dated Dec. 21, 2017; 10 pages.
International Application No. PCT/US2017/065385; International Preliminary Report on Patentability, dated Jun. 20, 2019; 8 pages.
International Application No. PCT/US2017/065385; International Search Report and Written Opinion of the International Searching Authority, dated Apr. 5, 2018; 12 pages.
International Application No. PCT/US2019/036545; International Search Report and Written Opinion of the International Searching Authority, dated Oct. 1, 2019; 12 pages.

(Continued)

*Primary Examiner* — Daniel R Carcanague
(74) *Attorney, Agent, or Firm* — Dennis A. Bennett; Lauren L. Stevens; Cynthia Hathaway

(57) ABSTRACT

Disclosed herein are compounds which inhibit the kinase activity of dual leucine zipper (DLK) kinase (MAP3K12), pharmaceutical compositions, and methods of treatment of DLK-mediated diseases, such as neurological diseases that result from traumatic injury to central nervous system and peripheral nervous system neurons (e.g. stroke, traumatic brain injury, spinal cord injury), or that result from a chronic neurodegenerative condition (e.g. Alzheimer's disease, frontotemporal dementia, Parkinson's disease, Huntington's disease, amyotrophic lateral sclerosis, spinocerebellar ataxia, progressive supranuclear palsy, Lewy body disease, Kennedy's disease, and other related conditions), from neuropathies resulting from neurological damage (chemotherapy-induced peripheral neuropathy, diabetic neuropathy, and related conditions) and from cognitive disorders caused by pharmacological intervention (e.g. chemotherapy induced cognitive disorder, also known as chemobrain).

24 Claims, 1 Drawing Sheet

Specification includes a Sequence Listing.

(56) References Cited

OTHER PUBLICATIONS

Measom, N. et al., "Investigation of a Bicyclo[1.1.1]pentane as a Phenyl Replacement within an LpPLA2 Inhibitor", ACS Med Chem Lett., 8(1):43-8, (2017).
Oetjen, E. et al., "Dual Leucine Zipper Kinase (MAP3K12) Modulators: A Patent Review (2010-2015)", Expert Opin Ther Pat., 26(5):607-16, (2016).
Patel, S. et al., "Selective Inhibitors of Dual Leucine Zipper Kinase (DLK, MAP3K12) with Activity in a Model of Alzheimer's Disease", J Med Chem., 60(19):8083-102, (2017).
Patel, S. et al., "Discovery of Dual Leucine Zipper Kinase (DLK, MAP3K12) Inhibitors with Activity in Neurodegeneration Models", J Med Chem., 58(1):401-18, (2015).
Patel, S. et al., . "Scaffold-Hopping and Structure-Based Discovery of Potent, Selective and Brain Penetrant N-(1H-Pyrazol-3-yl)pyridin-2-amine Inhibitors of Dual Leucine Zipper Kinase (DLK, MAP3K12)", J Med Chem., 58(20):8182-99, (2015).
PubChem CID: 122510487, Create Date: Dec. 8, 2016; 10 pages.
U.S. Appl. No. 15/688,554; Advisory Action, dated Nov. 25, 2019; 5 pages.
U.S. Appl. No. 15/688,554; Examiner Interview Summary Record, dated Dec. 4, 2019; 1 page.
U.S. Appl. No. 15/688,554; Examiner-Interview Summary Record, dated Apr. 29, 2020; 2 pages.
U.S. Appl. No. 15/688,554; Final Office Action, dated Jun. 5, 2019; 14 pages.
U.S. Appl. No. 15/688,554; Non-Final Office Action, dated Apr. 29, 2020; 12 pages.
U.S. Appl. No. 15/688,554; Non-Final Office Action, dated Sep. 28, 2018; 31 pages.
U.S. Appl. No. 15/836,442; Examiner-Initiated Interview Summary, dated May 29, 2018; 1 page.
U.S. Appl. No. 15/836,442; Notice of Allowance, dated Jun. 5, 2018; 10 pages.
U.S. Appl. No. 16/121,198; Non-Final Office Action, dated Jan. 29, 2019; 15 pages.
U.S. Appl. No. 16/121,198; Notice of Allowance, dated May 16, 2019, 7 pages.
U.S. Appl. No. 16/437,785; Non-Final Office Action, dated May 20, 2020; 19 pages.
U.S. Appl. No. 16/541,946; Application as filed, dated Aug. 15, 2019; 118 pages.
U.S. Appl. No. 17/121,072; Application as filed, dated Dec. 14, 2020; 118 pages.

* cited by examiner (a)

(b)

(c)

BICYCLO[1.1.1]PENTANE INHIBITORS OF DUAL LEUCINE ZIPPER (DLK) KINASE FOR THE TREATMENT OF DISEASE

CROSS REFERENCE TO RELATED APPLICATIONS

This application claims priority to, and the benefit of, U.S. Application No. 62/923,929, filed Oct. 21, 2019, the entirety of which is incorporated by reference herein.

INCORPORATION OF SEQUENCE LISTING

The sequence listing that is contained in the file named "MDA0050-201-US_ST25," which is 4.00 kilobytes as measured in Microsoft Windows operating system and was created on Jun. 24, 2022, is filed electronically herewith and incorporated herein by reference.

SUMMARY OF THE DISCLOSURE

Disclosed herein are new substituted bicyclo[1.1.1]pentane compounds and compositions and their application as pharmaceuticals for the treatment of disease. Some of these compounds surprisingly show improved metabolic and pharmacokinetic properties compared to related analogs reported in a previous patent application (WIPO publication WO2018107072A1). Methods of inhibition of the kinase activity of dual leucine zipper in a human or animal subject are also provided for the treatment of diseases such as neurological diseases that result from traumatic injury to central nervous system and peripheral nervous system neurons, neurodegenerative conditions, neuropathies resulting from neurological damage, and treatment of pain and cognitive disorders caused by pharmacological intervention.

Dual leucine zipper kinase (DLK) is a member of the mixed lineage kinase (MLK) family that is required for stress-induced neuronal activation of c-Jun N-terminal kinases (JNK). In turn, JNK is implicated in pathways important to cellular regulation including apoptosis and cell proliferation. JNK has been implicated in both naturally occurring cell death and pathological death of neurons.

Novel compounds and pharmaceutical compositions, which have been found to inhibit the kinase activity of DLK, have been discovered, together with methods of synthesizing and using the compounds including methods for the treatment of DLK-mediated diseases in a patient by administering the compounds.

BRIEF DESCRIPTION OF THE SEQUENCES

SEQ ID NO:1—Sequence of NFkB binding site.
SEQ ID NO:2—Sequence of C-terminal hexahistidine tag.

DETAILED DESCRIPTION

Figure 1A:
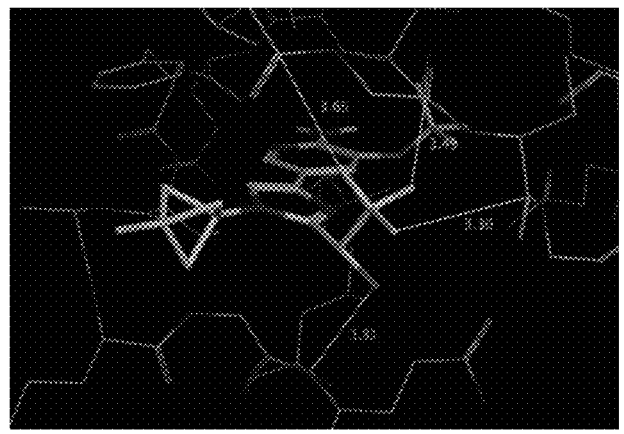
FIG. 1A shows a crystal structure of compound 1a bound to DLK.
Figure 1B:
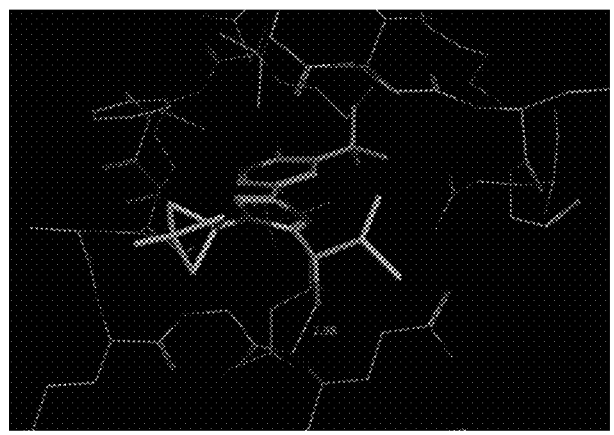
FIG. 1B shows a crystal structure of compound 13 bound to DLK.
Figure 1C:
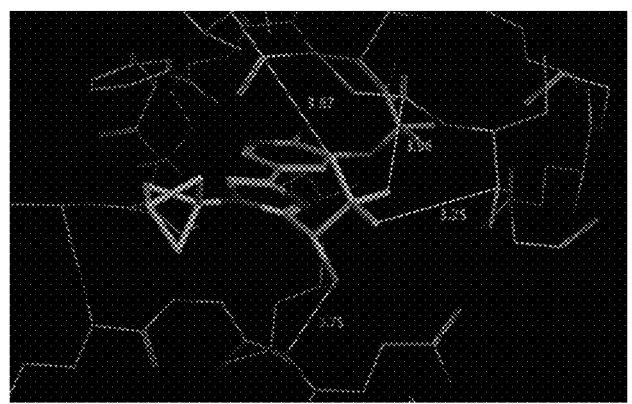
FIG. 1C shows a crystal structure of compound 4b bound to DLK.

Provided herein is Embodiment 1, a compound of structural Formula (I)

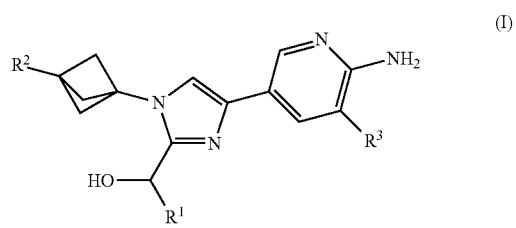

or a salt thereof wherein:
$R^1$ is chosen from alkyl and cycloalkyl, either of which is optionally substituted with one or more $R^4$.
$R^2$ is chosen from fluoro and $NR^{5a}R^{5b}$;
$R^3$ is chosen from trifluoromethyl and trifluoromethoxy;
$R^4$ is halo;
$R^{5a}$ and $R^{5b}$ combine to form alkylene which, together to the intervening nitrogen, forms a monocyclic heterocycloalkyl which is optionally substituted with one or more $R^6$; and
each $R^6$ is independently chosen from cyano, halo, and hydroxyl.

Also provided herein is Embodiment 1a, a compound of structural Formula (I')

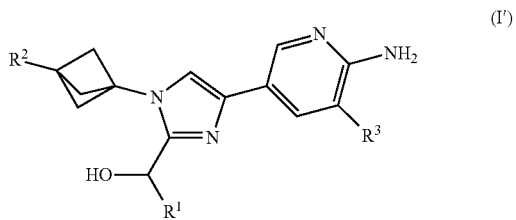

or a salt thereof wherein:
$R^1$ is chosen from alkyl and cycloalkyl, either of which is optionally substituted with one or more $R^4$.
$R^2$ is chosen from fluoro and $NR^{5a}R^{5b}$;
$R^3$ is chosen from trifluoromethyl and trifluoromethoxy;
$R^4$ is halo;
$R^{5a}$ and $R^{5b}$ combine to form alkylene which, together to the intervening nitrogen, forms a monocyclic heterocycloalkyl which is optionally substituted with one or more $R^6$; and
each $R^6$ is independently chosen from cyano, halo, and hydroxyl;
provided that $R^2$ is not a morpholine group.

Compounds disclosed herein possess useful DLK inhibiting activity, and may be used in the treatment or prophylaxis of a disease or condition in which DLK plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting DLK. Other embodiments provide methods for treating a DLK-mediated disorder in a patient in need of such treatment, comprising administering to said patient a therapeutically effective amount of a compound or composition as disclosed herein. Also provided is the use of compounds disclosed herein for use in the manufacture of a medicament for the treatment of a disease or condition ameliorated by the inhibition of DLK.

In certain embodiments, $R^{5a}$ and $R^{5b}$ combine to form alkylene which, together to the intervening nitrogen, forms a 4-7 membered monocyclic heterocycloalkyl which is optionally substituted with one or more $R^6$. In certain embodiments, $R^{5a}$ and $R^{5b}$ combine to form alkylene which, together to the intervening nitrogen, forms a 5-7 membered monocyclic heterocycloalkyl which is optionally substituted with one or more $R^6$. In certain embodiments, $R^{5a}$ and $R^{5b}$ combine to form alkylene which, together to the intervening nitrogen, forms a 4-6 membered monocyclic heterocycloalkyl which is optionally substituted with one or more $R^6$. In certain embodiments, $R^{5a}$ and $R^{5b}$ combine to form alkylene which, together to the intervening nitrogen, forms a 5-6 membered monocyclic heterocycloalkyl which is optionally substituted with one or more $R^6$.

In certain embodiments, the monocyclic heterocycloalkyl formed by $R^{5a}$, $R^{5b}$ and the intervening nitrogen comprise exactly one —$CF_2$—. In certain embodiments, the monocyclic heterocycloalkyl formed by $R^{5a}$, $R^{5b}$ and the intervening nitrogen is chosen from 3,3-difluoropyrrolidin-1-yl, 3,3-difluoropiperidin-1-yl, and 4,4-difluoropiperidin-1-yl. In certain embodiments, the monocyclic heterocycloalkyl formed by $R^{5a}$, $R^{5b}$ and the intervening nitrogen is chosen from 3,3-difluoropiperidin-1-yl and 4,4-difluoropiperidin-1-yl. In certain embodiments, the monocyclic heterocycloalkyl formed by $R^{5a}$, $R^{5b}$ and the intervening nitrogen is 4,4-difluoropiperidin-1-yl.

In certain embodiments, each $R^6$ is chosen from cyano and halo. In certain embodiments, each $R^6$ is halo. In certain embodiments, each $R^6$ is fluoro.

Also provided herein is Embodiment 2, the compound of Embodiment 1 or 1a having structural Formula (II):

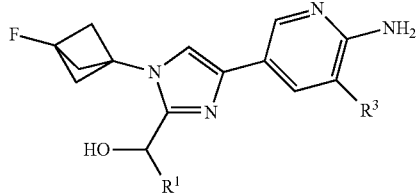

(II)

or a salt thereof wherein:
$R^1$ is chosen from alkyl and cycloalkyl, either of which is optionally substituted with one or more $R^4$.
$R^3$ is chosen from trifluoromethyl and trifluoromethoxy; and
$R^4$ is halo.

Also provided herein is Embodiment 3, the compound of Embodiment 2 having structural Formula (IIa):

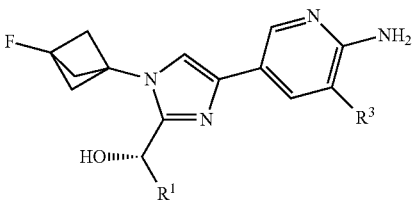

(IIa)

or a salt thereof wherein:
$R^1$ is chosen from alkyl and cycloalkyl, either of which is optionally substituted with one or more $R^4$.
$R^3$ is chosen from trifluoromethyl and trifluoromethoxy; and
$R^4$ is halo.

Also provided herein is Embodiment 4, the compound of Embodiment 2 having structural Formula (IIb):

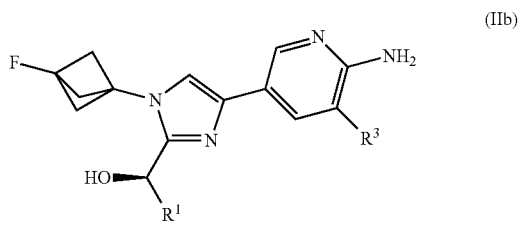

(IIb)

or a salt thereof wherein:
$R^1$ is chosen from alkyl and cycloalkyl, either of which is optionally substituted with one or more $R^4$.
$R^3$ is chosen from trifluoromethyl and trifluoromethoxy; and
$R^4$ is halo.

Also provided herein is Embodiment 5, the compound of Embodiment 1 having structural Formula (III):

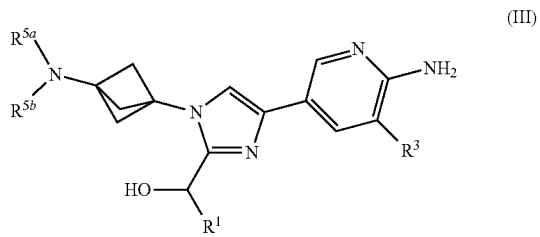

(III)

or a salt thereof wherein:
$R^1$ is chosen from alkyl and cycloalkyl, either of which is optionally substituted with one or more $R^4$.
$R^3$ is chosen from trifluoromethyl and trifluoromethoxy;
$R^4$ is halo;
$R^{5a}$ and $R^{5b}$ combine to form alkylene which, together to the intervening nitrogen, forms a monocyclic heterocycloalkyl which is optionally substituted with one or more $R^6$; and
each $R^6$ is independently chosen from cyano, halo, and hydroxyl.

Also provided herein is Embodiment 6a, the compound of Embodiment 1a having structural Formula (III'):

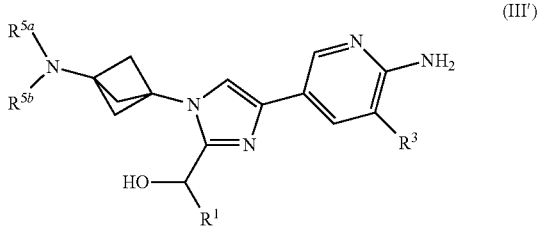

(III')

or a salt thereof wherein:
$R^1$ is chosen from alkyl and cycloalkyl, either of which is optionally substituted with one or more $R^4$.
$R^3$ is chosen from trifluoromethyl and trifluoromethoxy;

R⁴ is halo;

R⁵ᵃ and R⁵ᵇ combine to form alkylene which, together to the intervening nitrogen, forms a monocyclic heterocycloalkyl which is optionally substituted with one or more R⁶; and each R⁶ is independently chosen from cyano, halo, and hydroxyl, provided R⁵ᵃ and R⁵ᵇ when combined do not form a morpholine group.

Also provided herein is Embodiment 7, the compound of Embodiment 5 having structural Formula (IIIa):

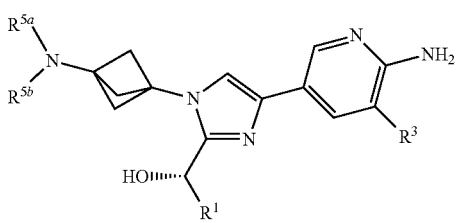

(IIIa)

or a salt thereof wherein:

R¹ is chosen from alkyl and cycloalkyl, either of which is optionally substituted with one or more R⁴.

R³ is chosen from trifluoromethyl and trifluoromethoxy;

R⁴ is halo;

R⁵ᵃ and R⁵ᵇ combine to form alkylene which, together to the intervening nitrogen, forms a monocyclic heterocycloalkyl which is optionally substituted with one or more R⁶; and each R⁶ is independently chosen from cyano, halo, and hydroxyl.

Also provided herein is Embodiment 8a, the compound of Embodiment 6a having structural Formula (IIIa):

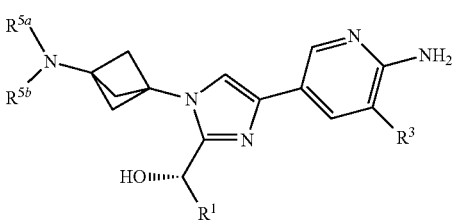

(IIIa′)

or a salt thereof wherein:

R¹ is chosen from alkyl and cycloalkyl, either of which is optionally substituted with one or more R⁴.

R³ is chosen from trifluoromethyl and trifluoromethoxy;

R⁴ is halo;

R⁵ᵃ and R⁵ᵇ combine to form alkylene which, together to the intervening nitrogen, forms a monocyclic heterocycloalkyl which is optionally substituted with one or more R⁶; and each R⁶ is independently chosen from cyano, halo, and hydroxyl, provided R⁵ᵃ and R⁵ᵇ when combined do not form a morpholine group.

Also provided herein is Embodiment 9, the compound of Embodiment 5 having structural Formula (IIIb):

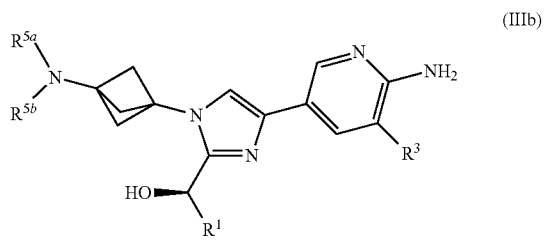

(IIIb)

or a salt thereof wherein:

R¹ is chosen from alkyl and cycloalkyl, either of which is optionally substituted with one or more R⁴.

R³ is chosen from trifluoromethyl and trifluoromethoxy;

R⁴ is halo;

R⁵ᵃ and R⁵ᵇ combine to form alkylene which, together to the intervening nitrogen, forms a monocyclic heterocycloalkyl which is optionally substituted with one or more R⁶; and each R⁶ is independently chosen from cyano, halo, and hydroxyl.

Also provided herein is Embodiment 10a, the compound of Embodiment 6a having structural Formula (IIIb′):

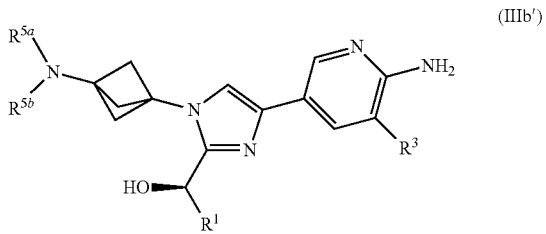

(IIIb′)

or a salt thereof wherein:

R¹ is chosen from alkyl and cycloalkyl, either of which is optionally substituted with one or more R⁴.

R³ is chosen from trifluoromethyl and trifluoromethoxy;

R⁴ is halo;

R⁵ᵃ and R⁵ᵇ combine to form alkylene which, together to the intervening nitrogen, forms a monocyclic heterocycloalkyl which is optionally substituted with one or more R⁶; and each R⁶ is independently chosen from cyano, halo, and hydroxyl, provided R⁵ᵃ and R⁵ᵇ when combined do not form a morpholine group.

Embodiment 11: the compound of any one of Embodiments 5-10a wherein R⁵ᵃ and R⁵ᵇ combine to form alkylene which, together to the intervening nitrogen, forms a 4-7 membered monocyclic heterocycloalkyl which is optionally substituted with one or more R⁶.

Embodiment 12: the compound of any one of Embodiments 5-10a wherein R⁵ᵃ and R⁵ᵇ combine to form alkylene which, together to the intervening nitrogen, forms a 5-7 membered monocyclic heterocycloalkyl which is optionally substituted with one or more R⁶.

Embodiment 13: the compound of any one of Embodiments 5-10a wherein R⁵ᵃ and R⁵ᵇ combine to form alkylene which, together to the intervening nitrogen, forms a 4-6 membered monocyclic heterocycloalkyl which is optionally substituted with one or more R⁶.

Embodiment 14: the compound of any one of Embodiments 5-10a wherein R⁵ᵃ and R⁵ᵇ combine to form alkylene which, together to the intervening nitrogen, forms a 5-6 membered monocyclic heterocycloalkyl which is optionally substituted with one or more $R^6$.

Embodiment 15: the compound of any one of Embodiments 5-14 wherein each $R^6$ is halo.

Embodiment 16: the compound of Embodiment 15 wherein each $R^6$ is fluoro.

Embodiment 17: the compound of Embodiment 16 wherein the monocyclic heterocycloalkyl formed by $R^{5a}$, $R^{5b}$ and the intervening nitrogen comprise one or two —$CF_2$—.

Embodiment 18: the compound of Embodiment 17 wherein the monocyclic heterocycloalkyl formed by $R^{5a}$, $R^{5b}$ and the intervening nitrogen comprise exactly one —$CF_2$—.

Embodiment 19: the compound of Embodiment 18 wherein the monocyclic heterocycloalkyl formed by $R^{5a}$, $R^{5b}$ and the intervening nitrogen is chosen from 3,3-difluoropyrrolidin-1-yl, 3,3-difluoropiperidin-1-yl, and 4,4-difluoropiperidin-1-yl.

Embodiment 20: the compound of Embodiment 18 wherein the monocyclic heterocycloalkyl formed by $R^{5a}$, $R^{5b}$ and the intervening nitrogen is chosen from 3,3-difluoropiperidin-1-yl and 4,4-difluoropiperidin-1-yl.

Embodiment 21: the compound of Embodiment 20 wherein the monocyclic heterocycloalkyl formed by $R^{5a}$, $R^{5b}$ and the intervening nitrogen is 4,4-difluoropiperidin-1-yl.

Embodiment 22: the compound of Embodiment 18 wherein the monocyclic heterocycloalkyl formed by $R^{5a}$, $R^{5b}$ and the intervening nitrogen is chosen from:

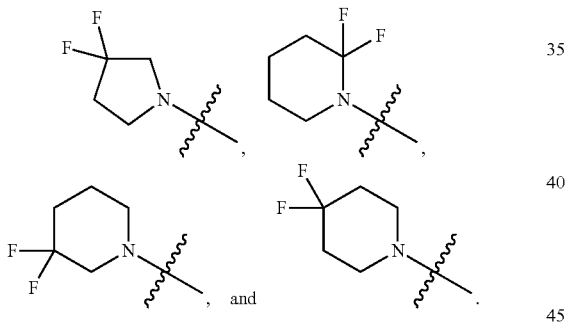

Embodiment 23: the compound of Embodiment 22 wherein the heterocycloalkyl formed by $R^{5a}$, $R^{5b}$ and the intervening nitrogen is

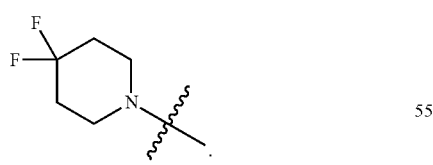

Embodiment 24: the compound of any one of Embodiments 1-23 wherein $R^1$ is chosen from $C_{1-6}$alkyl and $C_{3-7}$cycloalkyl, either of which is optionally substituted with one, two, or three $R^4$.

Embodiment 25: the compound of any one of Embodiments 1-24 wherein $R^4$ is fluoro.

Embodiment 26: the compound of either one of Embodiments 24 and 25 wherein $R^1$ is chosen from isopropyl, trifluoromethyl, and cyclopropyl.

Embodiment 27: the compound of Embodiment 1 or 1a, chosen from:

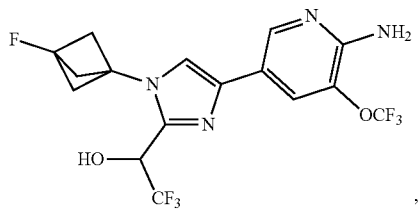

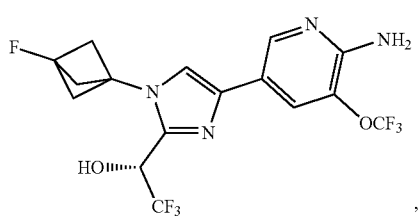

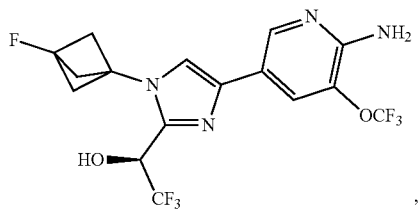

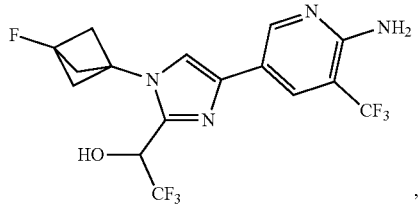

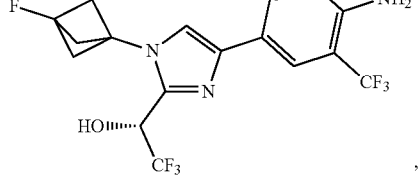

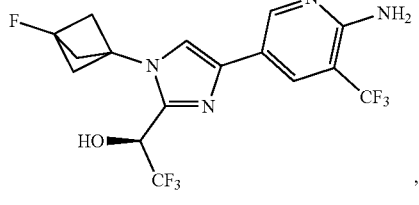

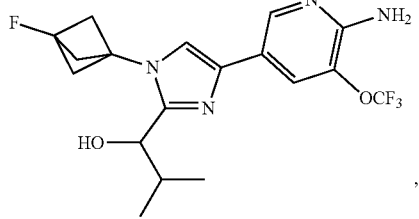

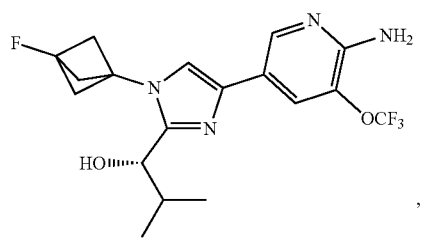
,
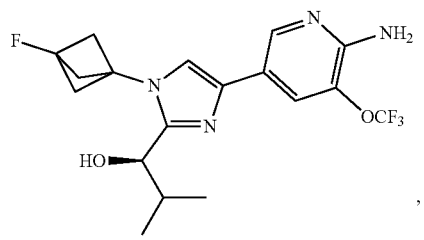
,
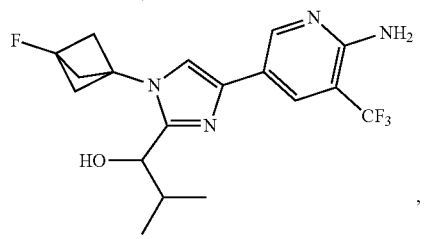
,
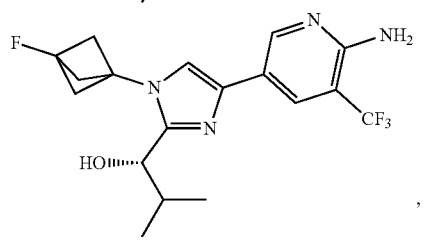
,
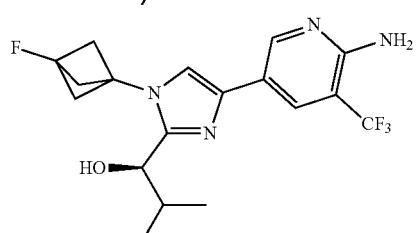
,
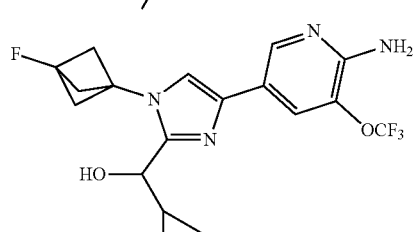
,
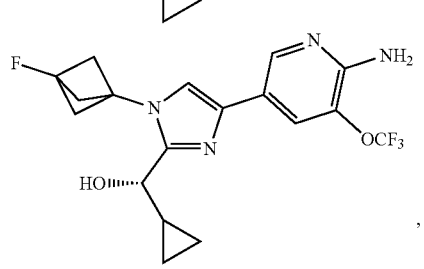
,
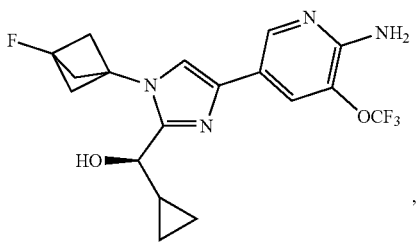
,
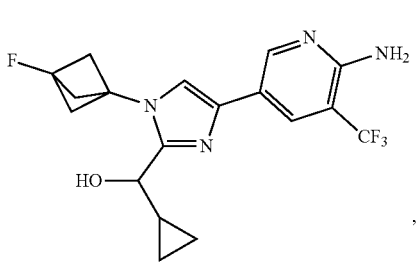
,
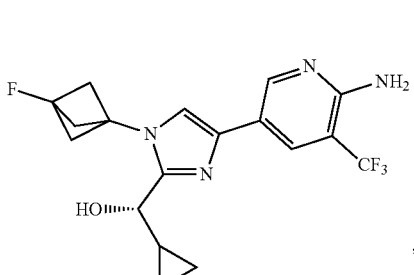
,
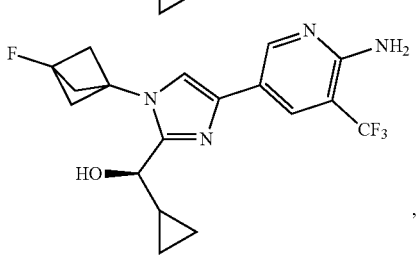
,
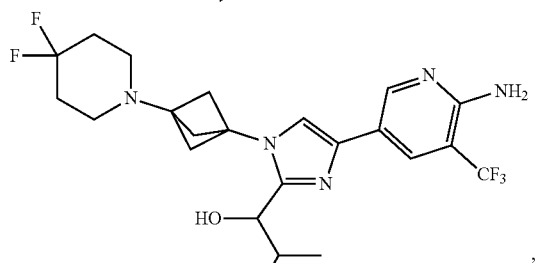
,
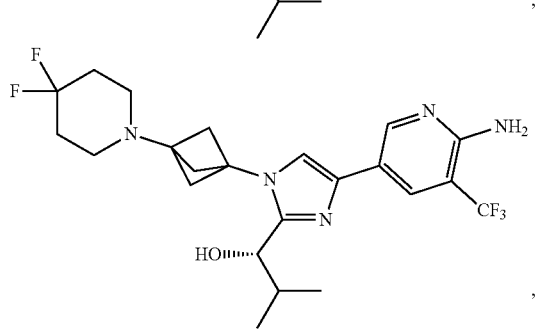
,

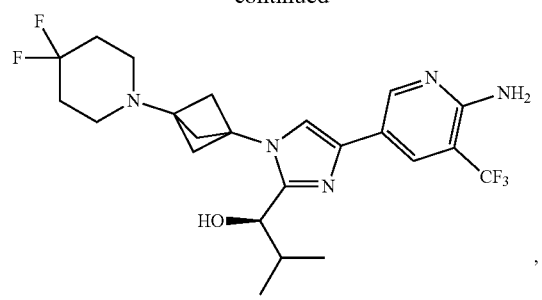,
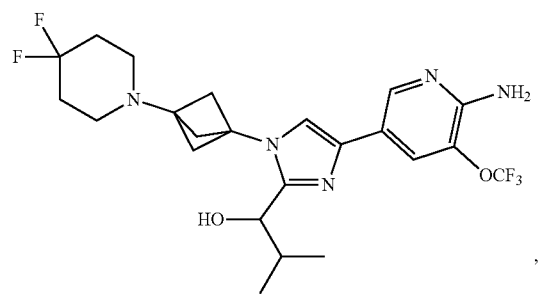,
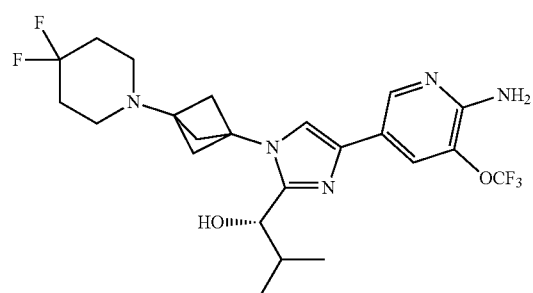,
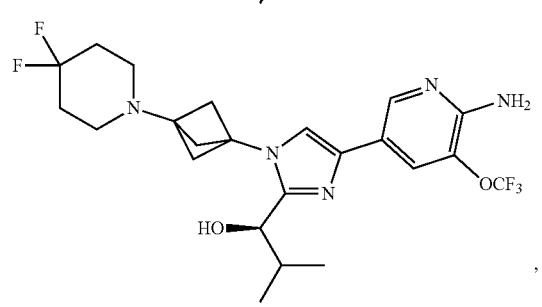,
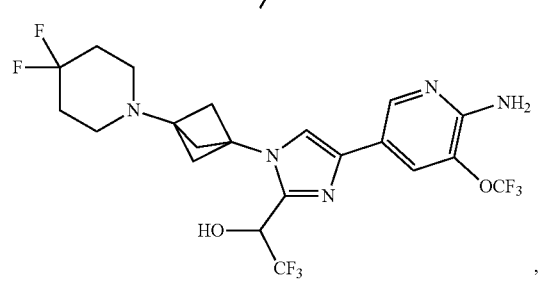,
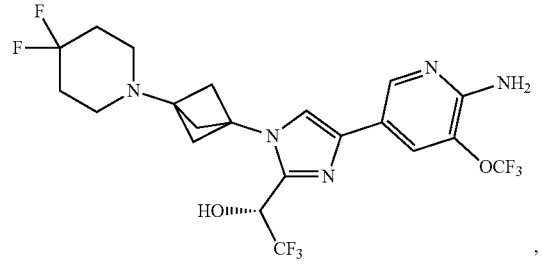,
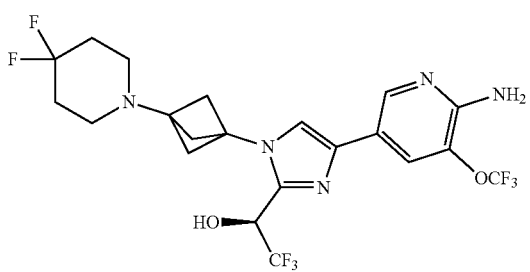,
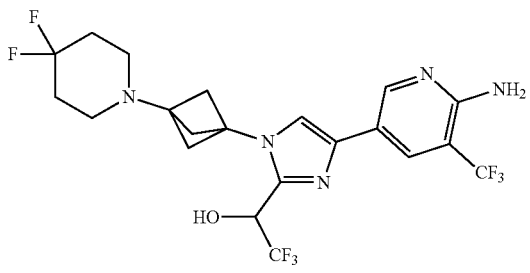,
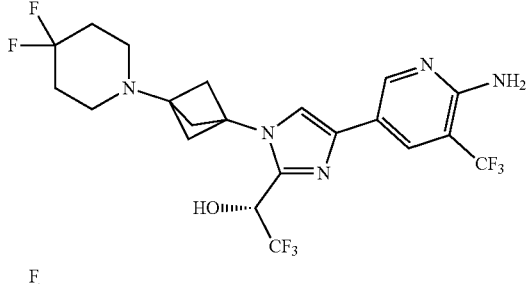,
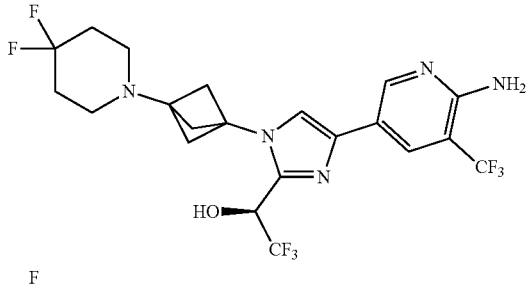,
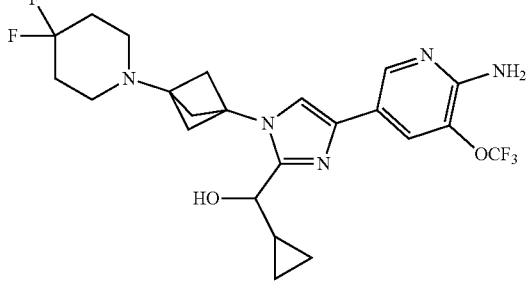,
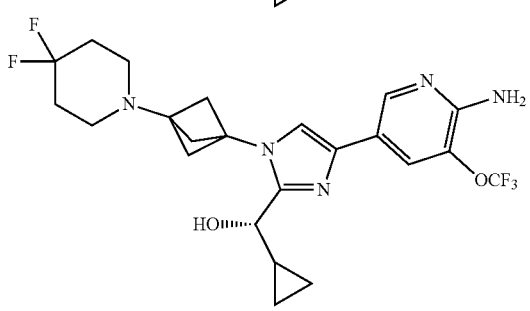,

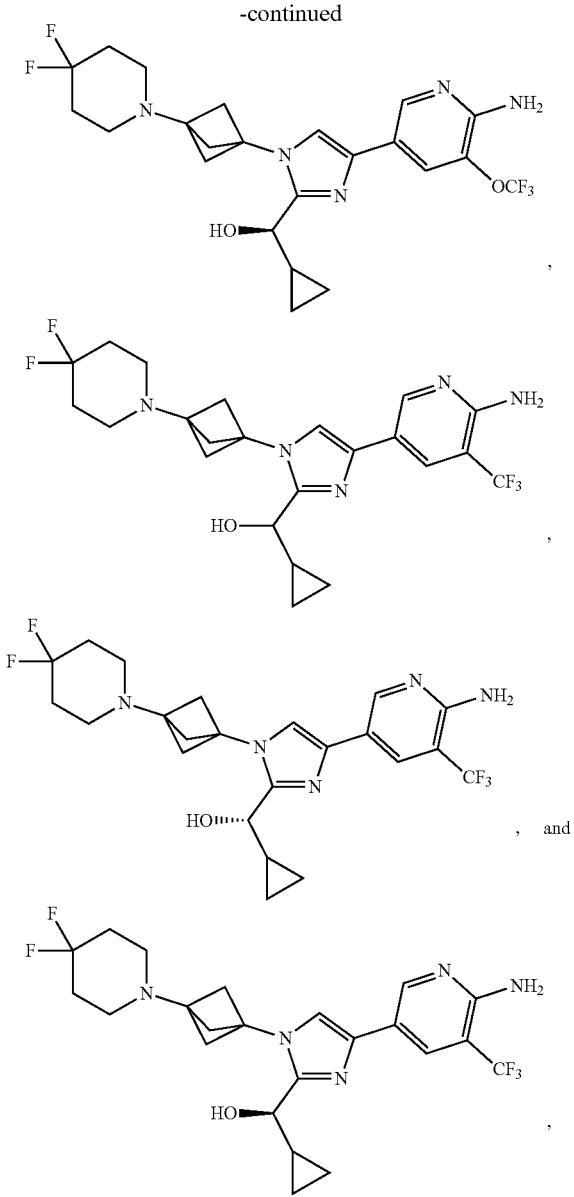

or a salt thereof.

In some embodiments, $R^1$ is alkyl optionally substituted with one or more $R^4$.

In come embodiments $R^1$ is chosen from $C_{1-6}$alkyl and $C_{3-7}$cycloalkyl, either of which is optionally substituted with one or more $R^4$. In come embodiments $R^1$ is $C_{1-6}$alkyl optionally substituted with one or more $R^4$. In come embodiments $R^1$ is $C_{3-7}$cycloalkyl optionally substituted with one or more $R^4$.

In come embodiments $R^1$ is $C_1$alkyl optionally substituted with one or more $R^4$. In come embodiments $R^1$ is $C_2$alkyl optionally substituted with one or more $R^4$. In come embodiments $R^1$ is $C_3$alkyl optionally substituted with one or more $R^4$. In come embodiments $R^1$ is $C_4$alkyl optionally substituted with one or more $R^4$. In come embodiments $R^1$ is $C_5$alkyl optionally substituted with one or more $R^4$. In come embodiments $R^1$ is $C_6$alkyl optionally substituted with one or more $R^4$.

In some embodiments, $R^1$ is methyl optionally substituted with one or more $R^4$. In some embodiments, $R^1$ is ethyl optionally substituted with one or more $R^4$. In some embodiments, $R^1$ is propyl optionally substituted with one or more $R^4$. In some embodiments, $R^1$ is n-propyl optionally substituted with one or more $R^4$. In some embodiments, $R^1$ is isopropyl optionally substituted with one or more $R^4$. In some embodiments, $R^1$ is butyl optionally substituted with one or more $R^4$. In some embodiments, $R^1$ is n-butyl optionally substituted with one or more $R^4$. In some embodiments, $R^1$ is isobutyl optionally substituted with one or more $R^4$. In some embodiments, $R^1$ is sec-butyl optionally substituted with one or more $R^4$. In some embodiments, $R^1$ is tert-butyl optionally substituted with one or more $R^4$. In some embodiments, $R^1$ is pentyl optionally substituted with one or more $R^4$. In some embodiments, $R^1$ is hexyl optionally substituted with one or more $R^4$.

In some embodiments, $R^1$ is unsubstituted alkyl. In some embodiments, $R^1$ is alkyl optionally substituted with one $R^4$. In some embodiments, $R^1$ is alkyl optionally substituted with two $R^4$. In some embodiments, $R^1$ is alkyl optionally substituted with three $R^4$. In some embodiments, $R^1$ is alkyl optionally substituted with four $R^4$. In some embodiments, $R^1$ is alkyl optionally substituted with five $R^4$. In some embodiments, $R^1$ is alkyl optionally substituted with six $R^4$.

In some embodiments, $R^1$ is cycloalkyl optionally substituted with one or more $R^4$.

In come embodiments $R^1$ is $C_3$cycloalkyl optionally substituted with one or more $R^4$. In come embodiments $R^1$ is $C_4$cycloalkyl optionally substituted with one or more $R^4$. In come embodiments $R^1$ is $C_5$cycloalkyl optionally substituted with one or more $R^4$. In come embodiments $R^1$ is $C_6$cycloalkyl optionally substituted with one or more $R^4$. In come embodiments $R^1$ is $C_7$cycloalkyl optionally substituted with one or more $R^4$.

In some embodiments, $R^1$ is cyclopropyl, cyclobutyl, cyclopentyl, cyclohexyl, cycloheptyl, cyclooctyl, cyclononyl, or cyclodecyl, each optionally substituted with one or more $R^4$.

In some embodiments, $R^1$ is cyclopropyl, optionally substituted with one or more $R^4$. In some embodiments, $R^1$ is cyclobutyl optionally substituted with one or more $R^4$. In some embodiments, $R^1$ is cyclopentyl, optionally substituted with one or more $R^4$. In some embodiments, $R^1$ is cyclohexyl optionally substituted with one or more $R^4$. In some embodiments, $R^1$ is cycloheptyl optionally substituted with one or more $R^4$. In some embodiments, $R^1$ is cyclooctyl optionally substituted with one or more $R^4$. In some embodiments, $R^1$ is cyclononyl optionally substituted with one or more $R^4$. In some embodiments, $R^1$ is cyclodecyl optionally substituted with one or more $R^4$.

In some embodiments, $R^1$ is unsubstituted cycloalkyl. In some embodiments, $R^1$ is cycloalkyl optionally substituted with one $R^4$. In some embodiments, $R^1$ is cycloalkyl optionally substituted with two $R^4$. In some embodiments, $R^1$ is cycloalkyl optionally substituted with three $R^4$. In some embodiments, $R^1$ is cycloalkyl optionally substituted with four $R^4$. In some embodiments, $R^1$ is cycloalkyl optionally substituted with five $R^4$. In some embodiments, $R^1$ is cycloalkyl optionally substituted with six $R^4$.

In some embodiments, $R^2$ is fluoro. In some embodiments, $R^2$ is $NR^{5a}R^{5b}$.

In some embodiments, the monocyclic heterocycloalkyl formed by $R^{5a}$, $R^{5b}$ is a 4-7 membered heterocycloalkyl. In some embodiments, the monocyclic heterocycloalkyl formed by $R^{5a}$, $R^{5b}$ is a 4-6 membered heterocycloalkyl. In some embodiments, the monocyclic heterocycloalkyl formed by $R^{5a}$, $R^{5b}$ is a 5-6 membered heterocycloalkyl. In some embodiments, the monocyclic heterocycloalkyl formed by $R^{5a}$, $R^{5b}$ is a 5-7 membered heterocycloalkyl.

In some embodiments, the monocyclic heterocycloalkyl formed by $R^{5a}$, $R^{5b}$ is a 4-membered heterocycloalkyl. In some embodiments, the monocyclic heterocycloalkyl formed by $R^{5a}$, $R^{5b}$ is a 5-membered heterocycloalkyl. In some embodiments, the monocyclic heterocycloalkyl formed by $R^{5a}$, $R^{5b}$ is a 6-membered heterocycloalkyl. In some embodiments, the monocyclic heterocycloalkyl formed by $R^{5a}$, $R^{5b}$ is a 7-membered heterocycloalkyl.

In some embodiments, the monocyclic heterocycloalkyl formed by $R^{5a}$, $R^{5b}$ is unsubstituted. In some embodiments, the monocyclic heterocycloalkyl formed by $R^{5a}$, $R^{5b}$ is substituted with one $R^6$. In some embodiments, the monocyclic heterocycloalkyl formed by Rsa, $R^{5b}$ is substituted with two $R^6$. In some embodiments, the monocyclic heterocycloalkyl formed by $R^{5a}$, $R^{5b}$ is substituted with three $R^6$. In some embodiments, the monocyclic heterocycloalkyl formed by $R^{5a}$, $R^{5b}$ is substituted with four $R^6$.

In some embodiments, the monocyclic heterocycloalkyl formed by $R^{5a}$, $R^{5b}$ is

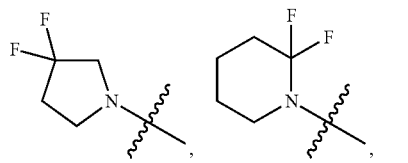

,

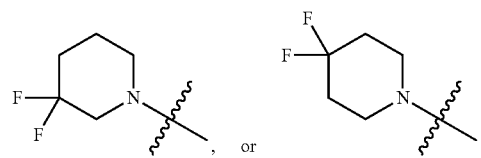

, or

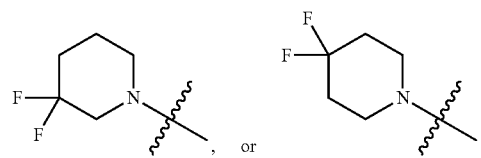

.

In some embodiments, the monocyclic heterocycloalkyl formed by $R^{5a}$, $R^{5b}$ is

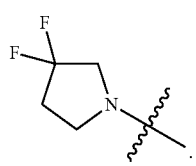

.

In some embodiments, the monocyclic heterocycloalkyl formed by $R^{5a}$, $R^{5b}$ is

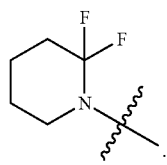 [SMILES: *N1CCCCC1(F)F]

.

In some embodiments, the monocyclic heterocycloalkyl formed by $R^{5a}$, $R^{5b}$ is

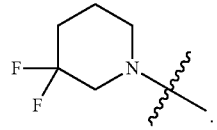

.

In some embodiments, the monocyclic heterocycloalkyl formed by $R^{5a}$, $R^{5b}$ is

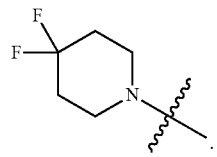

.

In some embodiments, $R^6$ is cyano. In some embodiments, $R^6$ is halo. In some embodiments, $R^6$ is hydroxyl.

In some embodiments, $R^6$ is F. In some embodiments, $R^6$ is $C_1$. In some embodiments, $R^6$ is Br. In some embodiments, $R^6$ is I.

In some embodiments, the salt of a compound of Formula (I) is a pharmaceutically acceptable salt. In some embodiments, the salt of a compound of Formula (II) is a pharmaceutically acceptable salt. In some embodiments, the salt of a compound of Formula (IIa) is a pharmaceutically acceptable salt. In some embodiments, the salt of a compound of Formula (IIb) is a pharmaceutically acceptable salt. In some embodiments, the salt of a compound of Formula (III) is a pharmaceutically acceptable salt. In some embodiments, the salt of a compound of Formula (IIIa) is a pharmaceutically acceptable salt. In some embodiments, the salt of a compound of Formula (IIIb) is a pharmaceutically acceptable salt.

Also provided are embodiments wherein any embodiment above may be combined with any one or more of these embodiments, provided the combination is not mutually exclusive.

As used herein, two embodiments are "mutually exclusive" when one is defined to be something which is different than the other. In other words, when the two embodiments define the same variable or variables in such a way that both definitions cannot simultaneously exist. For example, an embodiment wherein two groups combine to form a cycloalkyl is mutually exclusive with an embodiment in which one group is ethyl and the other group is hydrogen. Similarly, an embodiment wherein one group is $CH_2$ is mutually exclusive with an embodiment wherein the same group is NH.

Also provided is a compound chosen from the Examples disclosed herein.

Also provided are methods of inhibiting at least one DLK function comprising the step of contacting DLK with a compound as described herein. The cell phenotype, cell proliferation, activity of DLK, change in biochemical output produced by active DLK, expression of DLK, or binding of DLK with a natural binding partner may be monitored. Such methods may be modes of treatment of disease, biological assays, cellular assays, biochemical assays, or the like.

Also provided herein are methods of treatment of a DLK-mediated disease comprising the administration of a therapeutically effective amount of a compound as disclosed herein, or a salt thereof, to a patient in need thereof.

In certain embodiments, the disease is chosen from a neurodegenerative disease.

Also provided herein is a compound as disclosed herein for use as a medicament.

Also provided herein is a compound as disclosed herein for use as a medicament for the treatment of a DLK-mediated disease.

Also provided is the use of a compound as disclosed herein as a medicament.

Also provided is the use of a compound as disclosed herein as a medicament for the treatment of a DLK-mediated disease.

Also provided is a compound as disclosed herein for use in the manufacture of a medicament for the treatment of a DLK-mediated disease.

Also provided is the use of a compound as disclosed herein for the treatment of a DLK-mediated disease.

Also provided herein is a method of inhibition of DLK comprising contacting DLK with a compound as disclosed herein, or a salt thereof.

Also provided herein is a method for achieving an effect in a patient comprising the administration of a therapeutically effective amount of a compound as disclosed herein, or a salt thereof, to a patient wherein the effect is chosen from cognition enhancement.

In certain embodiments, the DLK-mediated disease is chosen from a disease that results from traumatic injury to central nervous system and peripheral nervous system neurons (e.g. stroke, traumatic brain injury, spinal cord injury), a disease that results from a chronic neurodegenerative condition (e.g. Alzheimer's disease, frontotemporal dementia, Parkinson's disease, Huntington's disease, amyotrophic lateral sclerosis, spinocerebellar ataxia, progressive supranuclear palsy, Lewy body disease, Kennedy's disease, and other related conditions), a disease that results from neuropathies resulting from neurological damage (chemotherapy-induced peripheral neuropathy, diabetic neuropathy, and related conditions) and a disease that results from cognitive disorders caused by pharmacological intervention (e.g. chemotherapy induced cognitive disorder, also known as chemobrain).

Also provided is a method of modulation of a DLK-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

Definitions

As used herein, the terms below have the meanings indicated.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a straight chain saturated hydrocarbon attached at two or more positions, such as methylene (—CH$_2$—), ethylene (—CH$_2$CH$_2$—), and propylene (—CH$_2$ CH$_2$CH$_2$—). "Alkylene" can thus be described as —(CH$_2$)$_n$— with n being an positive integer. In some embodiments, n is chosen from 1 to 20. In some embodiments, n is chosen from 1 to 10. In some embodiments, n is chosen from 1 to 8. In some embodiments, n is chosen from 1 to 6. Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR' wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. In certain embodiments, said cycloalkyl will comprise a spirocycle ring system. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and one, two, or three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings wherein heteroaryl rings are fused with other heteroaryl rings wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member wherein each said heteroatom may be independently chosen from nitrogen, oxygen, and sulfur. In certain embodiments, said heterocycloalkyl will comprise a spirocycle ring system. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxyl," as used herein, alone or in combination, refers to —OH.

The term "hydroxyalkyl," as used herein, alone or in combination, refers to a hydroxyl group attached to the parent molecular moiety through an alkyl group.

The term "imino," as used herein, alone or in combination, refers to =N—.

The term "iminohydroxyl," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently chosen from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR' wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "spirocycle ring system" refers to a polycyclic ring system comprising two rings such that a single atom is common to both rings.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently chosen from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxyl, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

A "cognitive disorder," as used herein refers to a mental health disorder in which loss of cognitive function is the primary symptom, and which primarily affects learning, memory, perception, and/or problem solving. Cognitive disorders include amnesia, dementia, and delirium. Causes may include damage to the memory portions of the brain, whether from trauma or chemotherapy.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"DLK binder" is used herein to refer to a compound that exhibits an $K_d$ with respect to DLK of no more than about 100 µM and more typically not more than about 50 µM, as measured in the DLK binding assay described generally herein. The DLK binding assay measures the $K_d$ (dissociation constant) for the binding of a compound with the active site of DLK. Compounds disclosed herein have been discovered to bind to DLK. In certain embodiments, compounds will exhibit an $K_d$ with respect to DLK of no more than about 10 µM; in further embodiments, compounds will exhibit a $K_d$ with respect to DLK of no more than about 1 µM; in yet further embodiments, compounds will exhibit a $K_d$ with respect to DLK of not more than about 0.1 µM; in yet further embodiments, compounds will exhibit a $K_d$ with respect to DLK of not more than about 10 nM, as measured in the DLK assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Salts and Polymorphs

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

Formulations

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Administration and Treatment

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of compounds of the invention with: donepezil, rivastigmine, galantamine, and memantine. Further examples include anti-amyloid antibodies and vaccines, anti-Ab antibodies and vaccines, anti-tau antibodies and vaccines, β-secretase inhibitors, 5-HT4 agonists, 5-HT6 antagonists, 5-HT1a antagonists, α7 nicotinic receptor agonists, 5-HT3 receptor antagonists, PDE4 inhibitors, O-glycnacase inhibitors, and other medicines approved for the treatment of Alzheimer's disease. Further examples include metformin, minocycline, tissue plasminogen activator, and other therapies that improve neuronal survival.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating DLK-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of DLK-mediated disorders.

In certain embodiments, the compounds, compositions, and methods disclosed herein may be useful for the treatment of neurological diseases that result from traumatic injury to central nervous system and peripheral nervous system neurons.

In certain embodiments, the compounds, compositions, and methods disclosed herein may be useful for the treatment of stroke.

In certain embodiments, the compounds, compositions, and methods disclosed herein may be useful for the treatment of traumatic brain injury.

In certain embodiments, the compounds, compositions, and methods disclosed herein may be useful for the treatment of of spinal cord injury.

In certain embodiments, the compounds, compositions, and methods disclosed herein may be useful for the treatment of neurologic diseases that result from a chronic neurodegenerative condition.

In certain embodiments, the neurodegenerative condition is Alzheimer's disease.

In certain embodiments, the neurodegenerative condition is frontotemporal dementia.

In certain embodiments, the neurodegenerative condition is Parkinson's disease.

In certain embodiments, the neurodegenerative condition is Huntington's disease.

In certain embodiments, the neurodegenerative condition is amyotrophic lateral sclerosis.

In certain embodiments, the neurodegenerative condition is Alzheimer's disease.

In certain embodiments, the neurodegenerative condition is spinocerebellar ataxia.

In certain embodiments, the neurodegenerative condition is progressive supranuclear palsy.

In certain embodiments, the neurodegenerative condition is Lewy body disease.

In certain embodiments, the neurodegenerative condition is Kennedy's disease.

In certain embodiments, the compounds, compositions, and methods disclosed herein may be useful for the treatment of neuropathies resulting from neural damage.

In certain embodiments, the neuropathy is chemotherapy-induced peripheral neuropathy.

In certain embodiments, the neuropathy is diabetic neuropathy.

In certain embodiments, the compounds, compositions, and methods disclosed herein may be useful for the treatment of cognitive disorders.

In certain embodiments, the cognitive disorder is caused by pharmacological intervention.

In certain embodiments, the cognitive disorder is chemotherapy induced cognitive disorder.

In certain embodiments, the the compounds, compositions, and methods disclosed herein may be coadministered with another therapeutic agent.

In certain embodiments, the the compounds, compositions, and methods disclosed herein may be coadministered with another therapeutic agent for the treatment of cognitive disorders.

Besides being useful for human treatment, compounds and formulations disclosed herein may also be useful for veterinary treatment of companion animals, exotic animals and farm animals, including mammals, rodents, and the like. More preferred animals include horses, dogs, and cats.

List of Abbreviations $Ac_2O$=acetic anhydride; AcCl=acetyl chloride; AcOH=acetic acid; AIBN=azobisisobutyronitrile; aq.=aqueous; BAST=bis(2-methoxyethyl)aminosulfur trifluoride; Bu=butyl; $Bu_3SnH$=tributyltin hydride; $CD_3OD$=deuterated methanol; $CDCl_3$=deuterated chloroform; CDI=1,1'-carbonyldiimidazole; DAST=(diethylamino)sulfur trifluoride; dba=dibenzylideneacetone DBU=1,8-diazabicyclo[5.4.0]undec-7-ene; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethyl-formamide; DMSO-$d_6$=deuterated dimethyl sulfoxide; DMSO=dimethyl sulfoxide; DPPA=diphenylphosphoryl azide; dppf=1,1'-bis (diphenylphosphino)ferrocene; EDC.HCl=EDCI.HCl=1-ethyl-3-(3-dimethylaminopropyl)carbodiimide hydrochloride; Et=ethyl; Et$_2$O=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyl-disilazane; HOBT=1-hydroxybenzotriazole; iPr=i-Pr=isopropyl=2-propyl; iPrOH=i-PrOH=isopropanol; LAH=lithium aluminiumhydride; LDA=lithium diisopropyl amide; LiHMDS=Lithium bis(trimethylsilyl)amide; MeCN=acetonitrile; MeI=methyl iodide; MeOH=methanol; MP-carbonate resin=macroporous triethylammonium methylpolystyrene carbonate resin; MsCl=mesyl chloride; MTBE=methyl tert-butyl ether; n-BuLi=n-butyllithium; NaHMDS=Sodium bis(trimethylsilyl)amide; NaOEt=sodium ethoxide; NaOMe=sodium methoxide; NaOtBu=sodium t-butoxide; NBS=N-bromosuccinimide; NCS=N-chlorosuccinimide; ND=not determined; NIS=N-iodosuccinimide; NMP=N-Methyl-2-pyrrolidone; Pd(Ph$_3$)$_4$=tetrakis(triphenylphosphine)palladium(0); Pd$_2$(dba)$_3$=tris(dibenzylideneacetone)dipalladium(0); PdCl$_2$(PPh$_3$)$_2$=bis(triphenylphosphine)palladium(II) dichloride; PG=protecting group; Ph=phenyl; prep-HPLC=preparative high-performance liquid chromatography; PMBCl=para-methoxybenzyl; PMBCl=para-methoxybenzyl chloride; PMBOH=para-methoxybenzyl alcohol; PyBop=(benzotriazol-1-yloxy)tripyrrolidino-phosphonium hexafluorophosphate; Pyr=pyridine; RT=room temperature; RuPhos=2-dicyclohexylphosphino-2',6'-diisopropoxybiphenyl; sat.=saturated; ss=saturated solution; tBu=t-Bu=tert-butyl=1,1-dimethylethyl; TBAF=tetrabutylammonium fluoride; TBDPS=t-butyldiphenylsilyl; t-BuOH=tBuOH=tert-butanol; T3P=Propylphosphonic Anhydride; TEA=Et$_3$N=triethylamine; TFA=trifluoroacetic acid; TFAA=trifluoroacetic anhydride; THF=tetrahydrofuran; TIPS=triisopropylsilyl; Tol=toluene; TsCl=tosyl chloride; Trt=trityl=(triphenyl)methyl; Xantphos=4,5-Bis(diphenylphosphino)-9,9-dimethylxanthene; XPhos=2-dicyclohexylphosphino-2',4',6'-triisopropylbiphenyl.

General Synthetic Methods for Preparing Compounds

The following schemes can be used to practice the present invention.

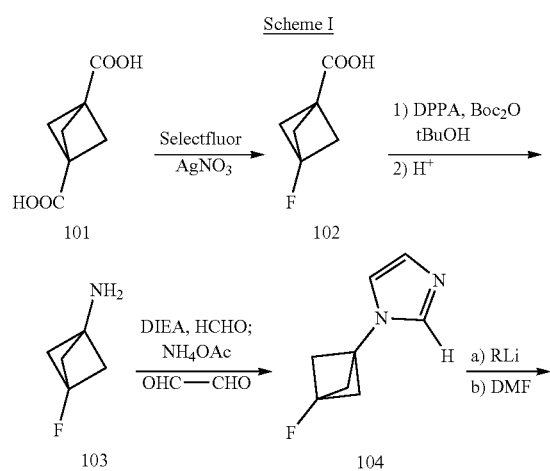

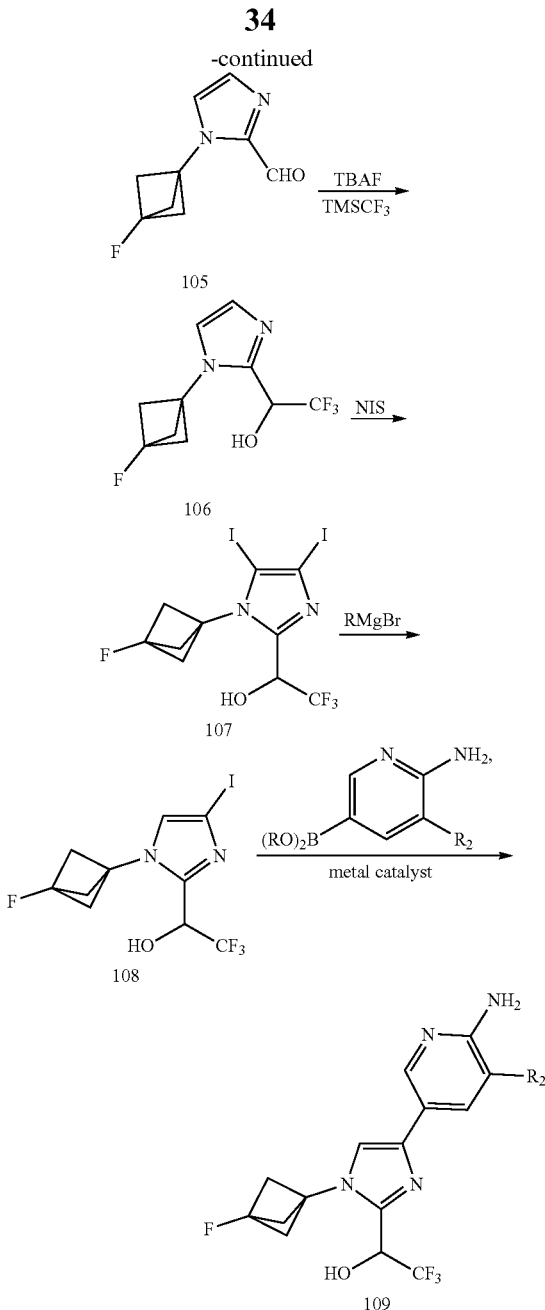

Examples 1 and 2, and similar compounds, can be synthesized by using the general synthetic procedure set forth in Scheme I. Bicyclopentanedicarboxylic acid 101 is converted to the monofluorinated compound 102. Amine 103 is obtained through the intermediacy of an acyl azide and Boc-protected amine through a standard Curtius rearrangement. Condensation with formaldehyde and glyoxal yields imidazole 104. Metalation followed by trapping with N,N-dimethylformamide gives formyl imidazole 105. The trifluoromethyl compound 106 is obtained with a trifluoromethyl anion equivalent. Monoiodo imidazole 108 is obtained from regioselective Grignard-mediated reduction of diiodo imidazole 107. Coupling with a boronic ester affords the desired product 109.

It will be understood that a variety of arylboronic esters can be utilized, affording compounds with various substituents on the pyridine moiety. Furthermore, other anion equivalents can be used, to incorporate different substituents at the imidazole 2-position. Finally, the racemic compound 106 or a successive intermediate can be resolved to afford pure enantiomers.

Scheme II

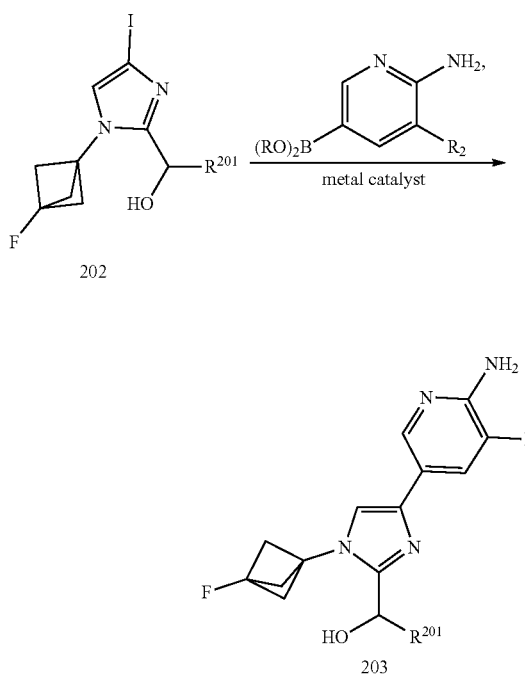

Scheme III

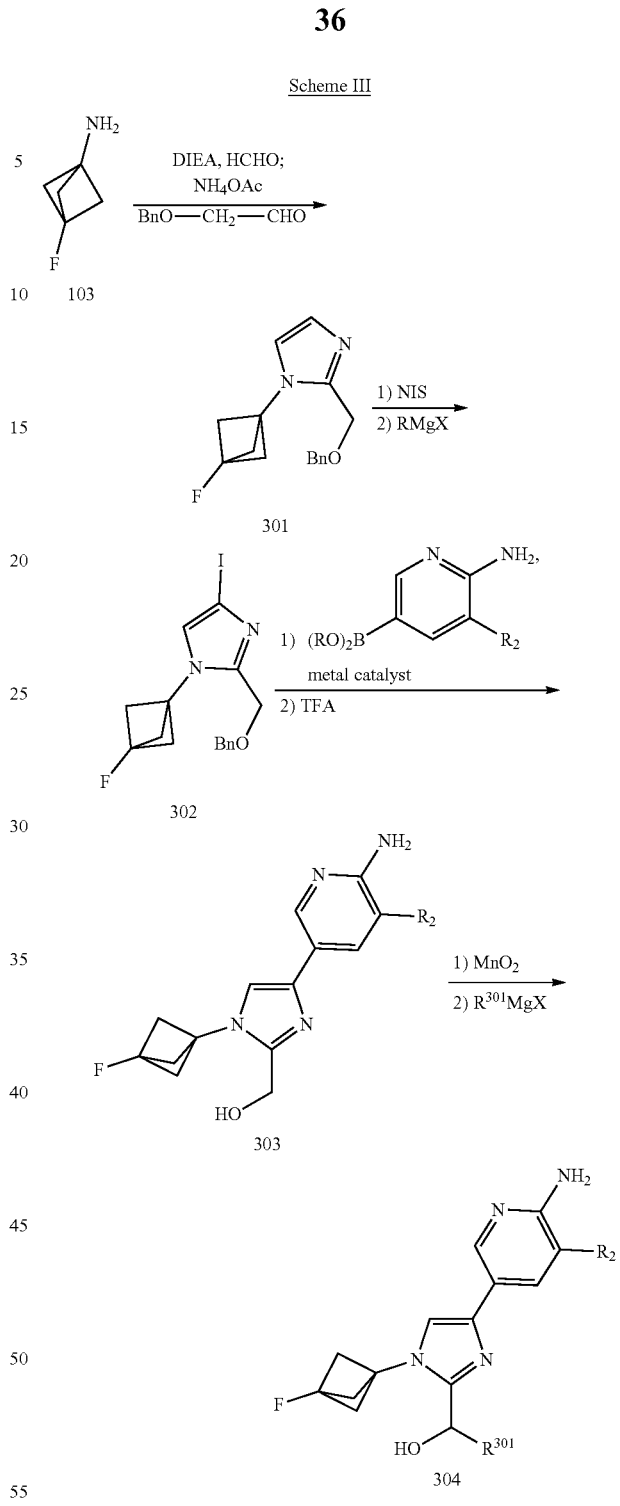

Examples 3 and 4, and similar compounds, can be synthesized by using the general synthetic procedure set forth in Scheme II. Metalation of imidazole 104 followed by trapping with aldehyde $R_{201}$CHO gives secondary alcohol 201. Selective formation of the monoiodo compound 202 is performed as for Scheme I. Coupling of 202 with a boronic ester affords the desired product 203.

Examples 5 and 6, and similar compounds, can be synthesized by using the general synthetic procedure set forth in Scheme III. Amine 103 is condensed as for Scheme I, utilizing benzyloxyacetaldehyde to give the functionalized imidazole 301. As in the previous schemes, the monoiodo compound 302 is obtained through a two-step procedure. Coupling of 202 with a boronic ester, followed by removal of the benzyl protecting group, affords the primary alcohol 303. Oxidation to the aldehyde, followed by reaction with a suitable Grignard reagent, provides the desired product 304.

Scheme IV

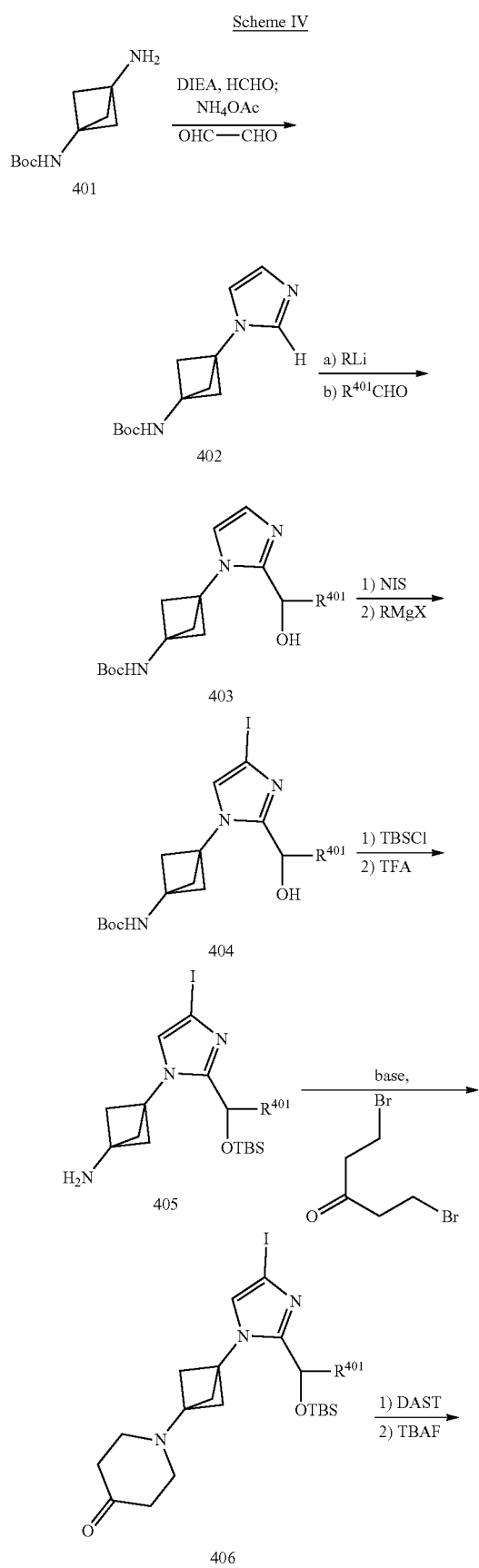

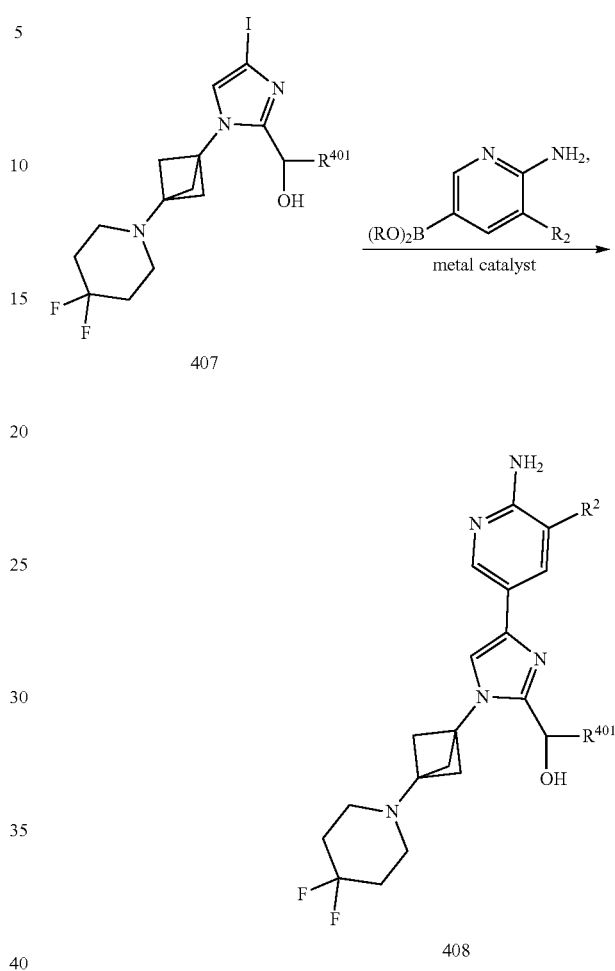

Examples 7 and 8, and similar compounds, can be synthesized by using the general synthetic procedure set forth in Scheme IV. Singly protected bicyclopentanediamine 401 is condensed with glyoxal and formaldehyde to give imidazole 402. Metalation followed by trapping with aldehyde R₄₀₁CHO gives secondary alcohol 403. The monoiodo compound 404 is formed as before. Protection of the alcohol is followed by removal of the Boc protecting group to give primary amine 405. Condensation with 1,5-dibromo-3-pentanone gives 4-piperidone 406. The ketone functionality is converted to a geminal difluoride with DAST; fluoride induced deprotection gives alcohol 407. Coupling with a boronic ester affords the desired product 408.

Scheme V

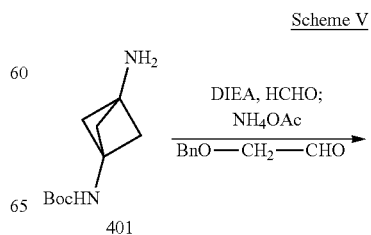

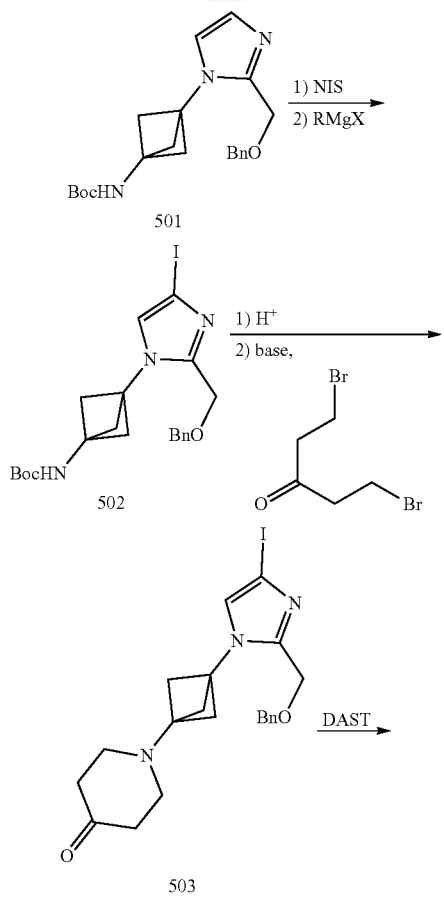

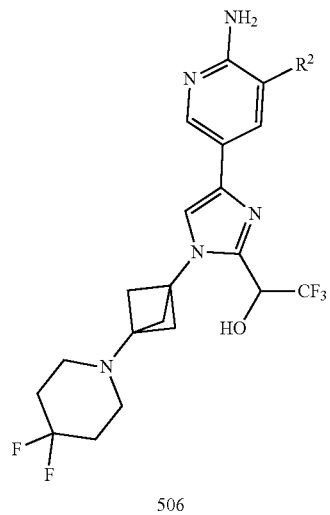

Example 9 and 10, and similar compounds, can be synthesized by using the general synthetic procedure set forth in Scheme V. Singly protected bicyclopentanediamine 401 is condensed with glyoxal and benzyloxyacetaldehyde to give functionalized imidazole 501. The monoiodo compound 502 is formed as before. Similar reaction steps from Scheme IV provide 4-piperidone 503 and 4,4-difluoropiperidine 504. Removal of the benzyl protecting group, followed by oxidation to the aldehyde and reaction with the trifluoromethyl anion equivalent from Scheme I gives trifluoromethyl compound 505. Coupling with a boronic ester affords the desired product 506.

Scheme VI

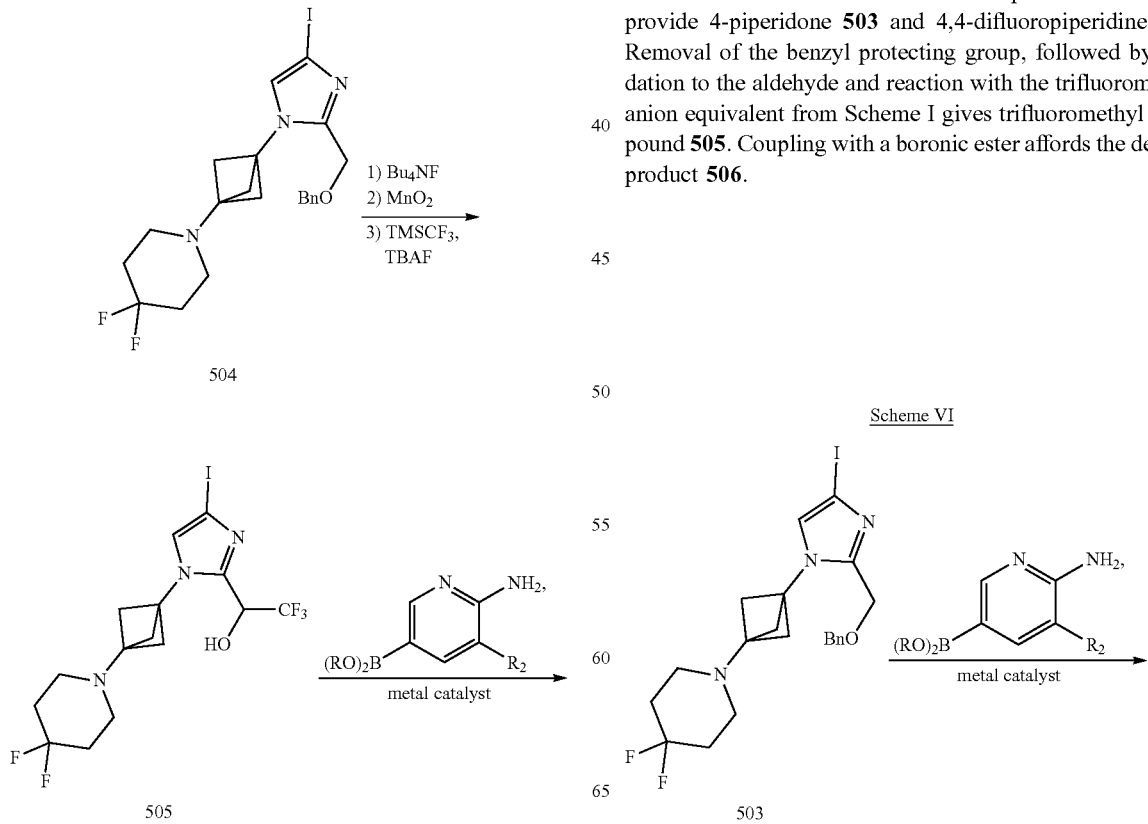

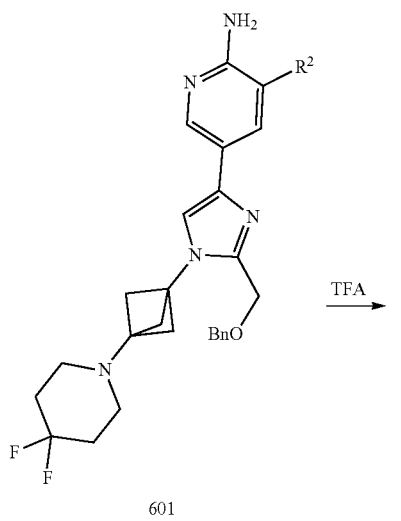

601

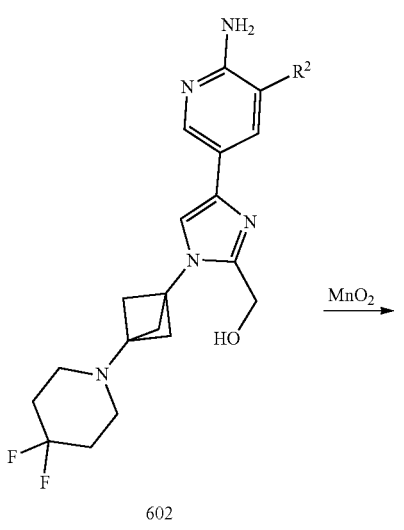

602

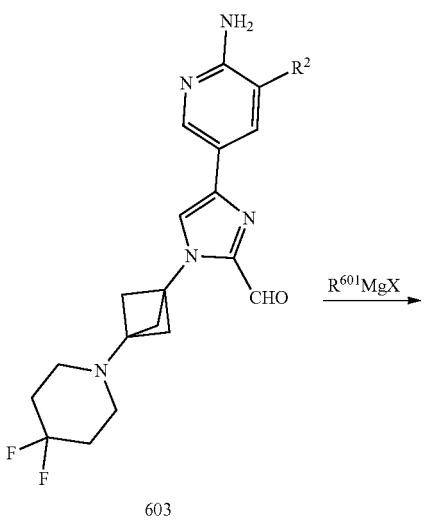

603

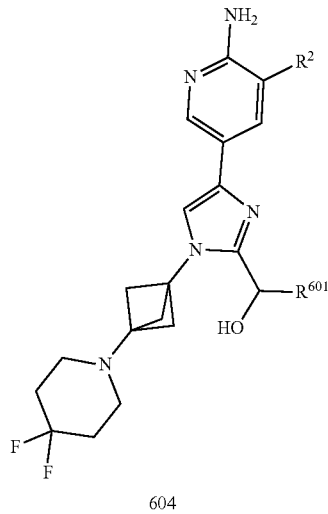

604

Examples 11 and 12, and similar compounds, can be synthesized by using the general synthetic procedure set forth in Scheme VI. Iodoimidazole 503 is coupled with a boronic ester to give 601. Treatment with TFA removes the benzyl group to afford primary amine 602, which is oxidized to aldehyde 603. Reaction with a suitable Grignard reagent provides the desired product 604.

The invention is further illustrated by the following examples.

Examples 1a and 1b

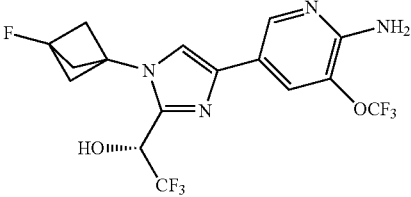 [SMILES: Nc1ncc(-c2cn(C34CC(F)(C3)C4)c([C@@H](O)C(F)(F)F)n2)cc1OC(F)(F)F]

(R)-1-(4-(6-amino-5-(trifluoromethoxy)pyridin-3-yl)-1-(3-fluorobicyclo[1.1.1]pentan-1-yl)-1H-imidazol-2-yl)-2,2,2-trifluoroethanol and

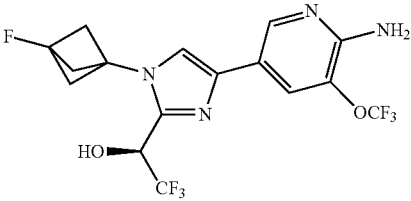 [SMILES: Nc1ncc(-c2cn(C34CC(F)(C3)C4)c([C@H](O)C(F)(F)F)n2)cc1OC(F)(F)F]

(S)-1-(4-(6-amino-5-(trifluoromethoxy)pyridin-3-yl)-1-(3-fluorobicyclo[1.1.1]pentan-1-yl)-1H-imidazol-2-yl)-2,2,2-trifluoroethanol

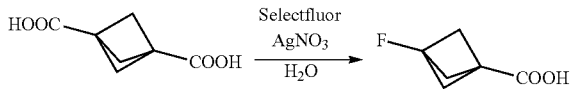 [SMILES: O=C(O)C12CC(C(=O)O)(C1)C2 ; O ; O=C(O)C12CC(F)(C1)C2]

Step 1: 3-fluorobicyclo[1.1.1]pentane-1-carboxylic acid To a solution of bicyclo[1.1.1]pentane-1,3-dicarboxylic acid (50 g, 320.23 mmol) in deoxygenated H$_2$O (1600 mL) was added Selectfluor (283.62 g, 800.59 mmol) and AgNO$_3$ (4.08 g, 24.02 mmol) and the resulting mixture was stirred at 60-63° C. for 12 h under an N$_2$ atmosphere. The mixture was cooled to 25° C., and filtered. The filtrate was extracted with MTBE (1 L×4). The combined organic phase was dried over Na$_2$SO$_4$, filtered and concentrated to afford the title compound (227 g, 1.74 µmol, 68.10% yield) as a brown solid. $^1$H NMR (400 MHz, CDCl$_3$) δ 10.88 (s, 1H), 2.41-2.38 (m, 6H).

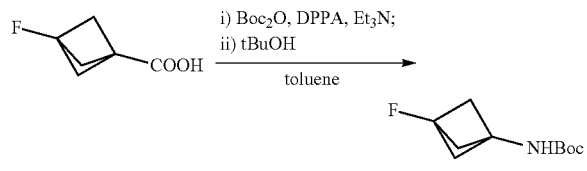

Step 2: tert-butyl (3-fluorobicyclo[1.1.1]pentan-1-yl)carbamate To a solution of the product from the previous step (50 g, 384.27 mmol) and Et$_3$N (42.77 g, 422.70 mmol, 58.83 mL) in toluene (2000 mL) was added Boc$_2$O (83.87 g, 384.27 mmol, 88.28 mL) and DPPA (116.33 g, 422.70 mmol, 91.60 mL) and the resulting mixture was stirred at 25° C. for 0.5 h, then heated to 110° C. for 2 h. Then t-BuOH (113.93 g, 1.54 µmol, 147.01 mL) was added and the mixture was heated to 110° C. for 12 h. Two batches of the reaction mixtures were concentrated under reduced pressure. The residue was purified by silica gel column (Petroleum ether/EtOAc=20/1) to afford the title compound (153 g, crude) as a yellow solid. $^1$H NMR (400 MHz, CDCl$_3$) δ 4.86 (s, 1H), 2.25 (s, 6H), 1.38 (s, 9H).

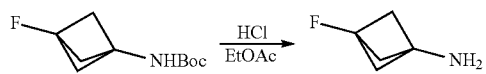

Step 3: 3-fluorobicyclo[1.1.1]pentan-1-amine To a solution of the product from the previous step (153 g, 760.30 mmol) in EtOAc (500 mL) was added HCl/EtOAc (4 M, 500 mL) and the resulting mixture was stirred at 15° C. for 1 h. The reaction mixture was concentrated in vacuum. The crude product was triturated with MTBE at 10° C. for 20 min to afford the title compound (81 g, 588.74 mmol, 77.44% yield, HCl salt) as a white solid. $^1$H NMR (400 MHz, DMSO-d$_6$) δ 9.37 (s, 3H), 2.34 (d, J=2.08 Hz, 6H).

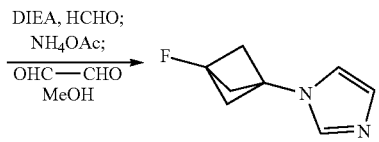

Step 4: 1-(3-fluorobicyclo[1.1.1]pentan-1-yl)-1H-imidazole (Intermediate I) A solution of the product from the previous step (30 g, 218.05 mmol, HCl salt) and DIEA (29.59 g, 228.95 mmol, 39.88 mL) in MeOH (300 mL) was added into a solution of HCHO (23.00 g, 283.47 mmol, 21.10 mL) in MeOH (300 mL) dropwise at 0° C., then NH$_4$OAc (65.21 g, 846.04 mmol) was added, after stirring for 5 min. followed by a solution of glyoxal (38.60 g, 266.02 mmol, 34.77 mL, 40% purity) in MeOH (276 mL) dropwise at 0° C. The mixture was stirred at 15° C. for 16 h. Two batches of the reaction mixture were concentrated in vacuum, and the residue was diluted H$_2$O (600 mL), extracted with EtOAc (600 mL×4), dried over Na$_2$SO$_4$, filtered and concentrated in vacuum. The residue was purified by column chromatography (SiO$_2$, Petroleum ether/EtOAc=9/1-3/1) to afford a first batch of the title compound (32.3 g, 129.48 mmol, 29.69% yield, 61% purity) as a yellow oil and a second batch of the title compound (2.3 g, 5.59 mmol, 1.28% yield, 37% purity) as a yellow oil.

MS (ES$^+$) C$_8$H$_9$FN$_2$ requires: 152, found: 153 [M+H]$^+$.
$^1$H NMR (400 MHz, CDCl$_3$) δ 7.48 (s, 1H), 7.07 (s, 1H), 6.89 (s, 1H), 2.59 (d, J=2.0 Hz, 6H).

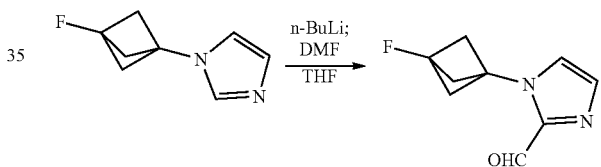

Step 5: 1-(3-fluorobicyclo[1.1.1]pentan-1-yl)-1H-imidazole-2-carbaldehyde To a solution of Intermediate I (3 g, 19.71 mmol) in THF (50 mL) was added n-BuLi (2.5 M, 9.46 mL) dropwise at –70° C. under N$_2$ and the resulting mixture was stirred at –70° C. under N$_2$ for 30 min. Then DMF (1.73 g, 23.66 mmol, 1.82 mL) was added and the mixture was stirred at –70° C. under N$_2$ for another 30 min. The reaction mixture was quenched with NH$_4$Cl (sat. aq, 200 mL), the organic layer was separated, and the aqueous phase was extracted with EtOAc (100 mL×3). The combined organic phase was washed with brine (200 mL), dried over Na$_2$SO$_4$, and concentrated. The residue was purified by silica gel column (Petroleum ether/EtOAc=1/1-0/1) to afford the title compound (2.4 g, 12.12 mmol, 61.48% yield, 91% purity) as a yellow solid. MS (ES$^+$) C$_9$H$_9$FN$_2$O requires: 180, found: 181 [M+H]$^+$.

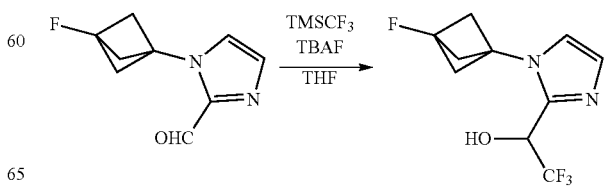

Step 6: 2,2,2-trifluoro-1-(1-(3-fluorobicyclo[1.1.1]pentan-1-yl)-1H-imidazol-2-yl)ethanol Two batches of the following reaction were run in parallel: To a solution of the product from the previous step (1.2 g, 6.66 mmol) in THF (120 mL) was added TMSCF$_3$ (9.47 g, 66.60 mmol) dropwise at −20° C. under N$_2$, followed by addition of TBAF (1 M, 66.60 mL) at −20° C. under N$_2$ and the resulting mixture was stirred at −20° C. for 1 h. The two batches of the reaction mixture were quenched with NH$_4$Cl (sat. aq, 200 mL) and extracted with EtOAc (200 mL×3). The combined organic layers were washed with brine (200 mL), dried over Na$_2$SO$_4$, filtered and concentrated under reduced pressure. The residue was purified by silica gel column (Petroleum ether/EtOAc=1/1-0/1) to afford the title compound (3.5 g, crude) as a yellow solid. MS (ES$^+$) C$_{10}$H$_{10}$F$_4$N$_2$O requires: 250, found: 251 [M+H]$^+$.

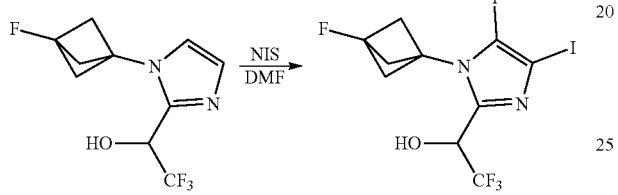

Step 7: 2,2,2-trifluoro-1-(1-(3-fluorobicyclo[1.1.1]pentan-1-yl)-4,5-diiodo-1H-imidazol-2-yl)ethanol To a solution of the product from the previous step (2 g, 7.99 mmol) in DMF (50 mL) was added NIS (8.99 g, 39.97 mmol) and the mixture was stirred at 70° C. for 72 h. Additional NIS (8.99 g, 39.97 mmol) was added and the resulting mixture was stirred at 70° C. for another 3 h. The reaction was quenched with Na$_2$SO$_3$ (sat. aq, 100 mL) and extracted by EtOAc (100 mL×3). The combined organic layers were washed with brine (200 mL), dried over Na$_2$SO$_4$, filtered and concentrated under reduced pressure. The residue was purified by silica gel column (Petroleum ether/EtOAc=10/1 to 5/1) to afford the title compound (2.5 g, 4.18 mmol, 52.33% yield, 84% purity) as a yellow solid. MS (ES$^+$) C$_{10}$H$_8$F$_4$I$_2$N$_2$O requires: 502, found: 503 [M+H]$^+$.

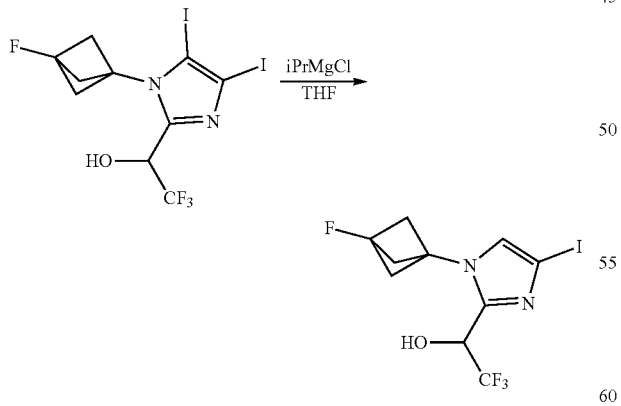

Step 8: 2,2,2-trifluoro-1-(1-(3-fluorobicyclo[1.1.1]pentan-1-yl)-4-iodo-1H-imidazol-2-yl)ethanol To a mixture of the product from the previous step (2.4 g, 4.78 mmol) in THF (50 mL) was added iPrMgCl (2 M, 2.87 mL) dropwise at −70° C. for 15 min under N$_2$ and the resulting mixture was stirred at −70° C. for 1 h. Additional iPrMgCl (2 M, 1 mL) was added and the mixture was stirred at −70° C. for another 1 h. The reaction mixture was quenched with NH$_4$Cl (sat. aq, 80 mL) and extracted with EtOAc (80 mL×3). The combined organic layer was dried over Na$_2$SO$_4$, filtered and concentrated. The residue was purified by column chromatography (SiO$_2$, Petroleum ether/EtOAc=10/1-3/1) and prep-HPLC (column: Phenomenex luna C18 150*40 mm*15 μm; mobile phase: [water (0.225% FA)-ACN]; B %: 26%-56%, 8.5 min) to afford the title compound (670 mg, 1.73 mmol, 36.18% yield, 97% purity) as a white solid. MS (ES$^+$) C$_{10}$H$_9$F$_4$IN$_2$O requires: 376 found: 377 [M+H]$^+$.

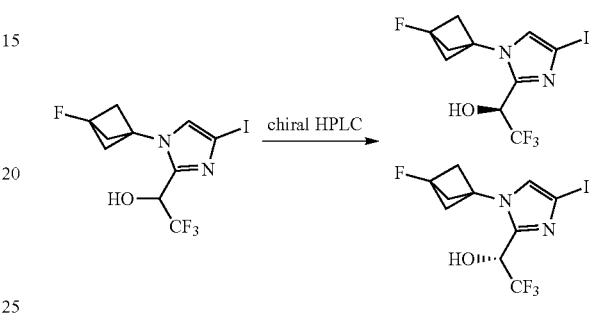

Step 9: (S)-2,2,2-trifluoro-1-(1-(3-fluorobicyclo[1.1.1]pentan-1-yl)-4-iodo-1H-imidazol-2-yl)ethanol and (R)-2,2,2-trifluoro-1-(1-(3-fluorobicyclo[1.1.1]pentan-1-yl)-4-iodo-1H-imidazol-2-yl)ethanol (Intermediates IIa and IIb) The racemic title compound (670 mg) was separated by chiral HPLC (column: DAICEL CHIRALPAK AS (250 mm*30 mm, 10 m); mobile phase: [0.1% NH$_4$OH/MeOH]; B %: 20%-20%, 4.2 min; 50 min) to afford two enantiomers of undetermined absolute stereochemistry.

Intermediate IIa: colorless oil (250 mg, 658.09 μmol, 36.94% yield, 99% purity); retention time=0.501 (column: Chiralpak AS-3 50×4.6 mm I.D., 3 μm; mobile phase: Phase A for CO$_2$ and Phase B for MeOH (0.05% DEA); gradient elution: MeOH (0.05% DEA) in CO$_2$ from 5% to 40%; flow rate: 3 mL/min; wavelength: 220 nm; column temp: 35° C.; back pressure: 100 bar).

Intermediate IIb: colorless oil (240 mg, 619.00 μmol, 34.75% yield, 97% purity); retention time=0.625 (column: Chiralpak AS-3 50×4.6 mm I.D., 3 μm; mobile phase: Phase A for CO$_2$, and Phase B for MeOH (0.05% DEA); gradient elution: MeOH (0.05% DEA) in CO$_2$ from 5% to 40%; flow rate: 3 mL/min; wavelength: 220 nm; column temp: 35° C.; back pressure: 100 bar).

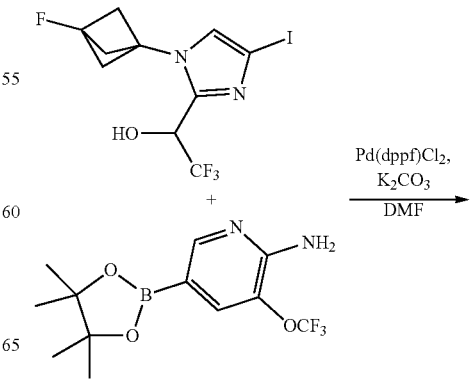

47
-continued

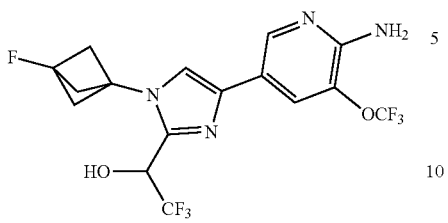

Step 10a: 1-(4-(6-amino-5-(trifluoromethoxy)pyridin-3-yl)-1-(3-fluorobicyclo[1.1.1]-pentan-1-yl)-1H-imidazol-2-yl)-2,2,2-trifluoroethanol, IsomerA (Example 1a) To a mixture of Intermediate IIa (20 mg, 319.07 μmol) and 5-(4,4,5,5-tetramethyl-1,3,2-dioxaborolan-2-yl)-3-(trifluoromethoxy)pyridin-2-amine (126.13 mg, 414.80 μmol) in DMF (5 mL) was added Pd(dppf)Cl$_2$ (39.69 mg, 54.24 μmol) and K$_2$CO$_3$ (2 M, 526.47 uL) under N$_2$ and the resulting mixture was heated to 90° C. for 0.5 h. The reaction mixture was poured into water (30 mL) and extracted with EtOAc (20 mL×3). The combined organic layers were washed with CaCl$_2$ (sat. aq, 50 mL), dried over Na$_2$SO$_4$, filtered and concentrated under reduced pressure. The residue was purified by silica gel column (Petroleum ether/EtOAc=1/1) and re-purified by prep-HPLC (column: Boston Green ODS 150*30 mm*5 μm; mobile phase: [water (0.225% FA)-ACN]; B %: 38%-68%, 10 min) to afford Example 1a as a white solid (79.6 mg, 184.86 μmol, 57.94% yield, 99% purity; retention time=0.837 min (column: Chiralcel OJ-3 50×4.6 mm I.D., 3 μm; mobile phase: Phase A for CO$_2$, and Phase B for MeOH (0.05% DEA); gradient elution: MeOH (0.05% DEA) in CO$_2$ from 5% to 40%; flow rate: 3 mL/min; wavelength: 220 nm column temp: 35° C.; back pressure: 100 bar).

MS (ES$^+$) C$_{16}$H$_{13}$F$_7$N$_4$O$_2$ requires: 426, found: 427 [M+H]$^+$.

$^1$H NMR (400 MHz, CDCl$_3$) δ: 8.38 (s, 1H), 7.75 (s, 1H), 7.08 (s, 1H), 5.08-5.04 (m, 1H), 4.87 (s, 2H), 2.75-2.69 (m, 6H).

Step 10b: 1-(4-(6-amino-5-(trifluoromethoxy)pyridin-3-yl)-1-(3-fluorobicyclo[1.1.1]-pentan-1-yl)-1H-imidazol-2-yl)-2,2,2-trifluoroethanol, Isomer B (Example 1b) The procedure used to obtain Example 1a from Intermediate IIa was performed on Intermediate IIb.

Examples 2a and 2b

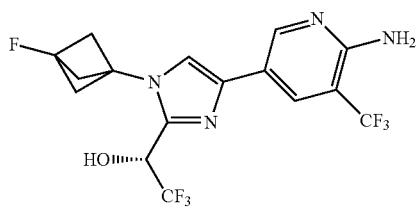 [SMILES: Nc1ncc(-c2cn(C34CC(F)(C3)C4)c([C@@H](O)C(F)(F)F)n2)cc1C(F)(F)F]

48

(R)-1-(4-(6-amino-5-(trifluoromethyl)pyridin-3-yl)-1-(3-fluorobicyclo[1.1.1]pentan-1-yl)-1H-imidazol-2-yl)-2,2,2-trifluoroethanol and

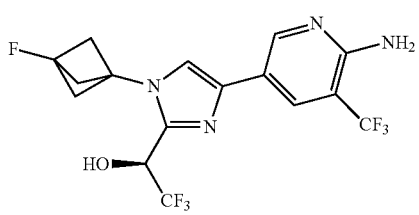 [SMILES: Nc1ncc(-c2cn(C34CC(F)(C3)C4)c([C@H](O)C(F)(F)F)n2)cc1C(F)(F)F]

(S)-1-(4-(6-amino-5-(trifluoromethyl)pyridin-3-yl)-1-(3-fluorobicyclo[1.1.1]pentan-1-yl)-1H-imidazol-2-yl)-2,2,2-trifluoroethanol

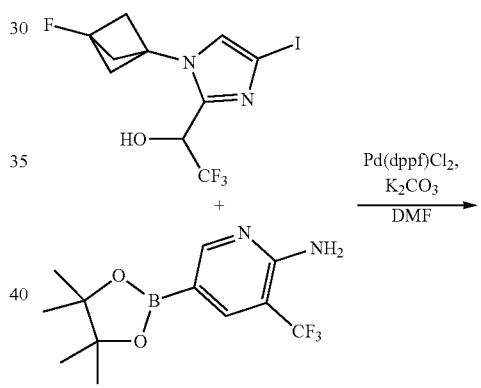

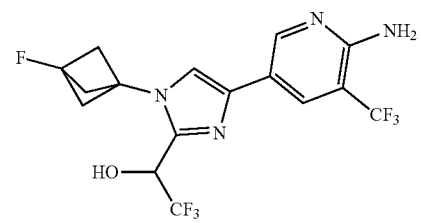

1-(4-(6-amino-5-(trifluoromethyl)pyridin-3-yl)-1-(3-fluorobicyclo[1.1.1]pentan-1-yl)-1H-imidazol-2-yl)-2,2,2-trifluoroethanol (Example 2a) To a mixture of Intermediate IIa (167 mg, 444.04 μmol) and 5-(4,4,5,5-tetramethyl-1,3,2-dioxaborolan-2-yl)-3-(trifluoromethyl)-pyridin-2-amine (166.29 mg, 577.25 μmol) in DMF (5 mL) was added Pd(dppf)Cl$_2$ (55.23 mg, 75.49 μmol) and K$_2$CO$_3$ (2 M, 732.67 uL) under N$_2$ and the resulting mixture was heated to 90° C. for 0.5 h. The mixture was poured into water (30 mL) and extracted with EtOAc (20 mL×3). The combined organic layers were washed with CaCl$_2$ (sat. aq, 50 mL), dried over Na$_2$SO$_4$, filtered and concentrated under reduced pressure. The residue was purified by prep-TLC (Petroleum ether/EtOAc=1/1) and re-purified by prep-HPLC (column: Phenomenex Synergi Max-RP 150*50 mm*10 μm; mobile phase: [water (0.2% FA)-ACN]; B %: 33%-63%, 11 min) to afford Example 2a as a white solid (93.4 mg, 227.64 μmol, 51.27% yield, 100% purity); retention time=0.876 min (column: Chiralcel OJ-3 50×4.6 mm I.D., 3 um. mobile phase: Phase A for $CO_2$ and Phase B for MeOH (0.05% DEA); gradient elution: MeOH (0.05% DEA) in $CO_2$ from 5% to 40%; flow rate: 3 mL/min; wavelength: 220 nm; column temp: 35° C.; back pressure: 100 bar).

MS (ES$^+$) $C_{16}H_{13}F_7N_4O$ requires: 410, found: 411 [M+H]$^+$.

$^1$H NMR (400 MHz, CDCl$_3$) δ: 8.60 (s, 1H), 8.06 (s, 1H), 7.11 (s, 1H), 5.12-5.05 (m, 3H), 2.76-2.70 (m, 6H).

1-(4-(6-amino-5-(trifluoromethyl)pyridin-3-yl)-1-(3-fluorobicyclo[1.1.1]pentan-1-yl)-1H-imidazol-2-yl)-2,2,2-trifluoroethanol (Example 2b) To a mixture of Intermediate IIb (200.00 mg, 531.79 μmol) and 5-(4,4,5,5-tetramethyl-1,3,2-dioxaborolan-2-yl)-3-(trifluoromethyl)pyridin-2-amine (199.15 mg, 691.33 μmol) in DMF (5 mL) was added Pd(dppf)Cl$_2$ (66.15 mg, 90.40 μmol) and K$_2$CO$_3$ (2 M, 877.45 uL) under N$_2$ and the resulting mixture was heated to 90° C. for 16 h. The reaction mixture was poured into water (30 mL) and extracted with EtOAc (20 mL×3). The combined organic layers were washed with CaCl$_2$) (sat. aq, 50 mL), dried over Na$_2$SO$_4$, filtered and concentrated under reduced pressure. The residue was purified by prep-TLC (Petroleum ether/EtOAc=1/1) and re-purified by prep-HPLC (column: Phenomenex Synergi Max-RP 150 mm*50 mm*10 μm; mobile phase: [water (0.2% FA)-ACN]; B %: 33%-63%, 11 min) to afford Example 2b as a white solid (128.7 mg, 310.54 μmol, 58.40% yield, 99% purity); retention time=0.806 min (column: Chiralcel OJ-3 50×4.6 mm I.D., 3 μm; mobile phase: Phase A for $CO_2$ and Phase B for MeOH (0.05% DEA); gradient elution: MeOH (0.05% DEA) in $CO_2$ from 5% to 40%; flow rate: 3 mL/min; wavelength: 220 nm; column temp: 35° C.; back pressure: 100 bar).

MS (ES$^+$) $C_{16}H_{13}F_7N_4O$ requires: 410, found: 411 [M+H]$^+$.

$^1$H NMR (400 MHz, CDCl$_3$) δ: 8.60 (s, 1H), 8.06 (s, 1H), 7.11 (d, J=2.0, 1H), 5.06 (s, 3H), 2.76-2.70 (m, 6H).

Examples 3a and 3b

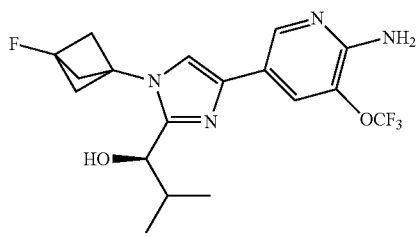 [SMILES: CC(C)[C@@H](O)c1nc(-c2cnc(N)c(OC(F)(F)F)c2)cn1C12CC(F)(C1)C2]

(R)-1-(4-(6-amino-5-(trifluoromethoxy)pyridin-3-yl)-1-(3-fluorobicyclo[1.1.1]pentan-1-yl)-1H-imidazol-2-yl)-2-methylpropan-1-ol and

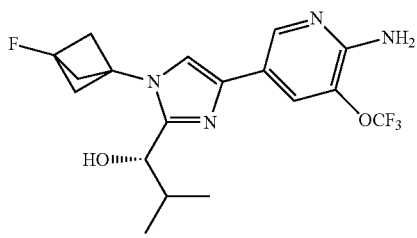 [SMILES: CC(C)[C@H](O)c1nc(-c2cnc(N)c(OC(F)(F)F)c2)cn1C12CC(F)(C1)C2]

(S)-1-(4-(6-amino-5-(trifluoromethoxy)pyridin-3-yl)-1-(3-fluorobicyclo[1.1.1]pentan-1-yl)-1H-imidazol-2-yl)-2-methylpropan-1-ol

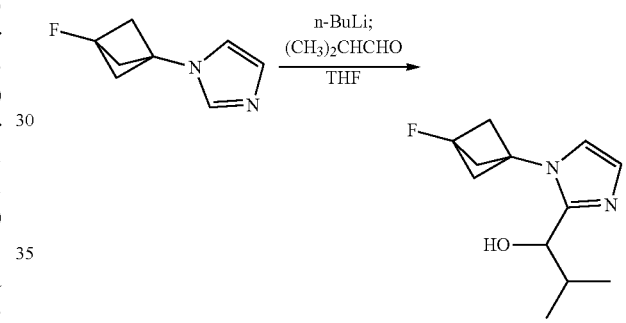

Step 1: 1-(1-(3-fluorobicyclo[1.1.1]pentan-1-yl)-1H-imidazol-2-yl)-2-methylpropan-1-ol To a solution of Intermediate I (10 g, 65.72 mmol) in THF (100 mL) was added n-BuLi (2.5 M, 52.50 mL) dropwise at −70° C. under N$_2$ and the resulting mixture was stirred at −70° C. under N$_2$ for 30 min. Then isobutyraldehyde (7.90 g, 109.56 mmol, 10.00 mL) was added and the mixture was stirred at −70° C. under N$_2$ for another 30 min. The reaction mixture was quenched with NH$_4$Cl (sat. aq, 50 mL) at −70° C. and extracted with EtOAc (50 mL×3). The combined organic layers were washed with brine (50 mL×2), dried over Na$_2$SO$_4$, filtered and concentrated under reduced pressure to afford the title compound (18.8 g, crude) as a yellow solid, which was used into the next step without further purification. MS (ES$^+$) $C_{12}H_{17}FN_2O$ requires: 224, found: 225 [M+H]$^+$.

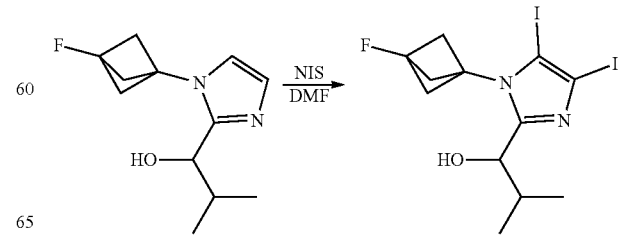

Step 2: 1-(1-(3-fluorobicyclo[1.1.1]pentan-1-yl)-4,5-diiodo-1H-imidazol-2-yl)-2-methylpropan-1-ol To the solution of the product from the previous step (26 g, 82.31 mmol) in DMF (260 mL) was added NIS (88.40 g, 392.92 mmol) at 0° C. and the resulting mixture was stirred at 50° C. for 12 h. The reaction mixture was combined with another batch (1 g scale) and quenched with Na$_2$SO$_3$ (sat. aq, 300 mL), then extracted with EtOAc (300 mL×3). The combined organic layers were washed with brine (200 mL×2), dried over Na$_2$SO$_4$, filtered and concentrated under reduced pressure. The residue was purified by SiO$_2$ gel chromatography (0% to 13% EtOAc in petroleum ether) to afford a first batch of the title compound (9.6 g, 19.76 mmol, 24.01% yield, 98% purity) as a yellow solid and a second batch of the title compound (6.5 g, crude) as a yellow solid.

MS (ES$^+$) C$_{12}$H$_{15}$FI$_2$N$_2$O requires: 476, found: 477 [M+H]$^+$.

$^1$H NMR (400 MHz, CDCl$_3$) δ 4.43 (m, 1H), 2.7-2.88 (m, 6H), 2.9-2.44 (m, 1H), 2.4-2.05 (m, 1H), 1.1-0.92 (m, 6H).

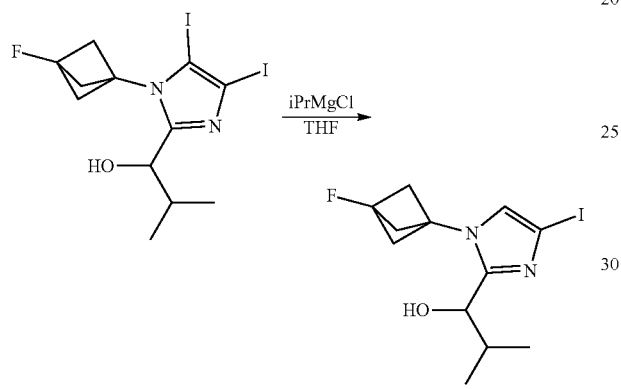

Step 3: 1-(1-(3-fluorobicyclo[1.1.]pentan-1-yl)-4-iodo-1H-imidazol-2-yl)-2-methylpropan-1-ol (Intermediate III) To a mixture of the product from the previous step (8.6 g, 18.06 mmol) in THF (170 mL) was added iPrMgCl (2 M, 10.84 mL) dropwise at −70° C. for 10 min under N$_2$ and the resulting mixture was stirred at −70° C. for 10 min. The reaction mixture was quenched with NH$_4$Cl (sat. aq, 200 mL) at −70° C. and extracted with EtOAc (200 mL×3). The combined organic layers were washed with brine (200 mL×2), dried over Na$_2$SO$_4$, filtered and concentrated under reduced pressure. The residue was purified by SiO$_2$ gel chromatography (0% to 25% EtOAc in petroleum ether) to afford the title compound (4 g, 11.42 mmol, 63.23% yield) as a yellow solid. MS (ES$^+$) C$_{12}$H$_{16}$FIN$_2$O requires: 350, found: 351 [M+H]$^+$.

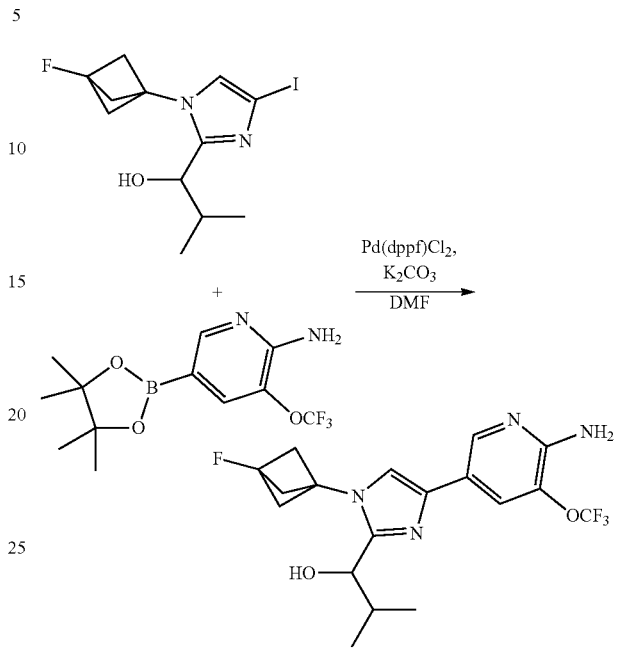

Step 4: 1-(4-(6-amino-5-(trifluoromethoxy)pyridin-3-yl)-1-(3-fluorobicyclo[1.1.1]-pentan-1-yl)-1H-imidazol-2-yl)-2-methylpropan-1-ol A mixture of Intermediate III (2.1 g, 6.00 mmol), 5-(4,4,5,5-tetramethyl-1,3,2-dioxaborolan-2-yl)-3-(trifluoromethoxy)pyridin-2-amine (2.39 g, 7.87 mmol), Pd(dppf)Cl$_2$ (756.01 mg, 1.03 mmol), and K$_2$CO$_3$ (2 M, 9.24 mL) in DMF (40 mL) was degassed and purged with N$_2$ for 3 times and the resulting mixture was stirred at 90° C. for 1 h under N$_2$. The reaction mixture was quenched with H$_2$O (100 mL) and extracted with EtOAc (100 mL×3). The combined organic layers were washed with brine (100 mL×2), dried over Na$_2$SO$_4$, filtered and concentrated under reduced pressure. The residue was purified by column chromatography (0% to 27% EtOAc in Petroleum ether) and reverse phase to afford the title compound (1.2 g, 2.91 mmol, 48.48% yield, 97% purity) as a yellow solid. MS (ES$^+$) C$_{18}$H$_{20}$F$_4$N$_4$O$_2$ requires: 400, found: 401 [M+H]$^+$.

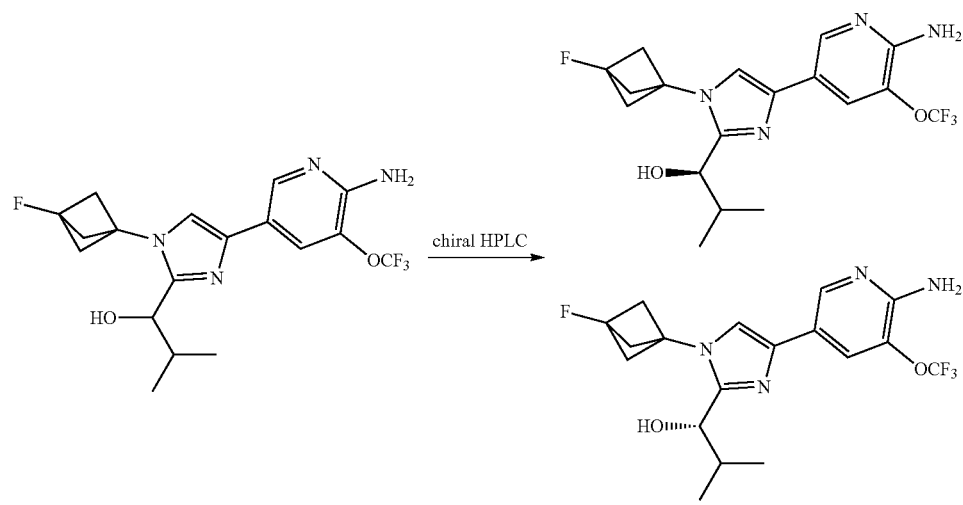 [SMILES: CC(C)C(O)c1nc(-c2cnc(N)c(OC(F)(F)F)c2)cn1C12CC(F)(C1)C2 ; CC(C)[C@@H](O)c1nc(-c2cnc(N)c(OC(F)(F)F)c2)cn1C12CC(F)(C1)C2 ; CC(C)[C@H](O)c1nc(-c2cnc(N)c(OC(F)(F)F)c2)cn1C12CC(F)(C1)C2]

Step 5: (R)-1-(4-(6-amino-5-(trifluoromethoxy)pyridin-3-yl)-1-(3-fluorobicyclo-[1.1.1]pentan-1-yl)-1H-imidazol-2-yl)-2-methylpropan-1-ol (Example 3a) and (S)-1-(4-(6-amino-5-(trifluoromethoxy)pyridin-3-yl)-1-(3-fluorobicyclo[1.1.1]pentan-1-yl)-1H-imidazol-2-yl)-2-methylpropan-1-ol (Examples 3a and 3b) The racemic title compound (1.2 g) was separated by chiral HPLC (column: DAICEL CHIRALPAK AD-H (250 mm*30 mm*5 m); mobile phase: [0.1% NH₄OH/iPrOH]; B %: 25%-25%, 3.25 min; 180 min) to afford two enantiomers of undetermined absolute stereochemistry.

Example 3a was obtained as a white solid (467.7 mg, 1.16 mmol, 38.59% yield, 99% purity); retention time=1.147 (column: Chiralpak AD-3 50 mm*4.6 mm*3 μm; mobile phase: Phase A for CO₂, and Phase B for IPA(0.05% DEA); gradient elution: Bin A from 5% to 40%; flow rate: 3 mL/min; Detector: DAD; column temp: 35° C.; back pressure: 100 bar).

MS (ES⁺) $C_{18}H_{20}F_4N_4O_2$ requires: 400, found: 401 [M+H]⁺.

¹H NMR (400 MHz, CDCl₃) δ 8.34 (d, J=1.6 Hz, 1H), 7.79-7.75 (m, 1H), 6.96 (s, 1H), 4.74 (s, 2H), 4.44-4.40 (m, 1H), 2.76-2.65 (m, 7H), 2.20-2.10 (m, 1H), 1.04 (d, J=6.8 Hz, 3H), 0.98 (d, J=6.8 Hz, 3H).

Example 3b was obtained as a white solid (490.2 mg, 1.21 mmol, 40.44% yield, 99% purity); retention time=1.316 (column: Chiralpak AD-3 50 mm*4.6 mm*3 μm; mobile phase: Phase A for CO₂, and Phase B for IPA(0.05% DEA); gradient elution: Bin A from 5% to 40%; flow rate: 3 mL/min; Detector: DAD; column temp: 35° C.; back pressure: 100 bar).

MS (ES⁺) $C_{18}H_{20}F_4N_4O_2$ requires: 400, found: 401 [M+H]⁺.

¹H NMR (400 MHz, CDCl₃) δ 8.34 (d, J=2.0 Hz, 1H), 7.82-7.73 (m, 1H), 6.96 (s, 1H), 4.74 (s, 2H), 4.44-4.40 (m, 1H), 2.81-2.63 (m, 7H), 2.22-2.09 (m, 1H), 1.04 (d, J=6.8 Hz, 3H), 0.98 (d, J=6.8 Hz, 3H).

Examples 4a and 4b

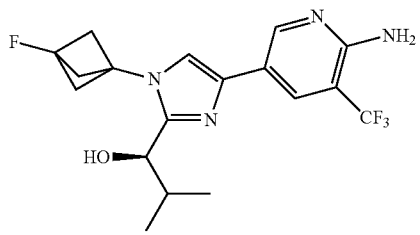 [SMILES: CC(C)[C@@H](O)c1nc(-c2cnc(N)c(C(F)(F)F)c2)cn1C12CC(F)(C1)C2]

(R)-1-(4-(6-amino-5-(trifluoromethyl)pyridin-3-yl)-1-(3-fluorobicyclo[1.1.1]pentan-1-yl)-1H-imidazol-2-yl)-2-methylpropan-1-ol and

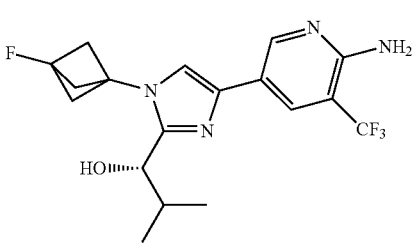 [SMILES: CC(C)[C@H](O)c1nc(-c2cnc(N)c(C(F)(F)F)c2)cn1C12CC(F)(C1)C2]

(S)-1-(4-(6-amino-5-(trifluoromethyl)pyridin-3-yl)-1-(3-fluorobicyclo[1.1.1]pentan-1-yl)-1H-imidazol-2-yl)-2-methylpropan-1-ol

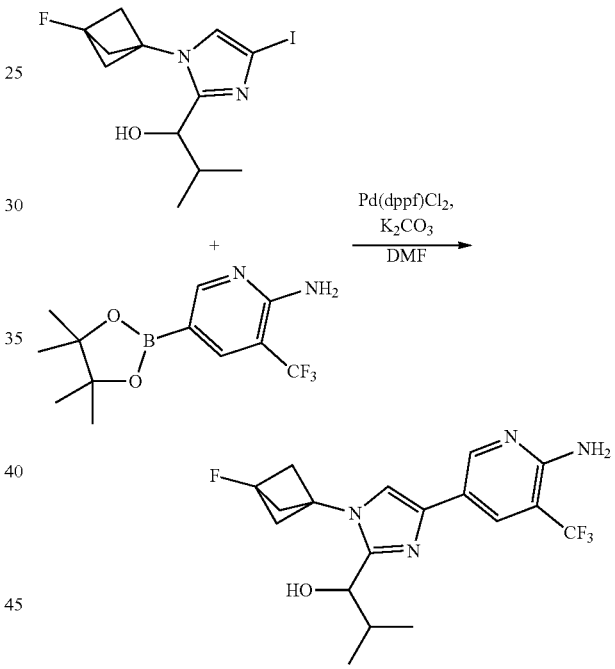

Step 1: 1-(4-(6-amino-5-(trifluoromethyl)pyridin-3-yl)-1-(3-fluorobicyclo[1.1.1]-pentan-1-yl)-1H-imidazol-2-yl)-2-methylpropan-1-ol To a solution of Intermediate III (3 g, 8.57 mmol), 5-(4,4,5,5-tetramethyl-1,3,2-dioxaborolan-2-yl)-3-(trifluoromethyl)pyridin-2-amine (3.21 g, 11.14 mmol), and Pd(dppf)Cl₂ (1.07 g, 1.46 mmol) in DMF (60 mL) was added K₂CO₃ (2 M, 12.90 mL) and the resulting mixture was stirred at 90° C. for 1 h under N₂. The reaction mixture was combined with another batch (100 mg scale). The combined mixture was diluted with H₂O (200 mL) and extracted with EtOAc (200 mL×3). The combined organic layers were washed with brine (200 mL×2), dried over Na₂SO₄, filtered. The filtrate was concentrated under reduced pressure. The residue was purified by SiO₂ gel chromatography (0% to 50% EtOAc in petroleum ether) and reverse phase (basic condition) to afford the title compound (2.48 g, 6.06 mmol, 70.79% yield, 94% purity) as a white solid. MS (ES⁺) $C_{18}H_{20}F_4N_4O$ requires: 384, found: 385 [M+H]⁺.

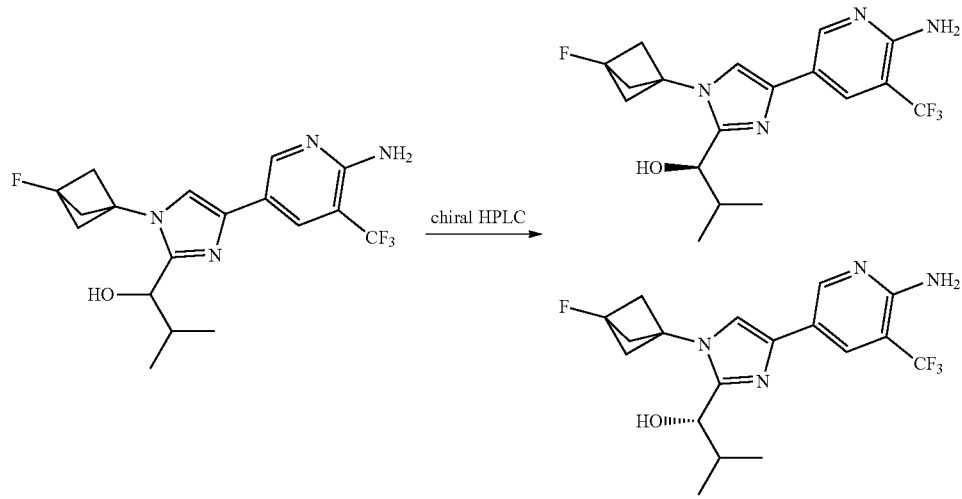 [SMILES: CC(C)C(O)c1nc(-c2cnc(N)c(C(F)(F)F)c2)cn1C12CC(F)(C1)C2 ; CC(C)[C@@H](O)c1nc(-c2cnc(N)c(C(F)(F)F)c2)cn1C12CC(F)(C1)C2 ; CC(C)[C@H](O)c1nc(-c2cnc(N)c(C(F)(F)F)c2)cn1C12CC(F)(C1)C2]

Step 2: (R)-1-(4-(6-amino-5-(trifluoromethyl)pyridin-3-yl)-1-(3-fluorobicyclo[1.1.1]-pentan-1-yl)-1H-imidazol-2-yl)-2-methylpropan-1-ol and (S)-1-(4-(6-amino-5-(trifluoromethyl)pyridin-3-yl)-1-(3-fluorobicyclo[1.1.1]pentan-1-yl)-1H-imidazol-2-yl)-2-methylpropan-1-ol ((Examples 4a and 4b) The racemic title compound (1.5 g) was separated by chiral HPLC (column: DAICEL CHIRALPAK AD-H (250 mm*30 mm*5 m); mobile phase: [0.1% NH₄OH/iPrOH]; B %: 25%-25%, 2.75 min; 721 min) to afford two enantiomers of undetermined absolute sterochemistry.

Example 4a was obtained as a white solid; retention time=1.352 min (column: Chiralpak AD-3 50 mm*4.6 mm*3 μm; mobile phase: Phase A for $CO_2$, and Phase B for IPA (0.05% DEA); gradient elution: IPA (0.05% DEA) in $CO_2$ from 5% to 40%; flow rate: 3 mL/min; Detector: PDA; column temp: 35° C.; back pressure: 100 bar) (495.1 mg, 1.29 mmol, 33.01% yield, 100% purity).

MS (ES⁺) $C_{18}H_{20}F_4N_4O$ requires: 384, found: 385 [M+H]⁺.

¹H NMR (400 MHz, CDCl₃) δ 8.55 (d, J=1.6 Hz, 1H), 8.07 (d, J=1.6 Hz, 1H), 6.99 (s, 1H), 4.97 (s, 2H), 4.42 (dd, J=6.4, 8.8 Hz, 1H), 2.75-2.66 (m, 7H), 2.15 (m, 1H), 1.04 (d, J=6.4 Hz, 3H), 0.98 (d, J=6.8 Hz, 3H).

Example 4b was obtained as a white solid; retention time=1.479 min (column: Amycoat 50 mm*4.6 mm*3 μm; mobile phase: Phase A for $CO_2$, and Phase B for IPA(0.05% DEA); gradient elution: IPA (0.05% DEA) in $CO_2$ from 5% to 40%; flow rate: 3 mL/min; Detector: PDA; column temp: 35° C.; back pressure: 100 bar) (504.8 mg, 1.27 mmol, 32.64% yield, 97% purity)

MS (ES⁺) $C_{18}H_{20}F_4N_4O$ requires: 384, found: 385 [M+H]⁺.

¹H NMR (400 MHz, CDCl₃) δ 8.56 (d, J=1.2 Hz, 1H), 8.08 (d, J=1.6 Hz, 1H), 6.99 (s, 1H), 4.96 (s, 2H), 4.43 (dd, J=6.4, 9.2 Hz, 1H), 2.76-2.62 (m, 7H), 2.20-2.09 (m, 1H), 1.04 (d, J=6.8 Hz, 3H), 0.98 (d, J=6.8 Hz, 3H).

Example 5

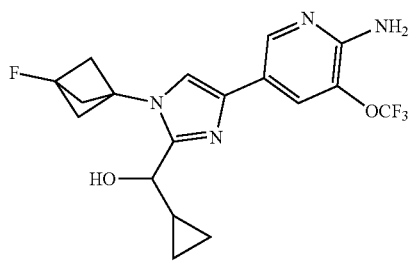 [SMILES: Nc1ncc(-c2cn(C34CC(F)(C3)C4)c(C(O)C3CC3)n2)cc1OC(F)(F)F]

(4-(6-amino-5-(trifluoromethoxy)pyridin-3-yl)-1-(3-fluorobicyclo[1.1.1]pentan-1-yl)-1H-imidazol-2-yl)(cyclopropyl)methanol

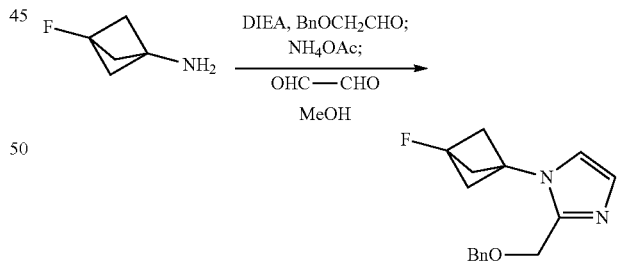

Step 1: 2-((benzyloxy)methyl)-1-(3-fluorobicyclo[1.1.1]pentan-1-yl)-1H-imidazole A solution of 3-fluorobicyclo[1.1.1]pentan-1-amine (3.2 g, 23.26 mmol, HCl salt) and DIEA (3.16 g, 24.42 mmol, 4.25 mL) in MeOH (10 mL) was added to a solution of 2-benzyloxy-acetaldehyde (3.88 g, 25.82 mmol, 3.62 mL) in MeOH (10 mL) dropwise at 0° C., then NH₄OAc (6.96 g, 90.24 mmol) was added. The mixture was stirred 5 min, then a solution of glyoxal (4.12 g, 28.38 mmol, 3.71 mL, 40% purity) in MeOH (10 mL) was added dropwise at 0° C., and the resulting mixture was stirred at 25° C. for 16 h. The mixture was diluted with H₂O (80 mL) and extracted with EtOAc (80 mL×3). The combined organic layers were washed with brine (60 mL×2), dried over Na₂SO₄, filtered and concentrated to afford the title compound (7 g, crude) as a yellow oil. MS (ES⁺) C₁₆H₁₇FN₂O requires: 272, found: 273 [M+H]⁺.

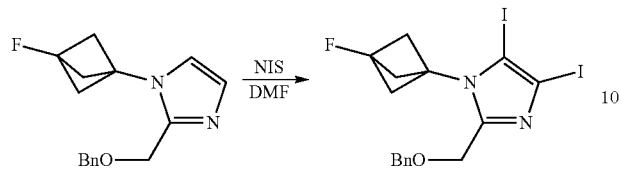

Step 2: 2-((benzyloxy)methyl)-1-(3-fluorobicyclo[1.1.1]pentan-1-yl)-4,5-diiodo-1H-imidazole To a mixture of the product from the previous step (7 g, 25.71 mmol) in DMF (50 mL) was added NIS (28.92 g, 128.53 mmol) at 0° C. and the resulting mixture was stirred at 50° C. for 10 h. The reaction mixture was quenched with Na₂S2O3 (sat. aq, 400 mL) and extracted with EtOAc (300 mL×3). The combined organic layers were washed with brine (150 mL×2), dried over Na₂SO₄, filtered and concentrated in vacuum. The residue was purified by column chromatography (SiO₂, Petroleum ether/EtOAc=10/1-5/1) followed by trituration with MTBE (80 mL). The cake was dried in vacuum to afford the title compound (3.5 g, 6.54 mmol, 25.46% yield, 98% purity) as a yellow solid.

MS (ES⁺) C₁₆H₁₅FI₂N₂O requires: 524, found: 525 [M+H]⁺.

¹H NMR (400 MHz, CDCl₃) δ 7.38-7.06 (m, 5H), 4.60-4.49 (m, 2H), 4.48-4.36 (m, 2H), 2.88-2.74 (m, 6H).

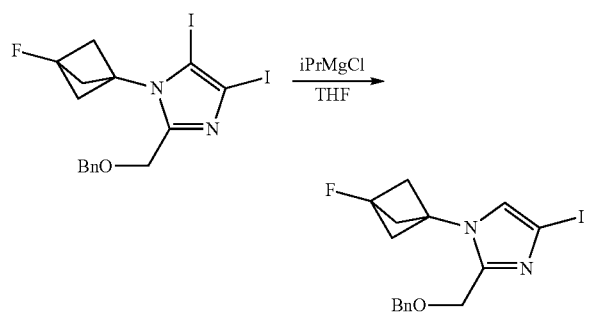

Step 3: 2-((benzyloxy)methyl)-1-(3-fluorobicyclo[1.1.1]pentan-1-yl)-4-iodo-1H-imidazole (Intermediate IV) To a mixture of the product from the previous step (3 g, 5.72 mmol) in THF (60 mL) was added iPrMgCl (2 M, 3.43 mL) dropwise at −70° C., and the resulting mixture was stirred at −70° C. for 1 h. The reaction mixture was quenched with NH₄Cl (sat. aq, 100 mL) and extracted with EtOAc (80 mL×3). The combined organic layers were washed with brine (60 mL×2), dried over Na₂SO₄, filtered and concentrated. The residue was purified by column chromatography (SiO₂, Petroleum ether/EtOAc=20/1-8/1) to afford the title compound (2 g, 4.57 mmol, 79.85% yield, 91% purity) as a yellow solid.

MS (ES⁺) C₁₆H₁₆FIN₂O requires: 398, found: 399 [M+H]⁺.

¹H NMR (400 MHz, CDCl₃) δ 7.33-7.15 (m, 5H), 6.88 (s, 1H), 4.50 (s, 2H), 4.41 (s, 2H), 2.53 (d, J=2.0 Hz, 6H).

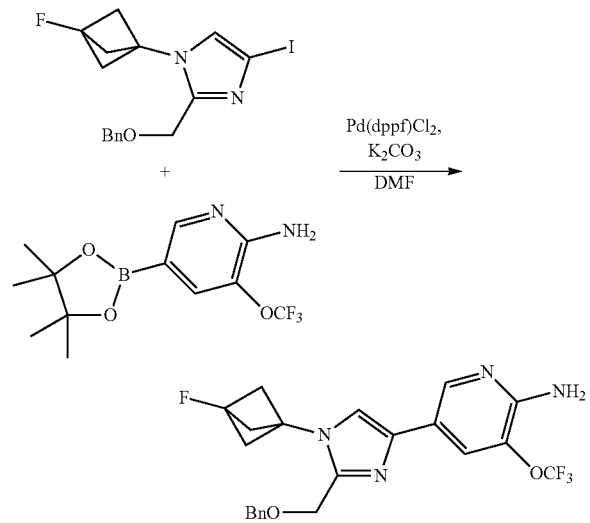

Step 4: 5-(2-((benzyloxy)methyl)-1-(3-fluorobicyclo[1.1.1]pentan-1-yl)-1H-imidazol-4-yl)-3-(trifluoromethoxy)pyridin-2-amine A mixture of Intermediate IV (1 g, 2.44 mmol), 5-(4,4,5,5-tetramethyl-1,3,2-dioxaborolan-2-yl)-3-(trifluoromethoxy)pyridin-2-amine (1.00 g, 3.29 mmol), Pd(dppf)Cl₂ (267.35 mg, 365.38 µmol), and K₂CO₃ (2 M, 4.03 mL) in DMF (30 mL) was degassed and purged with N₂ for 3 times and the resulting mixture was stirred at 90° C. for 1 h under N₂ atmosphere. The reaction mixture was diluted with H₂O (120 mL) and extracted with EtOAc (80 mL×4). The organic layer was washed with brine (80 mL×4), dried over Na₂SO₄, filtered and concentrated. The residue was purified by flash column chromatography (SiO₂, Petroleum ether/EtOAc=8/1-1/1) to afford the title compound (912 mg, 1.57 mmol, 64.29% yield, 77% purity) as a yellow solid. MS (ES⁺) C₂₂H₂₀F₄N₄O₂ requires: 448, found: 449 [M+H]⁺.

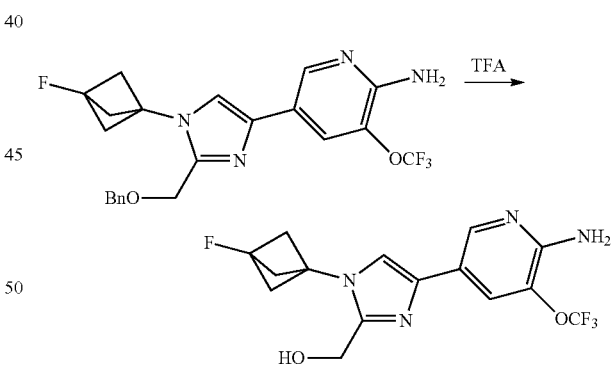

Step 5: (4-(6-amino-5-(trifluoromethoxy)pyridin-3-yl)-1-(3-fluorobicyclo[1.1.1]-pentan-1-yl)-1H-imidazol-2-yl)methanol A mixture of the product from the previous step (1.07 g, 2.39 mmol) in TFA (10 mL) was stirred at 90° C. for 8 h. The reaction mixture was concentrated in vacuum, the residue was diluted with NaHCO₃ (sat. aq, 40 mL) and extracted with EtOAc (40 mL×3). The combined organic layer was dried over Na₂SO₄, filtered and concentrated. The residue was purified by column chromatography (SiO₂, Petroleum ether/EtOAc=2/1-0/1) to afford the title compound (595 mg, 1.66 mmol, 69.59% yield) as a white solid.

MS (ES⁺) C₁₅H₁₄F₄N₄O₂ requires: 358, found: 359 [M+H]⁺.

¹H NMR (400 MHz, CDCl₃) δ 8.26 (d, J=1.7 Hz, 1H), 7.75 (s, 1H), 7.00 (s, 1H), 5.02 (s, 2H), 4.70 (s, 2H), 2.72 (d, J=2.0 Hz, 6H).

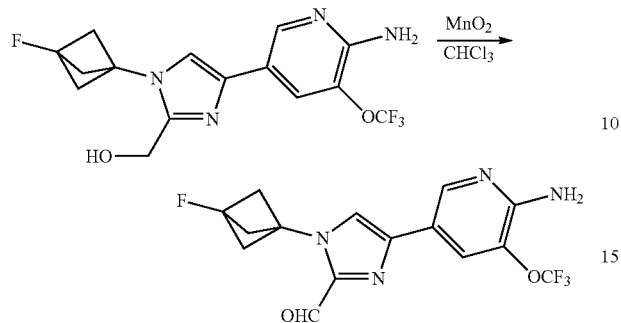

Step 6: 4-(6-amino-5-(trifluoromethoxy)pyridin-3-yl)-1-(3-fluorobicyclo[1.1.1]-pentan-1-yl)-1H-imidazole-2-carbaldehyde To a mixture of the product from the previous step (590 mg, 1.65 mmol) in CHCl₃ (20 mL) was added MnO₂ (1.43 g, 16.47 mmol) at 25° C. and the resulting mixture was stirred at 50° C. for 6 h. Additional MnO₂ (715.80 mg, 8.23 mmol) was added at 25° C. and the resulting mixture was stirred at 50° C. for another 4 h. The reaction mixture was filtered. The cake was washed with CH₂Cl₂ (20 mL×3) and THF (30 mL) and EtOAc (20 mL). The filtrate was concentrated in vacuum. The residue was purified by column chromatography (SiO₂, Petroleum ether/EtOAc=8/1-2/1) to afford the title compound (398 mg, 860.18 µmol, 52.24% yield, 77% purity) as a yellow solid. MS (ES⁺) $C_{15}H_{12}F_4N_4O_2$ requires: 356, found: 357 [M+H]⁺.

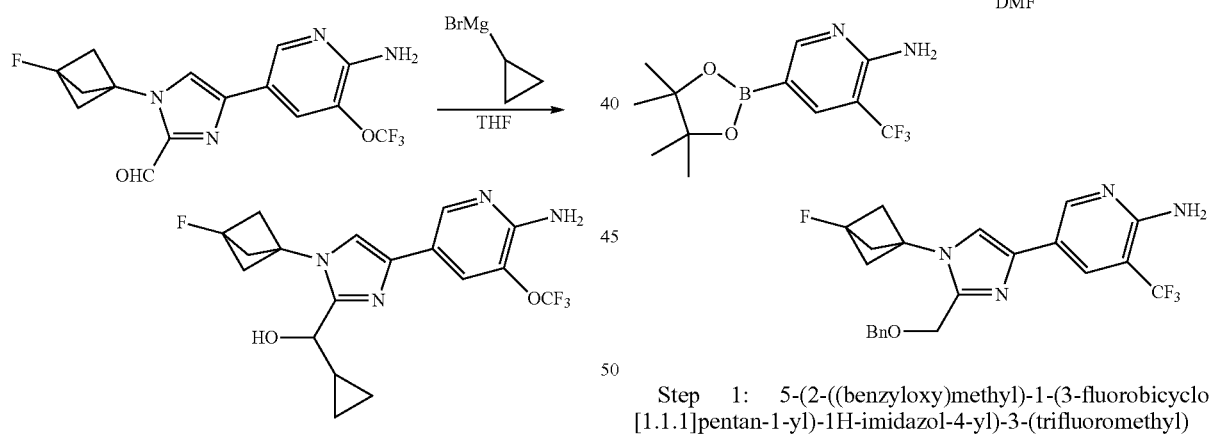

Step 7: (4-(6-amino-5-(trifluoromethoxy)pyridin-3-yl)-1-(3-fluorobicyclo[1.1.1]-pentan-1-yl)-1H-imidazol-2-yl)(cyclopropyl)methanol (Example 5) To a mixture of the product from the previous step (200 mg, 432.25 µmol) in THF (4 mL) was added cyclopropyl-magnesium bromide (0.5 M, 12.97 mL) via syringe dropwise at −70° C. under N₂ and the resulting mixture was stirred at −70° C. for 0.5 h. The reaction mixture was quenched with NH₄Cl (sat. aq, 20 mL) and extracted with EtOAc (20 mL×3). The combined organic layers were dried over Na₂SO₄, filtered and concentrated. The residue was purified by prep-TLC (SiO₂, CH₂Cl₂/EtOAc/Methanol=5/5/1) to afford Example 5 (42.2 mg, 101.70 µmol, 23.53% yield, 96% purity) as a white solid.

MS (ES⁺) C18H₁₈F₄N₄O₂ requires: 398, found: 399 [M+H]⁺.

¹H NMR (400 MHz, CDCl₃) δ 8.34 (d, J=1.8 Hz, 1H), 7.79 (s, 1H), 6.98 (s, 1H), 4.73 (s, 2H), 4.38 (d, J=5.76 Hz, 1H), 3.66 (brs, 1H), 2.74-2.64 (m, 6H), 0.64-0.61 (m, 2H), 0.51-0.44 (m, 1H), 0.40-0.32 (m, 1H).

Example 6

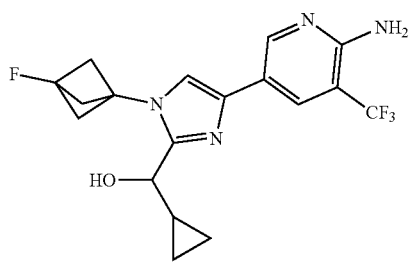 [SMILES: Nc1ncc(-c2cn(C34CC(F)(C3)C4)c(C(O)C3CC3)n2)cc1C(F)(F)F]

(4-(6-amino-5-(trifluoromethyl)pyridin-3-yl)-1-(3-fluorobicyclo[1.1.1]pentan-1-yl)-1H-imidazol-2-yl)(cyclopropyl)methanol

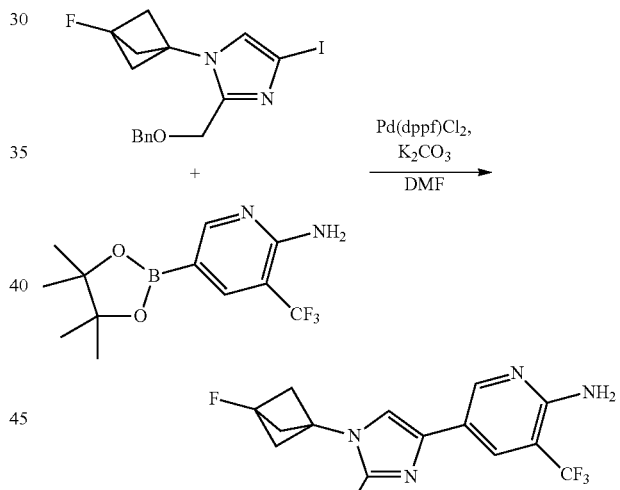

Step 1: 5-(2-((benzyloxy)methyl)-1-(3-fluorobicyclo[1.1.1]pentan-1-yl)-1H-imidazol-4-yl)-3-(trifluoromethyl)pyridin-2-amine A mixture of Intermediate IV (1.76 g, 4.42 mmol), 5-(4,4,5,5-tetramethyl-1,3,2-dioxaborolan-2-yl)-3-(trifluoromethyl)pyridin-2-amine (1.66 g, 5.75 mmol), Pd(dppf)Cl₂ (517.43 mg, 707.16 µmol), and K₂CO₃ (2 M, 7.33 mL) in DMF (45 mL) was degassed and purged with N₂ for 3 times and the resulting mixture was stirred at 90° C. for 4 h. The reaction mixture was diluted H₂O (90 mL) and extracted with EtOAc (90 mL×3). The combined organic layer was washed with brine (90 mL×3), dried over Na₂SO₄, filtered and concentrated. The residue was combined with another batch (204 mg scale) and purified by column chromatography (SiO₂, Petroleum ether/EtOAc=5/1-1/1) to afford the title compound (2.1 g, 4.86 mmol, 109.88% yield) as a yellow solid. MS (ES⁺) $C_{22}H_{20}F_4N_4O$ requires: 432, found: 433 [M+H]⁺.

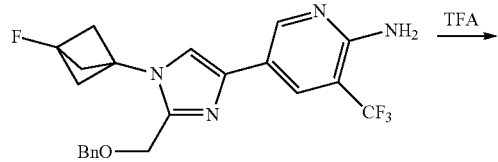

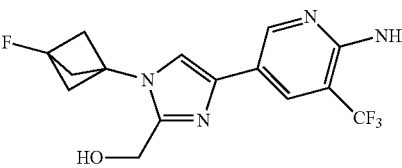

Step 2: (4-(6-amino-5-(trifluoromethyl)pyridin-3-yl)-1-(3-fluorobicyclo[1.1.1]pentan-1-yl)-1H-imidazol-2-yl)methanol A mixture of the product from the previous step (1.6 g, 3.70 mmol) in TFA (20 mL) was stirred at 90° C. for 16 h. The reaction mixture was concentrated in vacuum. The residue was quenched with NaHCO₃ (sat. aq) and extracted with EtOAc (80 mL×3). The combined organic layers were dried over Na₂SO₄, filtered and concentrated. The residue was purified by column chromatography (SiO₂, Petroleum ether/EtOAc=2/1-0/1) to afford the title compound (1.1 g, 3.21 mmol, 86.85% yield, 100% purity) as a white solid. MS (ES⁺) $C_{15}H_{14}F_4N_4O$ requires: 342, found: 343 [M+H]⁺.

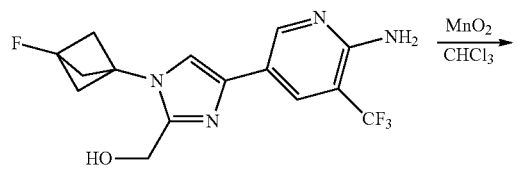

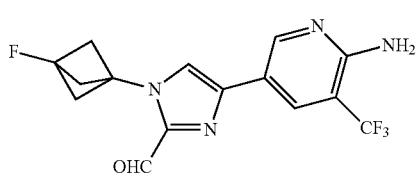

Step 3: 4-(6-amino-5-(trifluoromethyl)pyridin-3-yl)-1-(3-fluorobicyclo[1.1.1]pentan-1-yl)-1H-imidazole-2-carbaldehyde To a mixture of the product from the previous step (700 mg, 2.05 mmol) in CHCl₃ (14 mL) was added MnO₂ (2.67 g, 30.68 mmol) and the resulting mixture was stirred at 50° C. for 21 h. The reaction mixture was filtered, and the cake was washed sequentially with CH₂Cl₂ (20 mL×3), THF (10 mL×3) and EtOAc (5 mL×3). The combined filtrates were concentrated in vacuum. The crude product was combined with another batch (100 mg scale) and triturated by MTBE (40 mL), and the cake was dried in vacuum to afford a first batch of the title compound (540 mg, 1.59 mmol, 77.75% yield) as a yellow solid. The filtrate was purified by prep-TLC (SiO₂, Petroleum ether/EtOAc=2/1) to afford a second batch of the title compound (140 mg, 411.43 μmol, 20.12% yield) as a yellow solid.

MS (ES⁺) $C_{15}H_{12}F_4N_4O$ requires: 340, found: 341 [M+H]⁺.

¹H NMR (400 MHz, CDCl₃) δ 9.82 (d, J=0.88 Hz, 1H), 8.63 (d, J=1.68 Hz, 1H), 8.16 (d, J=2.0 Hz, 1H), 7.26 (s, 1H), 5.07 (s, 2H), 2.81 (d, J=2.0 Hz, 6H).

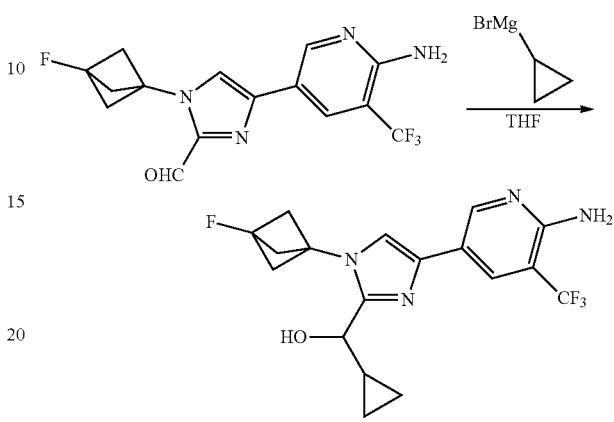

Step 4: (4-(6-amino-5-(trifluoromethyl)pyridin-3-yl)-1-(3-fluorobicyclo[1.1.1]pentan-1-yl)-1H-imidazol-2-yl)(cyclopropyl)methanol (Example 6) To a mixture of the product from the previous step (160 mg, 470.21 μmol) in THF (4 mL) was added cyclopropylmagnesium bromide (0.5 M, 14.11 mL) dropwise at −70° C. under N₂ and the resulting mixture was stirred at −70° C. for 1.5 h. The reaction mixture was combined with another batch (10 mg scale) for work-up. The combined mixture was quenched with NH₄Cl (20 mL) and extracted with EtOAc (20 mL×3). The combined organic layer was dried over Na₂SO₄, filtered and concentrated. The residue was purified by prep-TLC (SiO₂, CH₂Cl₂/EtOAc/MeOH=5/5/1) followed by prep-HPLC (column: Phenomenex Synergi C18 150 mm*30 mm*4 μm; mobile phase: [water (0.225% FA)-ACN]; B %: 20%-50%, 10 min) to afford Example 6 (57.5 mg, 144.37 μmol, 30.70% yield, 96% purity) as a white solid.

MS (ES⁺) $C18H_{18}F_4N_4O$ requires: 382, found: 383 [M+H]⁺.

¹H NMR (400 MHz, CDCl₃) δ 8.56 (d, J=1.6 Hz, 1H), 8.09 (d, J=2.0 Hz, 1H), 7.00 (s, 1H), 4.98 (s, 2H), 4.38 (d, J=7.1 Hz, 1H), 2.74-2.68 (m, 6H), 1.58-1.55 (m, 1H), 0.66-0.47 (m, 2H), 0.51-0.44 (m, 1H), 0.39-0.32 (m, 1H).

Examples 7a and 7b

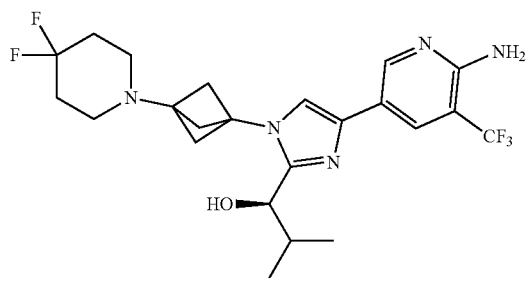

(R)-1-(4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)-2-methylpropan-1-ol and

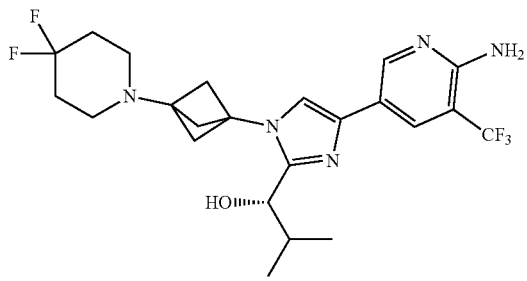 [SMILES: CC(C)[C@H](O)c1nc(-c2cnc(N)c(C(F)(F)F)c2)cn1C12CC(N3CCC(F)(F)CC3)(C1)C2]

(S)-1-(4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)-2-methylpropan-1-ol

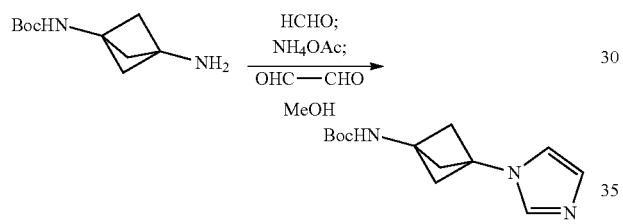

Step 1: tert-butyl(3-(1H-imidazol-1-yl)bicyclo[1.1.1]pentan-1-yl)carbamate A solution of tert-butyl (3-aminobicyclo[1.1.1]pentan-1-yl)carbamate (5 g, 25.22 mmol) in MeOH (20 mL) was added into a solution of HCHO (2.73 g, 33.58 mmol, 2.5 mL) in MeOH (20 mL) dropwise at 0° C., then NH₄OAc (7.50 g, 97.30 mmol) was added, after stirring for 5 min, followed by a solution of glyoxal (4.44 g, 30.60 mmol, 4.00 mL, 40% purity) in methanol (20 mL) dropwise at 0° C. and the resulting mixture was stirred at 15° C. for 16 h. Four batches of the reaction mixture were combined, and H₂O (300 mL) was added. The mixture was extracted with EtOAc (300 mL×3). The combined organic layers were washed with brine (300 mL×2), dried over Na₂SO₄, filtered and concentrated under reduced pressure. The residue was purified by column chromatography (SiO₂, CH₂Cl₂/MeOH=1/0-10/1) to afford the title compound (16.2 g, 46.14 mmol, 45.74% yield, 71% purity) as a yellow oil.

MS (ES⁺) $C_{13}H_{19}N_3O_2$ requires: 249, found: 250 [M+H]⁺.

¹H NMR (400 MHz, CDCl₃) δ 7.55 (s, 1H), 7.11 (s, 1H), 6.92 (d, J=1.24 Hz, 1H), 5.05 (s, 1H), 2.48 (s, 6H), 1.46 (s, 9H).

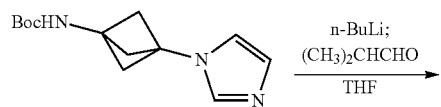

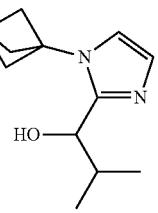

Step 2: tert-butyl(3-(2-(1-hydroxy-2-methylpropyl)-1H-imidazol-1-yl)bicyclo[1.1.1]-pentan-1-yl)carbamate To the solution of the product from the previous step (5.0 g, 14.24 mmol) in THF (160 mL) was added n-BuLi (2.5 M, 40 mL, 7.02 eq) dropwise at −70° C. under N₂. After stirring at −70° C. under N₂ for 0.5 h, 2-methylpropanal (4.74 g, 65.74 mmol, 6 mL) was added, and the resulting mixture was stirred at −70° C. under N₂ for another 1.5 h. The reaction mixture was quenched with NH₄Cl (sat. aq, 100 mL) slowly at −70° C., then the mixture was extracted with EtOAc (200 mL×3). The combined organic layers were washed with brine (200 mL×2), dried over Na₂SO₄, filtered. The filtrate was concentrated under reduced pressure. The residue was purified by column chromatography (SiO₂, Petroleum ether/EtOAc=3/1-0/1) to afford the title compound (4.5 g, 9.10 mmol, 63.91% yield, 65% purity) as a light yellow solid. MS (ES⁺) $C_{17}H_{27}N_3O_3$ requires: 321, found: 322 [M+H]⁺.

Step 3: tert-butyl(3-(2-(1-hydroxy-2-methylpropyl)-4,5-diiodo-1H-imidazol-1-yl)-bicyclo[1.1.1]pentan-1-yl)carbamate To a solution of the product from the previous step (3.2 g, 6.47 mmol) in DMF (100 mL) was added NIS (10 g, 44.45 mmol) at 0° C. and the resulting mixture was stirred at 50° C. for 12 h. Na₂SO₃ (sat. aq, 80 mL) was added at 0° C. and the reaction mixture was stirred at 0° C. for 30 min. The mixture was extracted with EtOAc (200 mL×3). The combined organic layers were washed with brine (200 mL), dried over Na₂SO₄, filtered. The filtrate was concentrated under reduced pressure. The residue was purified by column chromatography (SiO₂, Petroleum ether/EtOAc=10/1-1/1) to afford the title compound (3.0 g, 4.55 mmol, 70.36% yield, 87% purity) as a light yellow solid.

MS (ES⁺) $C_{17}H_{25}I_2N_3O_3$ requires: 573, found: 574 [M+H]⁺.

¹H NMR (400 MHz, CDCl₃) δ 4.99 (s, 1H), 4.52-4.37 (m, 1H), 2.86-2.80 (m, 6H), 2.58-2.32 (m, 1H), 2.04-1.98 (m, 1H), 1.40 (s, 9H), 0.96 (d, J=6.4, 3H), 0.95 (d, J=6.4, 3H).

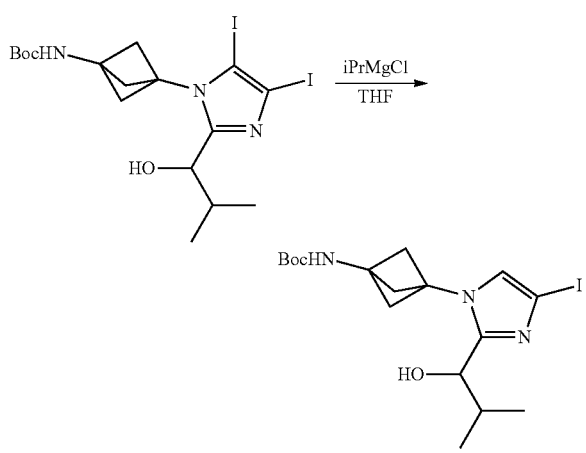

Step 4: tert-butyl(3-(2-(1-hydroxy-2-methylpropyl)-4-iodo-1H-imidazol-1-yl)bicyclo-[1.1.1]pentan-1-yl)carbamate To a mixture of the product from the previous step (4.0 g, 6.98 mmol, 1 eq) in THF (120 mL) was added iPrMgCl (2 M, 4.2 mL) at −70° C. and the resulting mixture was stirred at −70° C. for 1 h under N$_2$. NH$_4$Cl (sat. aq, 60 mL) was added slowly at −70° C., then the mixture was extracted with EtOAc (50 mL×3). The combined organic layers were washed with brine (60 mL×2), dried over Na$_2$SO$_4$, filtered. The filtrate was concentrated under reduced pressure. The residue was purified by column chromatography (SiO$_2$, Petroleum ether/EtOAc=20/1-1/1) to afford the title compound (1.8 g, 3.74 mmol, 53.63% yield, 93% purity) as a light yellow solid.

MS (ES$^+$) C$_{17}$H$_{26}$IN$_3$O$_3$ requires: 447, found: 448[M+H]$^+$.

$^1$H NMR (400 MHz, CDCl$_3$) δ 6.87 (s, 1H), 5.13 (s, 1H), 4.39 (d, J=6.48 Hz, 1H), 2.65-2.54 (m, 6H), 2.16-2.07 (m, 1H), 1.46 (s, 9H), 1.02 (d, J=6.60 Hz, 3H), 0.89 (d, J=6.72 Hz, 3H).

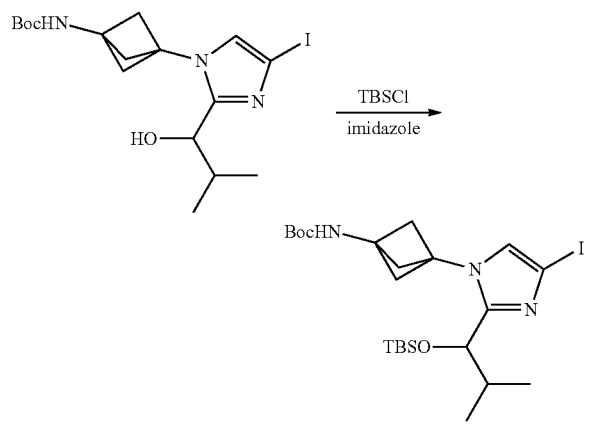

Step 5: tert-butyl(3-(2-(1-((tert-butyldimethylsilyl)oxy)-2-methylpropyl)-4-iodo-1H-imidazol-1-yl)bicyclo[1.1.1]pentan-1-yl)carbamate To a solution of the product from the previous step (1.8 g, 3.74 mmol) in DMF (60 mL) was added TBSCl (2.5 g, 16.59 mmol, 2.03 mL) and imidazole (1.60 g, 23.50 mmol) at 0° C. and the resulting mixture was stirred at 30° C. for 12 h. The reaction mixture was diluted with H$_2$O (60 mL), then the mixture was extracted with EtOAc (100 mL×3). The combined organic layers were washed with brine (200 mL), dried over Na$_2$SO$_4$, and filtered. The filtrate was concentrated under reduced pressure. The residue was purified by column chromatography (SiO$_2$, Petroleum ether/EtOAc=20/1-3/1) to afford the title compound (2.1 g, 3.74 mmol, 99.92% yield) as a light yellow solid.

MS (ES$^+$) C$_{23}$H$_{40}$IN$_3$O$_3$Si requires: 561, found: 562[M+H]$^+$.

$^1$H NMR (400 MHz, CDCl$_3$) δ 6.77 (s, 1H), 4.99 (s, 1H), 4.33 (d, J=9.28 Hz, 1H), 2.44 (s, 6H), 2.14-1.97 (m, 1H), 1.36 (s, 9H), 0.96 (d, J=6.60 Hz, 3H), 0.74 (s, 9H), 0.60 (d, J=6.72 Hz, 3H), 0.21 (s, 6H).

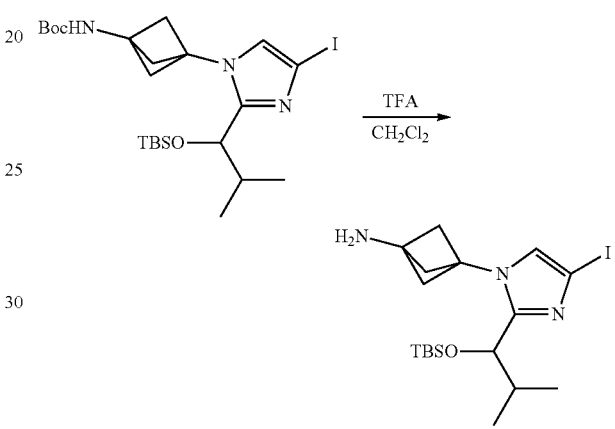

Step 6: 3-(2-(1-((tert-butyldimethylsilyl)oxy)-2-methylpropyl)-4-iodo-1H-imidazol-1-yl)bicyclo[1.1.1]pentan-1-amine To a solution of the product from the previous step (2.1 g, 3.74 mmol) in CH$_2$Cl$_2$ (20 mL) was added TFA (12.94 g, 113.45 mmol, 8.40 mL) at 0° C. dropwise and the resulting mixture was stirred at 20° C. for 4 h. The reaction mixture was concentrated under reduced pressure, then NaHCO$_3$ (sat. aq, 30 mL) was added at 0° C., and the mixture was stirred at 0° C. for 30 min, then extracted with EtOAc (50 mL×3). The combined organic layers were washed with brine (80 mL), dried over Na$_2$SO$_4$, and filtered. The filtrate was concentrated under reduced pressure to afford the title compound (1.7 g, crude) as a light yellow oil, which was used into the next step without further purification. MS (ES$^+$) C$_{18}$H$_{32}$IN$_3$OSi requires: 461, found: 462 [M+H]$^+$.

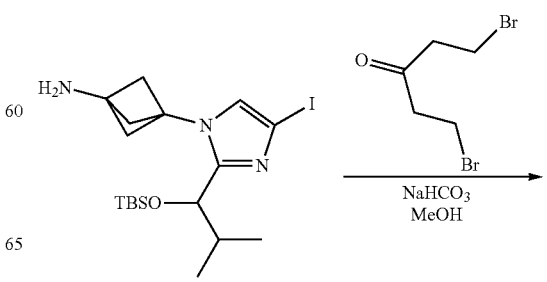

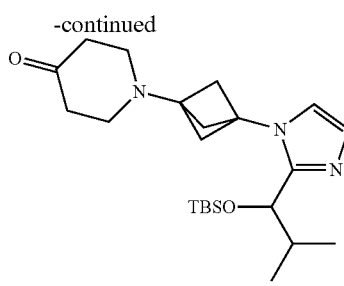

Step 7: 1-(3-(2-(1-((tert-butyldimethylsilyl)oxy)-2-methylpropyl)-4-iodo-1H-imidazol-1-yl)bicyclo[1.1.1]pentan-1-yl)piperidin-4-one To a mixture of the product from the previous step (1.6 g, 3.47 mmol) and NaHCO$_3$ (1.60 g, 19.05 mmol, 740.74 uL) in MeOH (100 mL) was added 1,5-dibromopentan-3-one (2.00 g, 8.20 mmol) in MeOH (10 mL) dropwise at 20° C. and the resulting mixture was stirred at 20° C. for 12 h. The reaction mixture was filtered and the filtrate was concentrated under reduced pressure. Then H$_2$O (40 mL) was added at 0° C., and the mixture was stirred at 0° C. for 30 min, then extracted with EtOAc (50 mL×3). The combined organic layers were washed with brine (100 mL), dried over Na$_2$SO$_4$, and filtered. The filtrate was concentrated under reduced pressure. The residue was purified by column chromatography (SiO$_2$, Petroleum ether/EtOAc=10/1-2/1) to afford the title compound (1.54 g, 2.83 mmol, 81.71% yield) as a light yellow oil.

MS (ES$^+$) C$_{23}$H$_{38}$IN$_3$O$_2$Si requires: 543, found: 544 [M+H]$^+$.

$^1$H NMR (400 MHz, CDCl$_3$) δ 6.92 (s, 1H), 4.45 (d, J=9.36 Hz, 1H), 2.89-2.74 (m, 4H), 2.51 (t, J=6.12 Hz, 4H), 2.38-2.29 (m, 6H), 2.20-2.14 (m, 1H), 1.07 (d, J=6.48 Hz, 3H), 0.85 (s, 9H), 0.71 (d, J=6.64 Hz, 3H), −0.11 (s, 6H).

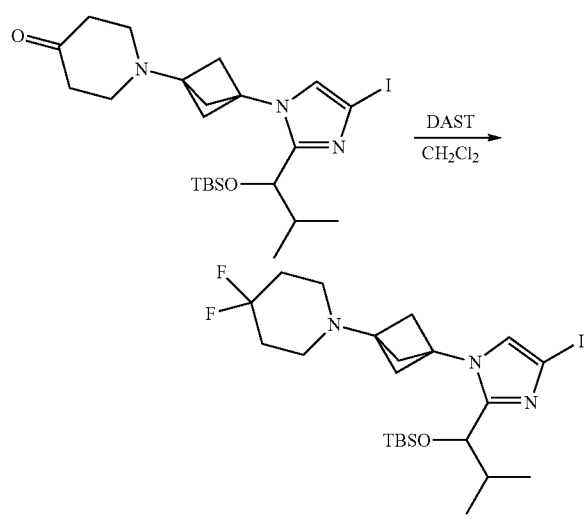

Step 8: 1-(3-(2-(1-((tert-butyldimethylsilyl)oxy)-2-methylpropyl)-4-iodo-1H-imidazol-1-yl)bicyclo[1.1.1]pentan-1-yl)-4,4-difluoropiperidine To a solution of the product from the previous step (800 mg, 1.47 mmol) in CH$_2$Cl$_2$ (30 mL) was added DAST (732.00 mg, 4.54 mmol, 600.00 uL) at 0° C. and the resulting mixture was stirred at 20° C. for 2 h. NaHCO$_3$ (sat. aq, 60 mL) was added at 0° C., and the reaction mixture was stirred at 0° C. for 30 min. The mixture was extracted with CH$_2$Cl$_2$ (60 mL×3). The combined organic layers were washed with brine (80 mL), dried over Na$_2$SO$_4$, and filtered. The filtrate was concentrated under reduced pressure. The residue was combined with another batch (700 mg scale) and purified by column chromatography (SiO$_2$, Petroleum ether/EtOAc=10/1-2/1) to afford the title compound (750 mg, 1.33 mmol, 90.10% yield) as a light yellow solid.

MS (ES$^+$) C$_{23}$H$_{38}$F$_2$IN$_3$OSi requires: 565, found: 566 [M+H]$^+$.

$^1$H NMR (400 MHz, CDCl$_3$) δ 7.04-6.95 (m, 1H), 4.55 (d, J=9.28 Hz, 1H), 2.74 (t, J=5.60 Hz, 4H), 2.47-2.38 (m, 6H), 2.35-2.23 (m, 1H), 2.22-2.04 (m, 4H), 1.18 (d, J=6.48 Hz, 3H), 0.96 (s, 9H), 0.81 (d, J=6.72 Hz, 3H), 0.00 (s, 6H).

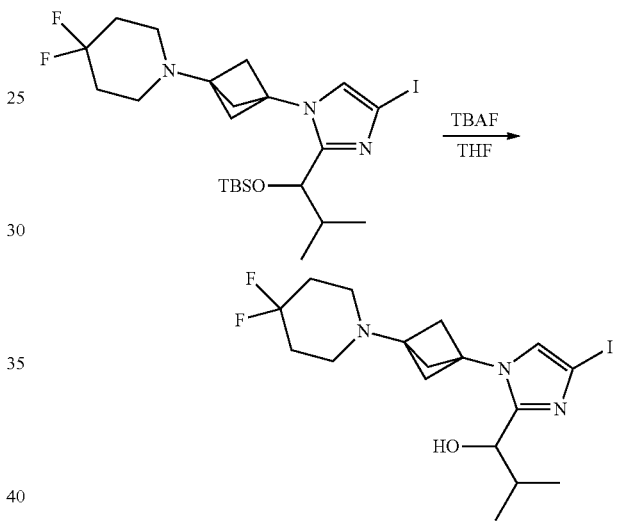

Step 9: 1-(1-(3-(4,4-difluoropiperidin-1-yl)bicyclo[1.1.1]pentan-1-yl)-4-iodo-1H-imidazol-2-yl)-2-methylpropan-1-ol (Intermediate V) To the solution of the product from the previous step (700 mg, 1.24 mmol) in THF (30 mL) was added TBAF (1 M, 4 mL) at 0° C. dropwise and the resulting mixture was stirred at 20° C. for 4 h. The reaction mixture was quenched with NH$_4$Cl (sat. aq, 50 mL) slowly at 0° C., then stirred at 0° C. for 30 min. The mixture was extracted with EtOAc (100 mL×2). The combined organic layers were washed with brine (400 mL), dried over Na$_2$SO$_4$, filtered. The filtrate was concentrated under reduced pressure. The residue was purified by column chromatography (SiO$_2$, Petroleum ether/EtOAc=10/1-2/1) to afford the title compound (450 mg, 997.14 µmol, 80.56% yield) as a light yellow solid.

MS (ES$^+$) C$_{17}$H$_{24}$F$_2$IN$_3$O requires: 451, found: 452 [M+H]$^+$.

$^1$H NMR (400 MHz, CDCl$_3$) δ 6.96-6.79 (m, 1H), 4.39 (s, 1H), 2.65-2.61 (m, 4H), 2.43-2.22 (m, 6H), 2.18-2.09 (m, 1H), 2.09-1.95 (m, 4H), 1.03 (d, J=6.72 Hz, 3H), 0.87 (d, J=6.72 Hz, 3H).

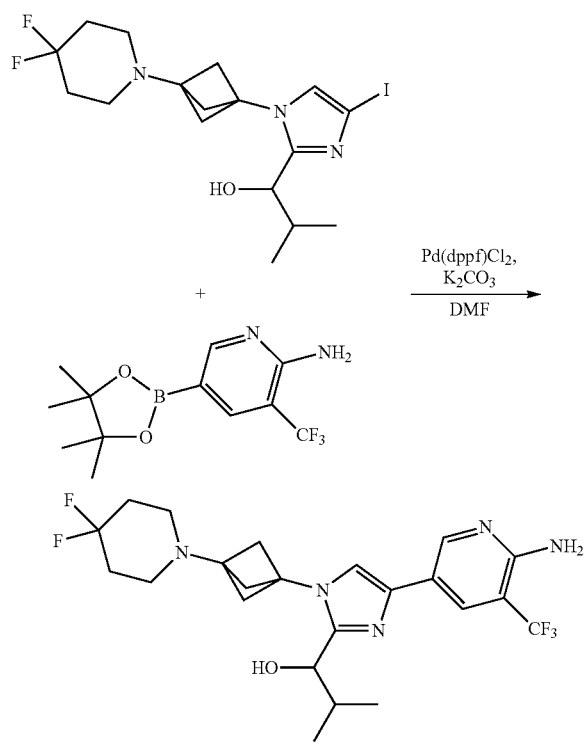

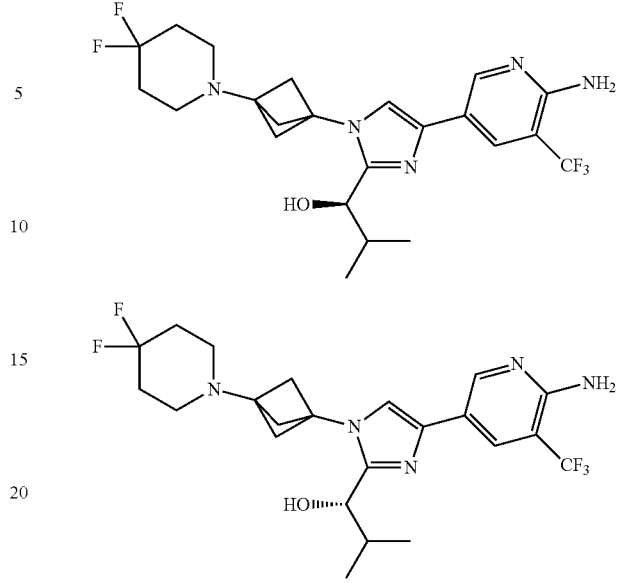

Step 10: 1-(4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)-2-methylpropan-1-ol A mixture of Intermediate V (400 mg, 886.34 µmol), 5-(4,4,5,5-tetramethyl-1,3,2-dioxaborolan-2-yl)-3-(trifluoromethyl)pyridin-2-amine (360.01 mg, 1.25 mmol), Pd(dppf)Cl$_2$ (160.00 mg, 218.67 mol), and K$_2$CO$_3$ (2 M, 1.60 mL) in DMF (20 mL) was degassed and purged 3 times with N$_2$, and the resulting mixture was stirred at 90° C. for 1 h under N$_2$. The reaction mixture was filtered. The filtrate was diluted with H$_2$O (50 ml) and extracted with EtOAc (100 ml×3). The combined organic layers were washed with brine (200 ml×2), dried over Na$_2$SO$_4$, and filtered, and the filtrate was concentrated under reduced pressure. The residue was purified by column chromatography (SiO$_2$, EtOAc/CH$_2$Cl$_2$/MeOH=20/20/1-5/5/2) followed by pre-TLC (EtOAc/CH$_2$Cl$_2$/MeOH=5/5/2) to afford the title compound (400 mg, 790.95 µmol, 89.24% yield, 96% purity) as a light yellow solid. MS (ES$^+$) C$_{23}$H$_{28}$F$_5$N$_5$O requires: 485, found: 486 [M+H]$^+$.

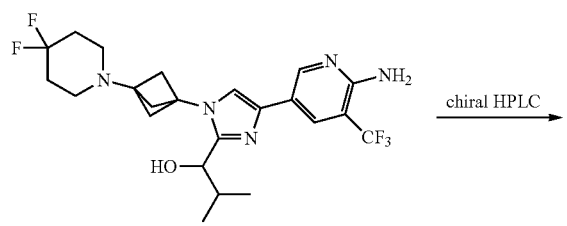

Step 11: (R)-1-(4-(6-amino-5-(trifluoromethyl)pyridin-3-yl)-1-(3-(4,4-difluoro-piperidin-1-yl)bicyclo[1.1.1]pentan-1-yl)-1H-imidazol-2-yl)-2-methylpropan-1-ol and (S)-1-(4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)-2-methylpropan-1-ol (Examples 7a and 7b) The racemic product from the previous step (400 mg) was separated by chiral HPLC (column: DAICEL CHIRALPAK AD (250 mm*30 mm*10 m); mobile phase: [0.1% NH$_4$OH/EtOH]; B %: 40%-40%, 2.5 min, 70 min) to afford two enantiomers of undetermined absolute stereochemistry.

Example 7a was re-purified by prep-HPLC (column: Boston Green ODS 150 mm*30 mm*5 µm; mobile phase: [water (0.225% FA)-ACN]; B %: 30%-60%, 10 min; column temp: 30° C.), and was obtained as a white solid (119.3 mg, 245.73 µmol, 29.82% yield, 100% purity); retention time=1.381 min (column: Amycoat 50 mm*4.6 mm*3 µm; mobile phase: Phase A for CO$_2$, and Phase B for EtOH (0.05% DEA); gradient elution: EtOH (0.05% DEA) in CO$_2$ from 5% to 40%; flow rate: 3 mL/min; wavelength: 220 nm; column temp: 35° C.; back pressure: 100 bar).

MS (ES$^+$) C$_{23}$H$_{28}$F$_5$N$_5$O requires: 485, found: 486 [M+H]$^+$.

$^1$H NMR (400 MHz, CDCl$_3$) δ 8.47 (d, J=1.60 Hz, 1H), 8.00 (d, J=1.84 Hz, 1H), 6.94 (s, 1H), 4.92 (s, 2H), 4.41 (d, J=6.12 Hz, 1H) 2.58 (t, J=5.68 Hz, 4H), 2.33-2.26 (m, 6H), 2.12-2.05 (m, 1H), 2.01-1.93 (m, 4H), 0.95 (d, J=6.72 Hz, 3H), 0.89 (d, J=6.72 Hz, 3H).

Example 7b was re-purified by prep-HPLC: column: Phenomenex Synergi C18 150 mm*25 mm*10 µm; mobile phase: [water (0.225% FA)-ACN]; B %: 20%-42%, 11 min; column temp: 30° C.), and was obtained as a white solid (113.0 mg, 232.75 µmol, 28.25% yield, 100% purity); retention time=1.726 min (column: Amycoat 50 mm*4.6 mm*3 µm; mobile phase: Phase A for CO$_2$, and Phase B for EtOH (0.05% DEA); gradient elution: EtOH (0.05% DEA) in CO$_2$ from 5% to 40%; flow rate: 3 mL/min; wavelength: 220 nm; column temp: 35° C.; back pressure: 100 bar).

MS (ES$^+$) C$_{23}$H$_{28}$F$_5$N$_5$O requires: 485, found: 486 [M+H]$^+$.

$^1$H NMR (400 MHz, CDCl3) δ 8.55 (d, J=1.48 Hz, 1H), 8.08 (d, J=1.84 Hz, 1H), 7.01 (s, 1H), 5.03 (s, 2H), 4.49 (d,

J=6.36 Hz, 1H), 2.66 (br t, J=5.64 Hz, 4H), 2.42-2.34 (m, 6H), 2.16 (m, 1H), 2.10-1.98 (m, 4H), 1.04 (d, J=6.72 Hz, 3H), 0.97 (d, J=6.84 Hz, 3H).

Examples 8a and 8b

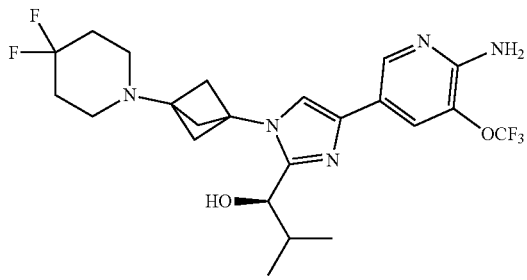 [SMILES: CC(C)[C@@H](O)c1nc(-c2cnc(N)c(OC(F)(F)F)c2)cn1C12CC(N3CCC(F)(F)CC3)(C1)C2]

(R)-1-(4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)-2-methylpropan-1-ol and

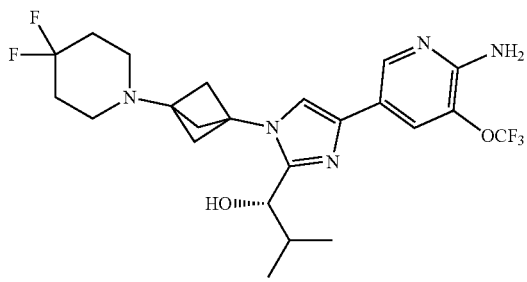 [SMILES: CC(C)[C@H](O)c1nc(-c2cnc(N)c(OC(F)(F)F)c2)cn1C12CC(N3CCC(F)(F)CC3)(C1)C2]

(S)-1-(4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)-2-methylpropan-1-ol

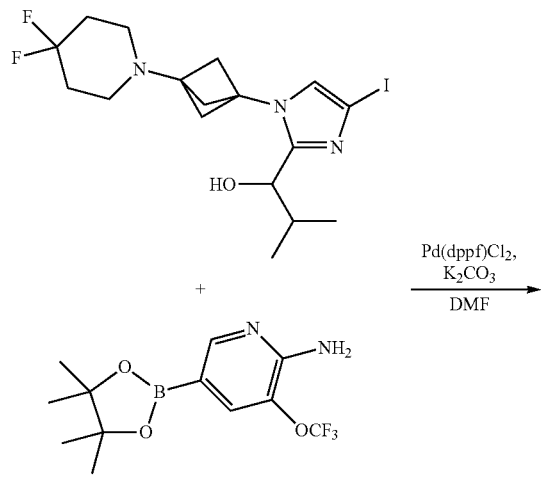

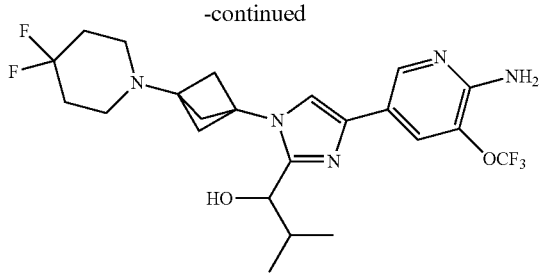

Step 1: 1-(4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)-2-methylpropan-1-ol A mixture of Intermediate V (400 mg, 886.34 μmol), 5-(4,4,5,5-tetramethyl-1,3,2-dioxaborolan-2-yl)-3-(trifluoromethoxy)pyridin-2-amine (400 mg, 1.32 mmol), K$_2$CO$_3$ (2 M, 2.05 mL), and Pd(dppf)Cl$_2$ (160 mg, 218.67 μmol) in DMF (20 mL) was degassed and purged with N$_2$ for 3 times and the resulting mixture was stirred at 90° C. for 1 h under N$_2$. The reaction mixture was filtered. The filtrate was diluted with H$_2$O (50 mL) and extracted with EtOAc (100 mL×3). The combined organic layers were washed with brine (200 mL×2), dried over Na$_2$SO$_4$, and filtered, and the filtrate was concentrated under reduced pressure. The residue was purified by column chromatography (SiO$_2$, EtOAc/CH$_2$Cl$_2$/MeOH=20/20/1-5/5/2) followed by pre-HPLC (column: Phenomenex luna C18 150 mm*40 mm*15 μm; mobile phase: [water (0.225% FA)-ACN]; B %: 11%-41%, 8.5 min; column temp: 30° C.) to afford the title compound (400 mg, 749.76 μmol, 84.59% yield, 94% purity) as a light yellow solid. MS (ES$^+$) C$_{23}$H$_{28}$F$_5$N$_5$O$_2$ requires: 501, found: 502 [M+H]$^+$.

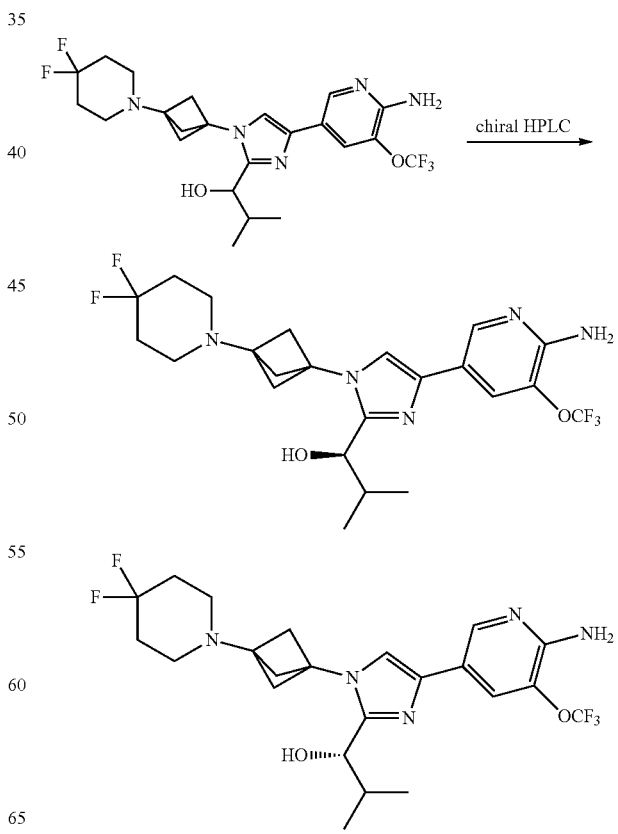

Step 2: (R)-1-(4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)-2-methylpropan-1-ol and (S)-1-(4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)-2-methylpropan-1-ol (Examples 8a and 8b)

The racemic compound from the previous step (400 mg) was separated by chiral HPLC (column: DAICEL CHIRALPAK AD-H(250 mm*30 mm*5 m); mobile phase: [0.1% NH₄OH/EtOH]; B %: 25%-25%, 6.5 min; 45 min) to afford two enantiomers of undetermined absolute stereochemistry.

Example 8a was obtained as a white solid (107.6 mg, 214.56 µmol, 28.62% yield, 100% purity); retention time=1.238 min (column: Chiralpak AD-3 50 mm*4.6 mm*3 uµm; mobile phase: Phase A for CO₂, and Phase B for EtOH (0.05% DEA); gradient elution: EtOH (0.05% DEA) in CO₂ from 5% to 40%; flow rate: 3 mL/min; wavelength: 220 nm; column temp: 35° C.; back pressure: 100 bar).

MS (ES⁺) $C_{23}H_{28}F_5N_5O_2$ requires: 501, found: 502 [M+H]⁺.

¹H NMR (400 MHz, CDCl₃) δ 8.33 (d, J=1.84 Hz, 1H), 7.77 (d, J=1.6 Hz, 1H), 6.99 (s, 1H), 4.76 (s, 2H), 4.48 (dd, J=8.66, 6.24 Hz, 1H), 2.96 (d, J=8.80 Hz, 1H), 2.66 (t, J=5.68 Hz, 4H), 2.42-2.31 (m, 6H), 2.20-2.12 (m, 1H), 2.11-2.00 (m, 4H), 1.03 (d, J=6.72 Hz, 3H), 0.96 (d, J=6.86 Hz, 3H).

Example 8b was obtained as a white solid (146.4 mg, 291.93 µmol, 38.94% yield, 100% purity); retention time=1.492 min (column: Chiralpak AD-3 50 mm*4.6 mm*3 µm; mobile phase: Phase A for CO₂, and Phase B for EtOH (0.05% DEA); gradient elution: EtOH (0.05% DEA) in CO₂ from 5% to 40%; flow rate: 3 mL/min; wavelength: 220 nm; column temp: 35° C.; back pressure: 100 bar).

MS (ES⁺) $C_{23}H_{28}F_5N_5O_2$ requires: 501, found: 502 [M+H]⁺.

¹H NMR (400 MHz, CDCl₃) δ 8.34 (d, J=1.83 Hz, 1H), 7.80-7.74 (m, 1H), 6.99 (s, 1H), 4.77 (s, 2H), 4.48 (dd, J=8.68, 6.24 Hz, 1H), 2.97 (d, J=8.68 Hz, 1H), 2.66 (t, J=5.68 Hz, 4H), 2.41-2.33 (m, 6H), 2.21-2.12 (m, 1H), 1.97-2.11 (m, 4H), 1.03 (d, J=6.60 Hz, 3H), 0.97 (d, J=6.72 Hz, 3H).

Examples 9a and 9b

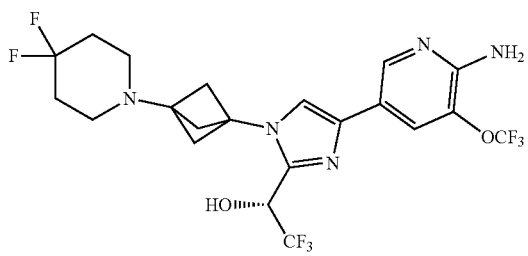 [SMILES: Nc1ncc(-c2cn(C34CC(N5CCC(F)(F)CC5)(C3)C4)c([C@@H](O)C(F)(F)F)n2)cc1OC(F)(F)F]

(R)-1-(4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)-2,2,2-trifluoroethanol and

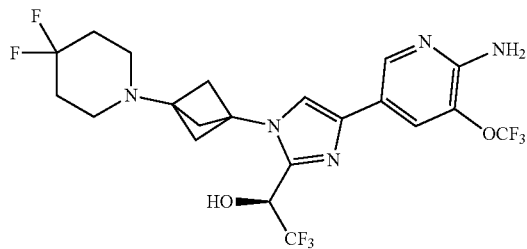 [SMILES: Nc1ncc(-c2cn(C34CC(N5CCC(F)(F)CC5)(C3)C4)c([C@H](O)C(F)(F)F)n2)cc1OC(F)(F)F]

(S)-1-(4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)-2,2,2-trifluoroethanol

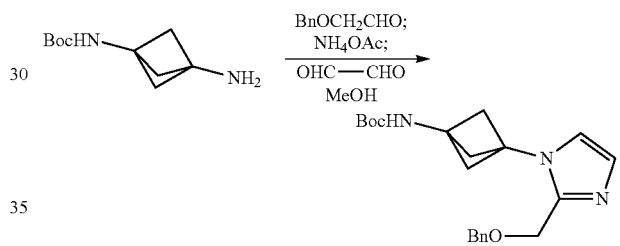

Step 1: tert-butyl(3-(2-((benzyloxy)methyl)-1H-imidazol-1-yl)bicyclo[1.1.1]pentan-1-yl)carbamate To a mixture of 2-benzyloxyacetaldehyde (4.19 g, 27.90 mmol, 3.92 mL) in MeOH (125 mL) were added tert-butyl (3-aminobicyclo [1.1.1]pentan-1-yl)carbamate (5 g, 25.22 mmol), NH₄OAc (6.57 g, 85.23 mmol) followed by a solution of glyoxal (4.45 g, 30.67 mmol, 4.01 mL, 40% purity) in MeOH (25 mL) dropwise at 0° C. The mixture was stirred at 25° C. for 16 h. Two batches of the reaction mixture were combined. The combined mixture was diluted with H₂O (500 mL) and extracted with EtOAc (400 mL×4). The combined organic layers were dried over Na₂SO₄, filtered and concentrated in vacuum to afford the title compound (22 g, crude) as a yellow oil. MS (ES⁺) $C_{21}H_{27}N_3O_3$ requires: 369, found: 370 [M+H]⁺.

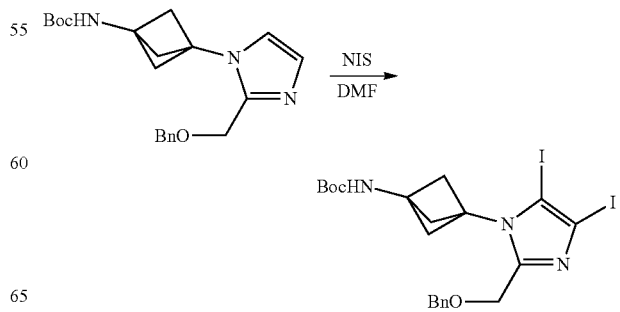

Step 2: tert-butyl(3-(2-((benzyloxy)methyl)-4,5-diiodo-1H-imidazol-1-yl)bicyclo-[1.1.1]pentan-1-yl)carbamate To a mixture of the product from the previous step (22 g, 59.55 mmol) in DMF (120 mL) was added NIS (66.98 g, 297.73 mmol) at 0° C. The mixture was stirred at 50° C. for 9 h. Two batches of the reaction mixture were combined, quenched with Na₂S2O3 (sat. aq, 400 mL), and extracted with EtOAc (400 mL×3). The combined organic layers were washed with brine (300 mL×2), dried over Na₂SO₄, filtered and concentrated. The residue was purified by column chromatography (SiO₂, Petroleum ether/EtOAc=10/1 to 3/1), then triturated by MTBE (80 mL) and filtered. The cake was washed with EtOAc (30 mL) and dried in vacuum to afford the title compound (10 g, 16.10 mmol, 13.52% yield, 100% purity) as a white solid. MS (ES⁺) $C_{21}H_{25}I_2N_3O_3$ requires: 621, found: 622 [M+H]⁺. ¹H NMR (400 MHz, CDCl₃) δ 7.43-7.22 (m, 5H), 5.02 (brs, 1H), 4.64 (s, 2H), 4.51 (s, 2H), 2.82 (s, 6H), 1.48 (s, 9H).

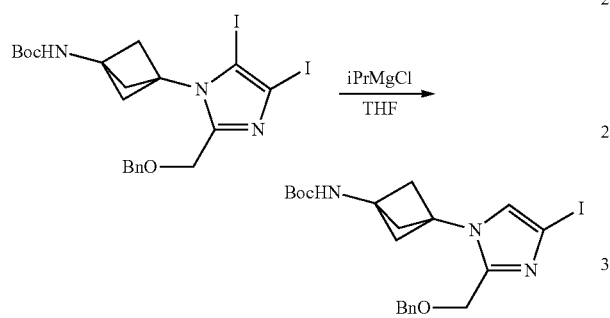

Step 3: tert-butyl(3-(2-((benzyloxy)methyl)-4-iodo-1H-imidazol-1-yl)bicyclo[1.1.1]-pentan-1-yl)carbamate To a mixture of the product from the previous step (7.8 g, 12.56 mmol) in THF (160 mL) at −70° C. was added iPrMgCl (2 M, 8.79 mL) dropwise and the mixture was stirred at −70° C. for 2 h. The reaction mixture was poured into NH₄Cl (sat aq, 400 mL) and extracted with EtOAc (3×200 mL). The combined organic layers were washed with brine (500 mL), dried over Na₂SO₄, filtered. The filtrate was concentrated under reduced pressure to afford the title compound (6.12 g, 12.35 mmol, 98.40% yield) as a white solid. ¹H NMR (400 MHz, CDCl₃) δ 7.38-7.28 (m, 5H), 6.97 (s, 1H), 5.05 (brs, 1H), 4.59 (s, 2H), 4.49 (s, 2H), 2.52 (brs, 6H), 1.45 (s, 9H).

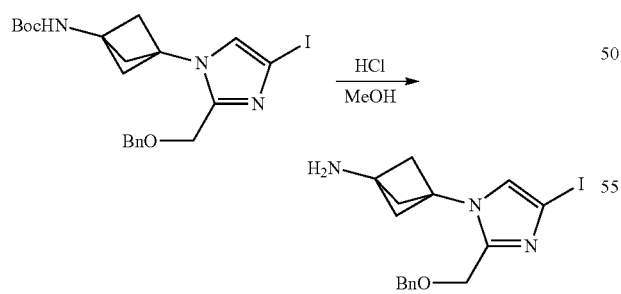

Step 4: 3-(2-((benzyloxy)methyl)-4-iodo-1H-imidazol-1-yl)bicyclo[1.1.1]pentan-1-amine To a solution of the product from the previous step (7.7 g, 15.54 mmol) in anhydrous MeOH (70 mL) was added HCl/MeOH (4 M, 70 mL) and the resulting mixture was stirred at 20° C. for 4 h. The reaction was concentrated. The residue was poured into NaHCO₃ (sat. aq, 200 mL) and the resulting mixture was extracted with EtOAc (200 mL×3). The combined organic layers were washed by brine (400 mL), dried over Na₂SO₄, filtered and concentrated to afford the title compound (6 g, 15.18 mmol, 97.66% yield) as a yellow oil. ¹H NMR (400 MHz, CDCl₃) δ 7.40-7.20 (m, 5H), 6.96 (s, 1H), 4.58 (s, 2H), 4.48 (s, 2H), 2.31 (s, 6H).

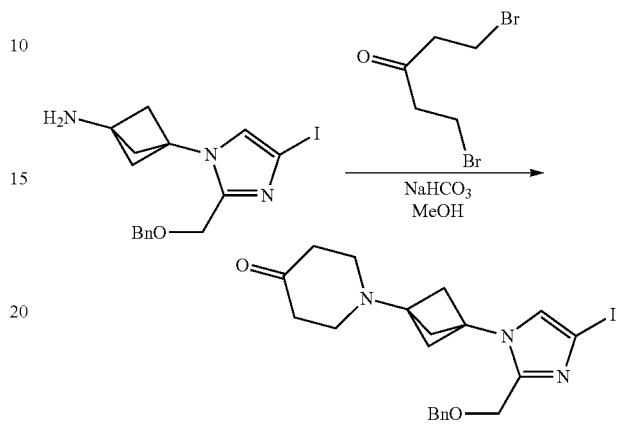

Step 5: 1-(3-(2-((benzyloxy)methyl)-4-iodo-1H-imidazol-1-yl)bicyclo[1.1.1]pentan-1-yl)piperidin-4-one To a mixture of the product from the previous step (2.2 g, 5.57 mmol) and NaHCO₃ (2.34 g, 27.83 mmol) in MeOH (110 mL) was added 1,5-dibromopentan-3-one (2.72 g, 11.13 mmol) in MeOH (11 mL) dropwise and the resulting mixture was heated to 60° C. for 1 h. The reaction mixture was filtered. The filtrate was concentrated under reduced pressure. The residue was purified by silica gel chromatography (Petroleum ether/EtOAc=1/1) to afford a first batch of the title compound (4.1 g, 8.59 mmol, 51.44% yield) as a yellow solid and a second batch of the title compound (700 mg, 1.04 mmol, 6.24% yield, 71% purity) as a yellow oil. ¹H NMR (400 MHz, CDCl₃) δ 7.35-7.28 (m, 5H), 6.99 (s, 1H), 4.60 (s, 2H), 4.49 (s, 2H), 2.79 (t, J=6.2 Hz, 4H), 2.49 (t, J=6.2 Hz, 4H), 2.32 (s, 6H).

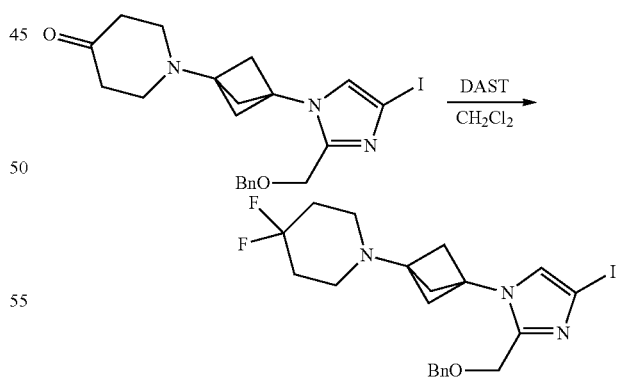

Step 6: 1-(3-(2-((benzyloxy)methyl)-4-iodo-1H-imidazol-1-yl)bicyclo[1.1.1]pentan-1-yl)-4,4-difluoropiperidine (Intermediate VI) To a solution of the product from the previous step (2 g, 4.19 mmol) in CH₂Cl₂ (40 mL) was added DAST (1.42 g, 8.80 mmol, 1.16 mL) and the resulting mixture was stirred vigorously at 20° C. for 0.5 h. The reaction mixture was poured into water (100 mL) and extracted with CH₂Cl₂ (3×50 mL). The combined organic layers were washed with brine (100 mL), dried over Na₂SO₄, and filtered. The filtrate was concentrated under reduced pressure. The residue was purified by silica gel column (Petroleum ether/EtOAc=5/1-1/1) to afford the title compound (1.53 g, 3.06 mmol, 73.13% yield) as a white solid. ¹H NMR (400 MHz, CDCl₃) δ 7.38-7.28 (m, 5H), 6.99 (s, 1H), 4.59 (s, 2H), 4.49 (s, 2H), 2.63-2.59 (m, 4H), 2.28 (s, 6H), 2.09-1.97 (m, 4H).

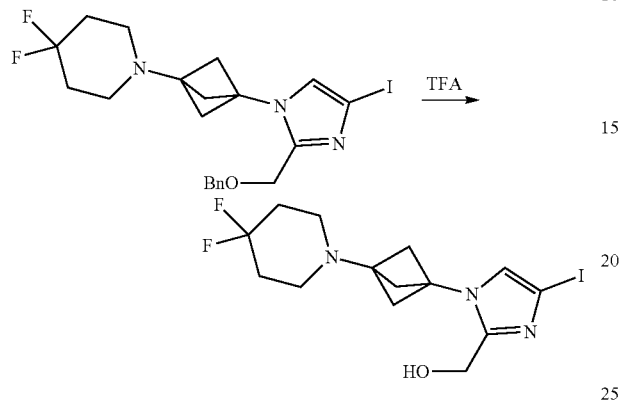

Step 7: (1-(3-(4,4-difluoropiperidin-1-yl)bicyclo[1.1.1]pentan-1-yl)-4-iodo-1H-imidazol-2-yl)methanol A mixture of Intermediate VI (3.4 g, 6.81 mmol) in TFA (34 mL) was stirred at 90° C. for 16 h. The reaction mixture was combined with another batch (11.7 g scale). The combined mixture was concentrated in vacuum. The residue was quenched with NaHCO₃ (sat. aq, 220 mL) and extracted with EtOAc (220 mL×3). The combined organic layers were dried over Na₂SO₄, filtered and concentrated in vacuum to afford crude product. The crude product was triturated by MTBE (140 mL) and filtered. The cake was dried in vacuum to afford a first batch of the title compound (8.2 g, 89% purity) as a yellow solid. The filtrate was concentrated and purified by column chromatography (SiO₂, CH₂Cl₂/MeOH=1/0-10/1) to afford a second batch of the title compound (3.6 g, 80% purity) as a yellow solid. MS (ES⁺) $C_{14}H_{18}F_2IN_3O$ requires: 409, found: 410 [M+H]⁺.

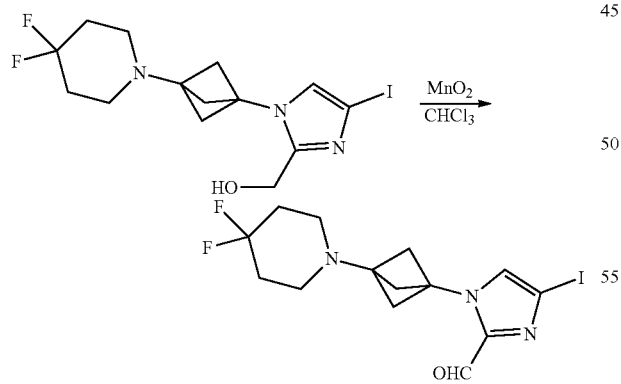

Step 8: 1-(3-(4,4-difluoropiperidin-1-yl)bicyclo[1.1.]pentan-1-yl)-4-iodo-1H-imidazole-2-carbaldehyde To a mixture of the product from the previous step (5 g, 12.22 mmol) in CHCl₃ (80 mL) was added MnO₂ (15.93 g, 183.28 mmol) and the resulting mixture was stirred at 50° C. for 16 h. The reaction mixture was filtered. The cake was washed sequentially with THF (25 mL×2), CH₂Cl₂ (50 mL×2), and EtOAc (50 mL×2). The filtrate was concentrated in vacuum to afford the title compound (4.44 g, 10.90 mmol, 89.24% yield) as a yellow solid. MS (ES⁺) $C_{14}H_{16}F_2IN_3O$ requires: 407, found: 408 [M+H]⁺. ¹H NMR (400 MHz, CDCl₃) δ 9.70 (s, 1H), 7.17 (d, J=0.7 Hz, 1H), 2.65 (t, J=5.7 Hz, 4H), 2.41 (s, 6H), 2.11-1.97 (m, 4H).

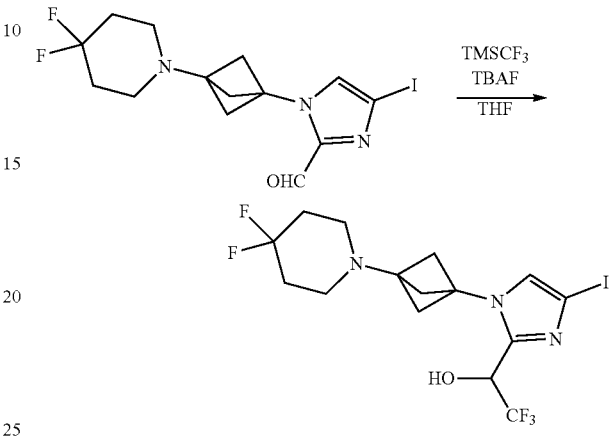

Step 9: 1-(1-(3-(4,4-difluoropiperidin-1-yl)bicyclo[1.1.1]pentan-1-yl)-4-iodo-1H-imidazol-2-yl)-2,2,2-trifluoroethanol (Intermediate VII) Two batches of the following reaction were run in parallel. To a solution of the product from the previous step (2.5 g, 6.14 mmol) in THF (150 mL) was added a solution of TMSCF₃ (10.48 g, 73.67 mmol) in THF (100 mL) dropwise at −20° C. for 1 h under N₂, after stirring for 10 min, TBAF (1 M, 73.67 mL) was added dropwise at −20° C. for 1 h under N₂ and the resulting mixture was stirred at −20° C. for 0.5 h. The two batches of reaction mixture was quenched with NH₄Cl (sat. aq, 1000 mL) and extracted with EtOAc (1000 mL×3). The organic layer was washed with NH₄Cl (sat. aq, 1000 mL×3). The organic layer was dried over Na₂SO₄, filtered and concentrated. The residue was purified by column chromatography (SiO₂, Petroleum ether/EtOAc=10/1-3/1) to afford the title compound (4.14 g, 8.68 mmol, 70.65% yield) as a yellow solid. MS (ES⁺) $C_{15}H_{17}F_5IN_3O$ requires: 477, found: 478 [M+H]⁺.

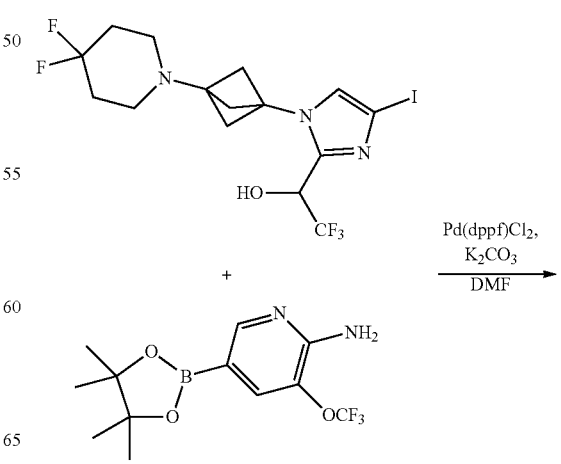

-continued

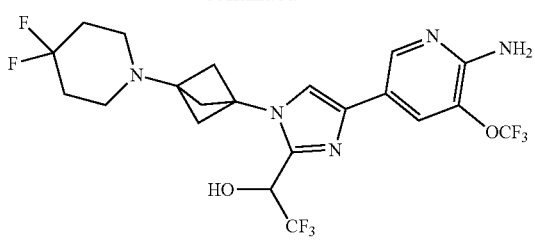

Step 10: 1-(4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)-2,2,2-trifluoroethanol A mixture of the product from the previous step (3 g, 6.29 mmol), 5-(4,4,5,5-tetramethyl-1,3,2-dioxaborolan-2-yl)-3-(trifluoromethoxy)pyridin-2-amine (2.56 g, 8.42 mmol), Pd(dppf)Cl$_2$ (689.99 mg, 942.98 mol), and K$_2$CO$_3$ (2 M, 10.47 mL) in DMF (50 mL) was degassed and purged with N$_2$ for 3 times and the resulting mixture was stirred at 90° C. for 1 hr under N$_2$ atmosphere. This reaction mixture was diluted with H$_2$O (60 mL) and extracted with EtOAc (60 mL×3). The combined organic layers were washed with brine (60×3), dried over Na$_2$SO$_4$, and filtered. The filtrate was concentrated in vacuum. The residue was purified by column chromatography (SiO$_2$, Petroleum ether/EtOAc=8/1-1/1) followed by prep-HPLC (column: Phenomenex luna C18 150 mm*40 mm*15 μm; mobile phase: [water (0.225% FA)-ACN]; B %: 25%-55%, 9 min) to afford the title compound (1.8 g, 3.34 mmol, 53.20% yield, 98% purity) as a white solid. MS (ES$^+$) C$_{21}$H$_{21}$F$_8$N$_5$O$_2$ requires: 527, found: 528 [M+H]$^+$.

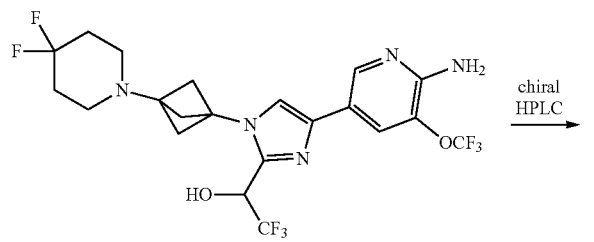

Step 11: (S)-1-(4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)-2,2,2-trifluoroethanol and (R)-1-(4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)-2,2,2-trifluoroethanol (Examples 9a and 9b)

The racemic title compound (1.8 g) was separated by chiral HPLC (column: DAICEL CHIRALCEL OJ-H (250 mm*30 mm*5 m); mobile phase: [0.1% NH$_4$OH/EtOH]; B %: 20%-20%, 4.95 min; 149 min) to afford two enantiomers of undetermined absolute stereochemistry.

Example 9a was obtained as a white solid 687.4 mg, 1.26 mmol, 36.92% yield, 97% purity); retention time=0.878 (column: Chiralcel OJ-3 50 mm*4.6 mm*3 μm; mobile phase: Phase A for CO$_2$, and Phase B for EtOH (0.05% DEA); gradient elution: EtOH (0.05% DEA) in CO$_2$ from 5% to 40%; flow rate: 3 mL/min; Detector: PDA; column temp: 35° C.; back pressure: 100 bar).

MS (ES$^+$) C$_{21}$H$_{21}$F$_8$N$_5$O$_2$ requires: 527, found: 528 [M+H]$^+$.

$^1$H NMR (400 MHz, CDCl$_3$) δ 8.36 (d, J=2.0 Hz, 1H), 7.77 (d, J=1.6 Hz, 1H), 7.12 (s, 1H), 5.11 (br s, 1H), 4.79 (s, 2H), 4.37 (br s, 1H), 2.66 (t, J=5.6 Hz, 4H), 2.44-2.34 (m, 6H), 2.13-2.00 (m, 4H).

Example 9b was obtained as a white solid (697.2 mg, 1.31 mmol, 38.38% yield, 99% purity); retention time=1.150 (column: Chiralcel OJ-3 50 mm*4.6 mm*3 μm; mobile phase: Phase A for CO$_2$, and Phase B for EtOH (0.05% DEA); gradient elution: EtOH (0.05% DEA) in CO$_2$ from 5% to 40%; flow rate: 3 mL/min; Detector: PDA; column temp: 35° C.; back pressure: 100 bar).

MS (ES$^+$) C$_{21}$H$_{21}$F$_8$N$_5$O$_2$ requires: 527, found: 528 [M+H]$^+$.

$^1$H NMR (400 MHz, CDCl$_3$) δ 8.37 (d, J=1.6 Hz, 1H), 7.79-7.66 (m, 1H), 7.09 (s, 1H), 5.33 (br s, 1H), 5.14 (br d, J=5.0 Hz, 1H), 4.94 (s, 2H), 2.65 (br t, J=5.6 Hz, 4H), 2.43-2.34 (m, 6H), 2.12-1.99 (m, 4H).

Examples 10a and 10b

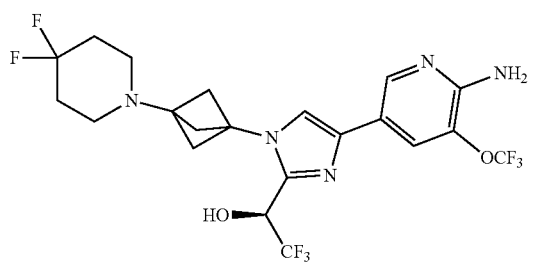

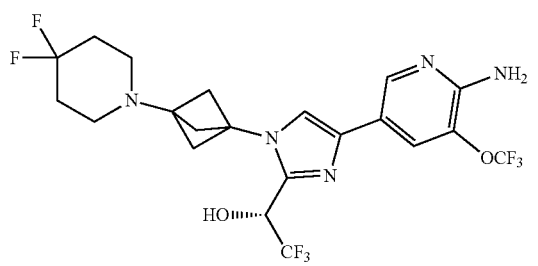
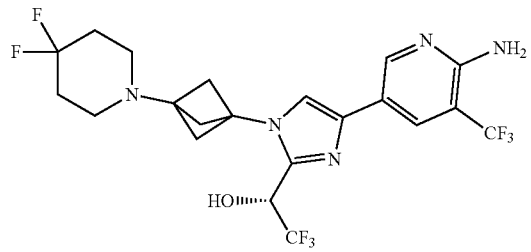 [SMILES: Nc1ncc(-c2cn(C34CC(N5CCC(F)(F)CC5)(C3)C4)c([C@@H](O)C(F)(F)F)n2)cc1C(F)(F)F]

(R)-1-(4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)-2,2,2-trifluoroethanol and

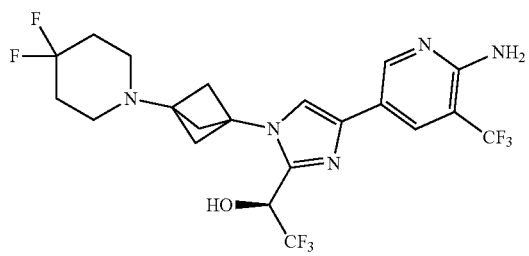 [SMILES: Nc1ncc(-c2cn(C34CC(N5CCC(F)(F)CC5)(C3)C4)c([C@H](O)C(F)(F)F)n2)cc1C(F)(F)F]

(S)-1-(4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)-2,2,2-trifluoroethanol

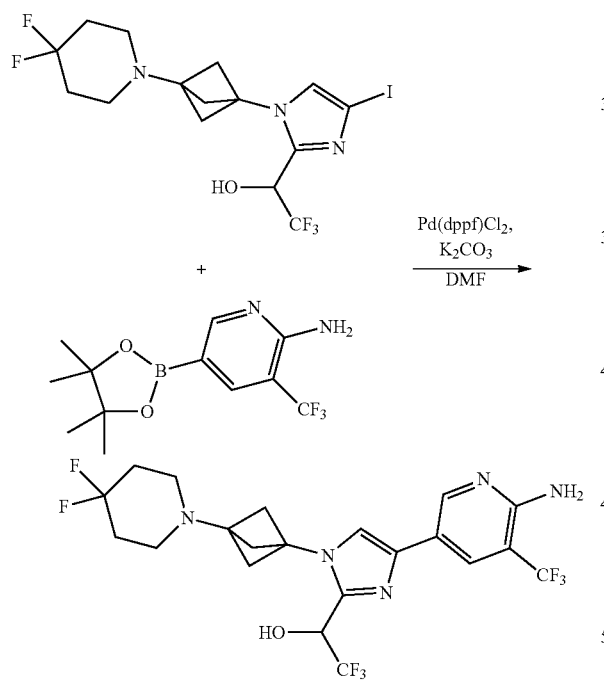

Step 1: 1-(4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)-2,2,2-trifluoroethanol A mixture of Intermediate VII (2 g, 4.19 mmol), 5-(4,4,5,5-tetramethyl-1,3,2-dioxaborolan-2-yl)-3-(trifluoromethyl)pyridin-2-amine (1.62 g, 5.62 mmol), Pd(dppf)Cl$_2$ (459.99 mg, 628.65 μmol), and K$_2$CO$_3$ (2 M, 6.98 mL) in DMF (60 mL) was degassed and purged with N$_2$ for 3 times and the resulting mixture was stirred at 90° C. for 1 hr under N$_2$ atmosphere. The reaction mixture was combined with another batch (1 g scale), diluted with H$_2$O (50 mL), and extracted with EtOAc (30 mL×3). The combined organic layers were washed with brine (45 mL×2), dried over Na$_2$SO$_4$, filtered and concentrated. The residue was purified by column chromatography (SiO$_2$, Petroleum ether/EtOAc=2/1-1/2) followed by prep-HPLC (column: Phenomenex luna C18 150*40 mm*15 μm; mobile phase: [water (0.225% FA)-ACN]; B %: 24%-54%, 9 min) to afford a first batch of the title compound (908 mg, 1.72 mmol, 41.09% yield, 97% purity) as a white solid and a second batch (293 mg, 472.20 μmol, 11.27% yield, 80% purity) as a yellow solid. MS (ES$^+$) C$_{21}$H$_{21}$F$_8$N$_5$O requires: 511, found: 512 [M+H]$^+$.

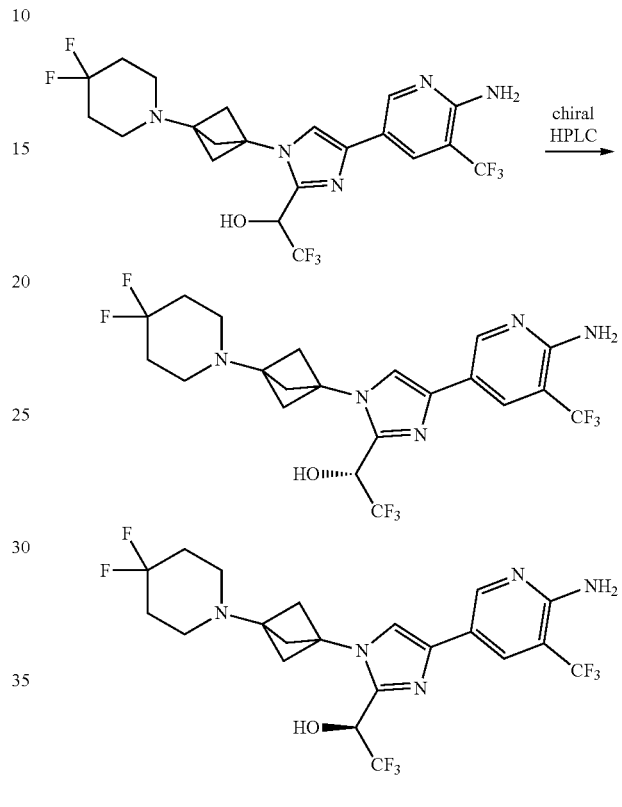

Step 2: (R)-1-(4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)-2,2,2-trifluoroethanol and (S)-1-(4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)-2,2,2-trifluoroethanol (Examples 10a and 10b)

The racemic title compound (1.3 g) was separated by chiral HPLC (column: DAICEL CHIRALPAK AD-H (250 mm*30 mm*5 m); mobile phase: [0.1% NH$_4$OH/EtOH]; B %: 25%-25%, 2.2 min; 380 min) to afford two enantiomers of undetermined absolute stereochemistry.

Example 10a: was obtained as a white solid (602.4 mg, 1.17 mmol, 45.88% yield, 99% purity); retention time=1.237 (column: Chiralpak AD-3 50 mm*4.6 mm*3 μm; mobile phase: Phase A for CO$_2$, and Phase B for IPA (0.05% DEA); gradient elution: IPA (0.05% DEA) in CO$_2$ from 5% to 40%; flow rate: 3 mL/min; Detector: PDA; column temp: 35° C.; back pressure: 100 bar).

MS (ES$^+$) C$_{21}$H$_{21}$F$_8$N$_5$O requires: 511, found: 512 [M+H]$^+$.

$^1$H NMR (400 MHz, CDCl$_3$) δ 8.58 (d, J=1.6 Hz, 1H), 8.07 (d, J=2.0 Hz, 1H), 7.14 (s, 1H), 5.12 (br s, 1H), 5.02 (s, 2H), 4.36 (br d, J=7.0 Hz, 1H), 2.66 (t, J=5.6 Hz, 4H), 2.44-2.34 (m, 6H), 2.12-2.00 (m, 4H).

Example 10b was obtained as a white solid (566.1 mg, 1.11 mmol, 43.55% yield, 100% purity); retention time=1.399 (column: Chiralpak AD-3 50 mm*4.6 mm*3 μm; mobile phase: Phase A for $CO_2$, and Phase B for IPA (0.05% DEA); gradient elution: IPA (0.05% DEA) in $CO_2$ from 5% to 40%; flow rate: 3 mL/min; Detector: PDA; column temp: 35° C.; back pressure: 100 bar).

MS (ES$^+$) $C_{21}H_{21}F_8N_5O$ requires: 511, found: 512 [M+H]$^+$.

$^1$H NMR (400 MHz, CDCl$_3$) δ 8.58 (d, J=1.6 Hz, 1H), 8.07 (d, J=2.0 Hz, 1H), 7.14 (s, 1H), 5.12 (br s, 1H), 5.02 (s, 2H), 4.36 (br d, J=7.0 Hz, 1H), 2.66 (t, J=5.6 Hz, 4H), 2.41-2.36 (m, 6H), 2.11-2.00 (m, 4H).

Example 11

(4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)(cyclopropyl)methanol (IACS-071089)

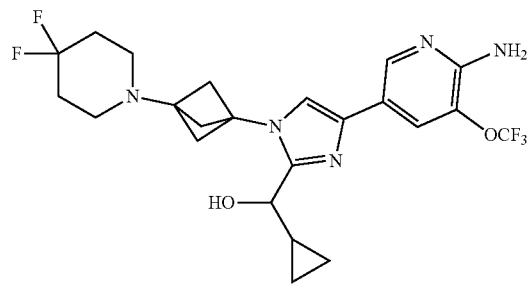 [SMILES: Nc1ncc(-c2cn(C34CC(N5CCC(F)(F)CC5)(C3)C4)c(C(O)C3CC3)n2)cc1OC(F)(F)F]

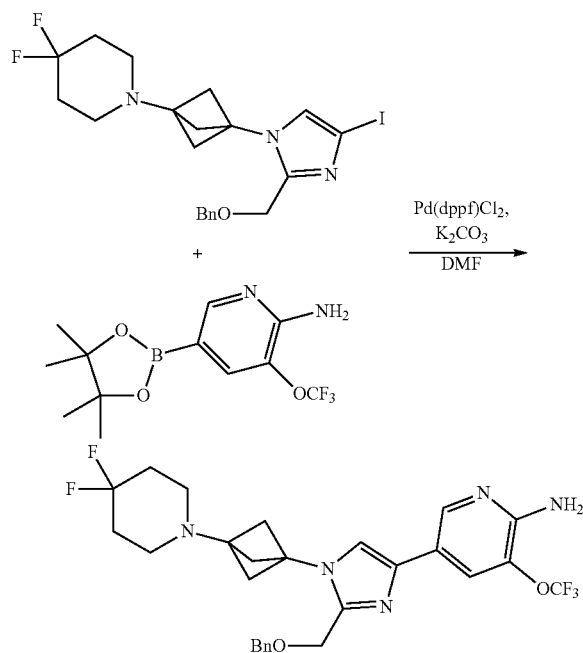

Step 1: 5-(2-((benzyloxy)methyl)-1-(3-(4,4-difluoropiperidin-1-yl)bicyclo[1.1.1]-pentan-1-yl)-1H-imidazol-4-yl)-3-(trifluoromethoxy)pyridin-2-amine To a mixture of Intermediate VI (1 g, 2.00 mmol) and 5-(4,4,5,5-tetramethyl-1,3,2-dioxaborolan-2-yl)-3-(trifluoromethoxy)pyridin-2-amine (791.64 mg, 2.60 mmol) in DMF (30 mL) was added Pd(dppf)Cl$_2$ (250.00 mg, 341.67 μmol) and K$_2$CO$_3$ (2 M, 3.30 mL) under N$_2$. The mixture was heated to 90° C. for 0.5 h. The reaction mixture was poured into water (100 mL) and extracted with EtOAc (3×50 mL). The combined organic layers were washed with CaCl$_2$ (sat. aq, 100 mL), dried over Na$_2$SO$_4$, filtered, and concentrated under reduced pressure. The residue was purified by silica gel column (Petroleum ether/EtOAc=1/1-0/1) to afford the title compound (0.9 g, 1.47 mmol, 73.60% yield, 90% purity) as a yellow solid.

MS (ES$^+$) $C_{27}H_{28}F_5N_5O_2$ requires: 549, found: 550 [M+H]$^+$.

$^1$H NMR (400 MHz, CDCl$_3$) δ 8.35 (s, 1H), 7.80 (s, 1H), 7.39-7.29 (m, 5H), 7.08 (s, 1H), 4.73 (s, 2H), 4.65 (s, 2H), 4.55 (s, 2H), 2.62 (br t, J=5.6 Hz, 4H), 2.33 (s, 6H), 2.13-1.98 (m, 4H).

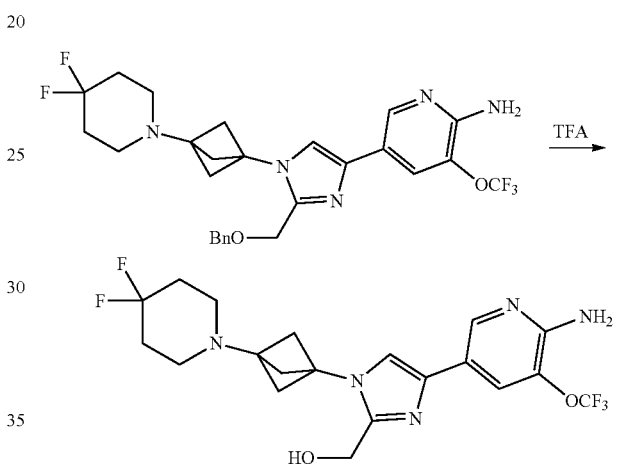

Step 2: (4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)methanol A mixture of the product from the previous step (900 mg, 1.64 mmol) in TFA (8 mL) was stirred at 90° C. for 12 h, then concentrated under reduced pressure. The residue was diluted with NaHCO$_3$ (sat. aq, 50 mL) and extracted with EtOAc (50 mL×3). The organic layer was washed with brine (100 mL), dried over Na$_2$SO$_4$, and filtered. The filtrate was concentrated and purified by silica gel column (EtOAc/Methanol=100/1-20/1) to afford the title compound (550 mg, 1.10 mmol, 67.25% yield, 92% purity) as gray solid.

MS (ES$^+$) $C_{20}H_{22}F_5N_5O_2$ requires: 459, found: 460 [M+H]$^+$.

$^1$H NMR (400 MHz, CDCl$_3$) δ 8.31 (d, J=1.2 Hz, 1H), 7.77 (s, 1H), 7.04 (s, 1H), 4.85 (s, 2H), 4.72 (s, 2H), 2.66 (t, J=5.6 Hz, 4H), 2.38 (s, 6H), 2.12-1.96 (m, 4H)

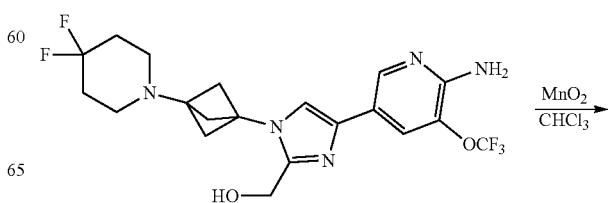

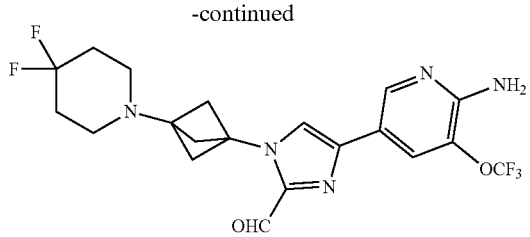

Step 3: 4-(6-amino-5-(trifluoromethoxy)pyridin-3-yl)-1-(3-(4,4-difluoropiperidin-1-yl)bicyclo[1.1.1]pentan-1-yl)-1H-imidazole-2-carbaldehyde To the solution of the product from the previous step (150 mg, 326.50 µmol) in CHCl₃ (5 mL) was added MnO₂ (283.85 mg, 3.27 mmol) and the resulting mixture was stirred at 50° C. for 48 h. The reaction mixture was filtered, and the filtrate was concentrated under reduced pressure. The residue was purified by prep-TLC (Petroleum ether/EtOAc=1/1) to afford the title compound (65 mg, 103.74 µmol, 31.77% yield, 73% purity) as a yellow solid.

MS (ES⁺) $C_{20}H_{20}F_5N_5O_2$ requires: 457, found: 458 [M+H]⁺.

¹H NMR (400 MHz, CDCl₃) δ 9.81 (s, 1H), 8.39 (d, J=1.6 Hz, 1H), 7.88 (s, 1H), 7.29 (s, 1H), 4.88 (s, 2H), 2.68 (t, J=5.6 Hz, 4H), 2.47 (s, 6H), 2.17-1.96 (m, 4H).

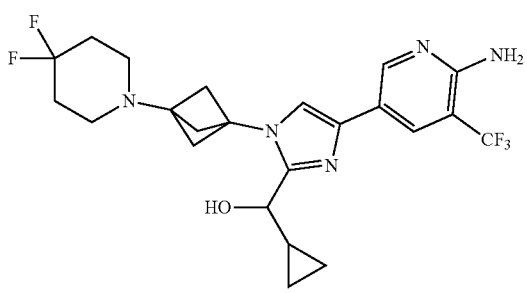 [SMILES: Nc1ncc(-c2cn(C34CC(N5CCC(F)(F)CC5)(C3)C4)c(C(O)C3CC3)n2)cc1C(F)(F)F]

Step 4: (4-(6-amino-5-(trifluoromethoxy)pyridin-3-yl)-1-(3-(4,4-difluoropiperidin-1-yl)bicyclo[1.1.1]pentan-1-yl)-1H-imidazol-2-yl)(cyclopropyl)methanol (Example 11) To a solution of the product from the previous step (30 mg, 65.59 µmol) in THF (1.5 mL) was added cyclopropylmagnesium bromide (0.5 M, 1.31 mL) at −70° C. under N₂ and the resulting mixture was stirred at −70° C. for 1 hr, then the mixture was stirred at 20° C. for 1 h. The reaction mixture was quenched with NH₄Cl (sat. aq, 10 mL) and extracted with EtOAc (3×10 mL). The combined organic layers were washed with brine (20 mL), dried over Na₂SO₄, and filtered. The filtrate was concentrated under reduced pressure. The residue was purified by prep-TLC (EtOAc/Petroleum ether=2/1) followed by prep-HPLC (column: Phenomenex Synergi C18 150 mm*25 mm*10 µm; mobile phase: [water (0.225% FA)-ACN]; B %: 16%-40%, 8 min) to afford Example 11 (5.1 mg, 10.01 µmol, 15.26% yield, 98% purity) as a white solid.

MS (ES⁺) $C_{23}H_{26}F_5N_5O_2$ requires: 499, found: 500 [M+H]⁺.

¹H NMR (400 MHz, MeOD) δ 8.31 (d, J=2.0 Hz, 1H), 7.92-7.86 (d, J=1.6 Hz, 1H), 7.41 (s, 1H), 4.15 (d, J=8.6 Hz, 1H), 2.71 (br t, J=5.6 Hz, 4H), 2.45-2.35 (m, 6H), 2.12-1.94 (m, 4H), 1.74-1.56 (m, 1H), 0.76-0.67 (m, 1H), 0.64-0.55 (m, 1H), 0.52-0.46 (m, 1H), 0.35-0.30 (m, 1H).

Example 12

(4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)(cyclopropyl)methanol

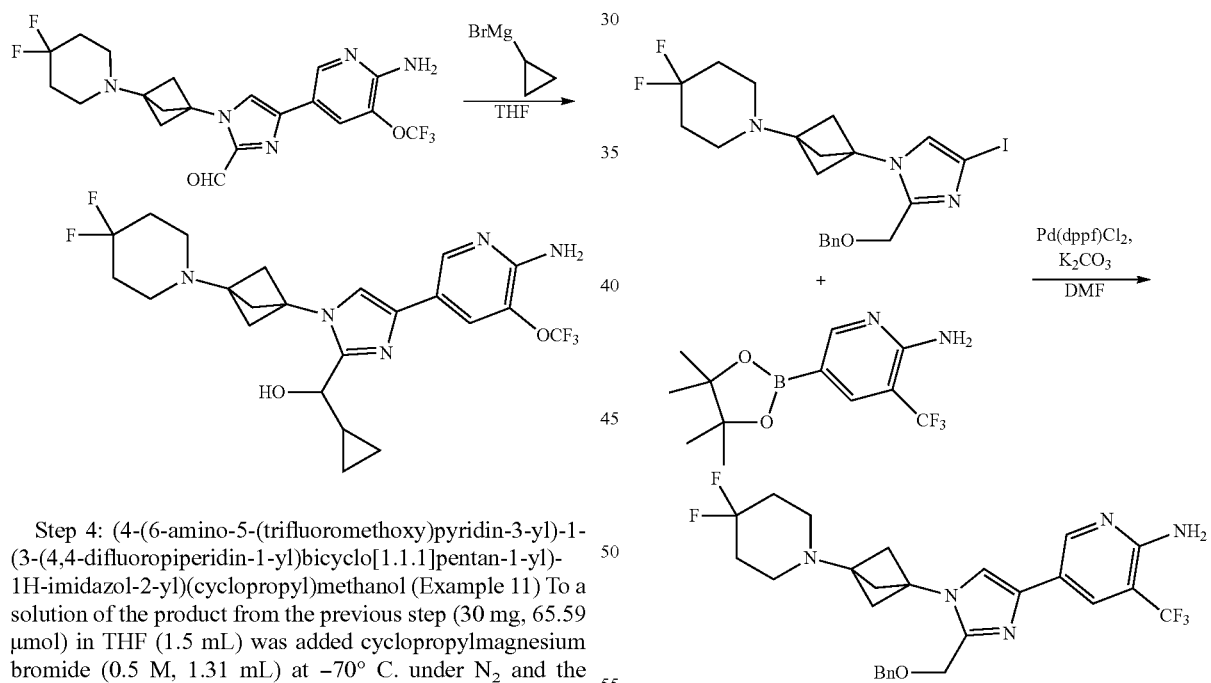

Step 1: 5-(2-((benzyloxy)methyl)-1-(3-(4,4-difluoropiperidin-1-yl)bicyclo-[1.1.1]pentan-1-yl)-1H-imidazol-4-yl)-3-(trifluoromethyl)pyridin-2-amine A mixture of Intermediate VI (900 mg, 1.80 mmol), 5-(4,4,5,5-tetramethyl-1,3,2-dioxaborolan-2-yl)-3-(trifluoromethyl)pyridin-2-amine (674.99 mg, 2.34 mmol), Pd(dppf)Cl₂ (225.00 mg, 307.50 mol), and K₂CO₃ (2 M, 2.97 mL) in DMF (10 mL) was degassed and purged 3 times with N₂, and the resulting mixture was stirred at 90° C. for 1 h. The reaction mixture was diluted with H₂O (20 mL) and extracted with EtOAc (30 mL×3). The combined organic layers were washed with brine (60 mL), dried over Na₂SO₄, and filtered. The filtrate was concentrated under reduced pressure. The residue was purified by column chromatography (SiO₂, Petroleum ether/EtOAc=1/0-1/1) to afford the title compound (1 g, 1.74 mmol, 96.71% yield, 93% purity) as a white solid.

MS (ES⁺) $C_{27}H_{28}F_5N_5O$ requires: 533, found: 534 [M+H]⁺.

¹H NMR (400 MHz, CDCl₃) δ 8.57 (d, J=1.6 Hz, 1H), 8.10 (d, J=2.0 Hz, 1H), 7.39-7.29 (m, 5H), 7.11 (s, 1H), 4.97 (s, 2H), 4.65 (s, 2H), 4.55 (s, 2H), 2.62 (t, J=5.6 Hz, 4H), 2.33 (s, 6H), 2.11-1.99 (m, 4H).

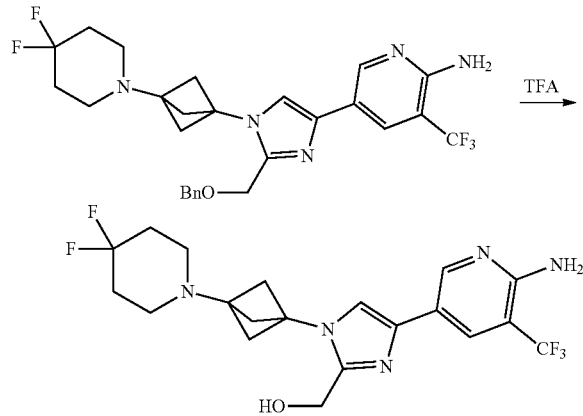

Step 2: (4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)methanol A mixture of the product from the previous step (900 mg, 1.57 mmol) in TFA (10 mL) was stirred at 90° C. for 12 h. The reaction mixture was cooled to room temperature and concentrated under reduced pressure. The residue was diluted with NaHCO₃ (10 mL) and extracted with EtOAc (15 mL×3). The combined organic layer was dried over Na₂SO₄, filtered and concentrated in vacuum. The residue was purified by column chromatography (SiO₂, Petroleum ether/EtOAc=1/0-0/1) to afford the title compound (670 mg, 1.38 mmol, 87.65% yield, 91% purity) as a yellow solid.

MS (ES⁺) $C_{20}H_{22}F_5N_5O$ requires: 443, found: 444 [M+H]⁺.

¹H NMR (400 MHz, CDCl₃) δ 8.56 (d, J=1.2 Hz, 1H), 8.08 (d, J=1.6 Hz, 1H), 7.08 (s, 1H), 5.01 (s, 2H), 4.75 (s, 2H), 2.66 (t, J=5.8 Hz, 4H), 2.39 (s, 6H), 2.12-2.01 (m, 4H).

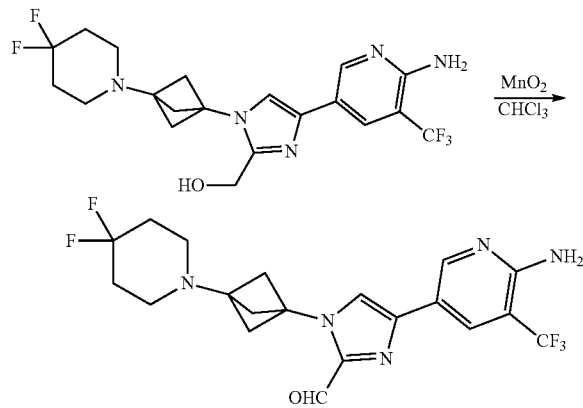

Step 3: 4-(6-amino-5-(trifluoromethyl)pyridin-3-yl)-1-(3-(4,4-difluoropiperidin-1-yl)bicyclo[1.1.1]pentan-1-yl)-1H-imidazole-2-carbaldehyde To a solution of the product from the previous step (600 mg, 1.23 mmol) in CHCl₃ (10 mL) was added MnO₂ (1.18 g, 13.57 mmol) and the resulting mixture was stirred at 50° C. for 12 h. Additional MnO₂ (600 mg) was added and the resulting mixture was stirred at 50° C. for another 12 h. The reaction mixture was filtered. The filtrate was concentrated. The residue was triturated with MTBE (30 mL) and filtered. The filter cake was collected to afford a first batch of the title compound (320 mg, 623.48 µmol, 50.63% yield, 86% purity) as a yellow solid. The filtrate was purified by prep-TLC (EtOAc/CH₂Cl₂/MeOH=20/10/1) to afford a second batch of the title compound (85 mg, 182.94 µmol, 14.86% yield, 95% purity) as a yellow solid.

MS (ES⁺) $C_{20}H_{20}F_5N_5O$ requires: 441, found: 442 [M+H]⁺.

¹H NMR (400 MHz, CDCl₃) δ 9.82 (d, J=0.8 Hz, 1H), 8.63 (d, J=1.6 Hz, 1H), 8.16 (d, J=1.8 Hz, 1H), 7.31 (d, J=0.8 Hz, 1H), 5.06 (s, 2H), 2.76-2.58 (m, 4H), 2.47 (s, 6H), 2.14-1.99 (m, 4H).

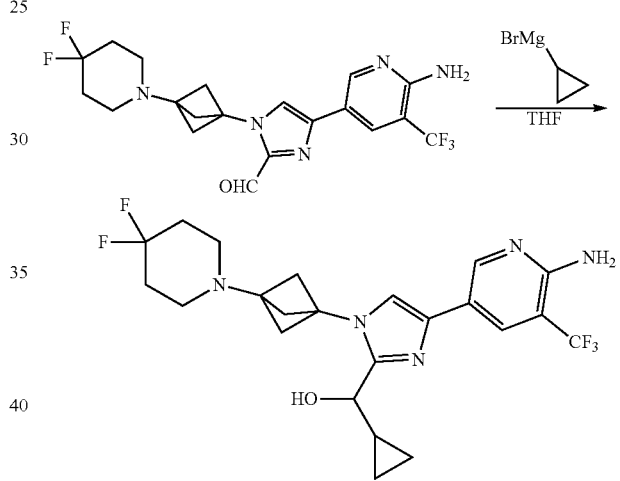

Step 4: (4-(6-amino-5-(trifluoromethyl)pyridin-3-yl)-1-(3-(4,4-difluoropiperidin-1-yl)bicyclo[1.1.1]pentan-1-yl)-1H-imidazol-2-yl)(cyclopropyl)methanol (Example 12) To a solution of the product from the previous step (50 mg, 97.42 µmol) in THF (2.5 mL) was added cyclopropylmagnesium bromide (0.5 M, 3.50 mL) at −78° C. under N₂ and the resulting mixture was stirred at −78° C. for 1 h. The reaction mixture was warmed to 20° C. for 0.5 h. The reaction mixture was combined with another batch (10 mg scale) and quenched with NH₄Cl (sat. aq, 8 mL) at −78° C. The suspension was extracted with EtOAc (100 mL×3). The combined organic layers were washed with brine (50 mL×2), dried over Na₂SO₄, filtered and concentrated in vacuo. The residue was purified by prep-TLC (CH₂Cl₂/EtOAc/Methanol=10/10/1). The crude product was re-purified by prep-HPLC (column: Waters Xbridge 150 mm*25 mm*5 m; mobile phase: [water (10 mM NH₄HCO₃)-ACN]; B %: 27%-57%, 10 min) to afford Example 12 (8.8 mg, 17.11 µmol, 17.56% yield, 94% purity) as a white solid.

MS (ES⁺) $C_{23}H_{26}F_5N_5O$ requires: 483, found: 484 [M+H]⁺.

¹H NMR (400 MHz, MeOD) δ 8.57 (s, 1H), 8.19 (s, 1H), 7.45 (s, 1H), 4.17 (d, J=8.8 Hz, 1H), 2.73 (br t, J=5.6 Hz,

4H), 2.46 (s, 6H), 2.20-1.98 (m, 4H), 1.77-1.60 (m, 1H), 0.80-0.68 (m, 1H), 0.66-0.57 (m, 1H), 0.51 (m, 1H), 0.40-0.28 (m, 1H).

The activity of the compounds in Examples 1-12 as DLK inhibitors is illustrated in the following assays.

Biological Activity Assays

Compounds described herein have been shown to bind DLK in vitro, and to inhibit phosphorylation of a downstream molecular target in a cellular assay.

DLK Kd Determinations

The DLK dissociation constants ($K_d$) have been determined in the KINOMEscan KdELECT Service at DiscoveRx.

A fusion protein of full length of human DLK (amino acids 1-859) and the DNA binding domain of NFkB was expressed in transiently transfected HEK293 cells. From these HEK 293 cells, extracts were prepared in M-PER extraction buffer (Pierce) in the presence of Protease Inhibitor Cocktail Complete (Roche) and Phosphatase Inhibitor Cocktail Set II (Merck) per manufacturers' instructions. The DLK fusion protein was labeled with a chimeric double-stranded DNA tag containing the NFkB binding site (5'-GGGAATTCCC-3', SEQ ID NO:1) fused to an amplicon for qPCR readout, which was added directly to the expression extract (the final concentration of DNA-tag in the binding reaction is 0.1 nM).

Streptavidin-coated magnetic beads (Dynal M280) were treated with a biotinylated small molecule ligand for 30 minutes at room temperature to generate affinity resins the binding assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding.

The binding reaction was assembled by combining 16 µl of DNA-tagged kinase extract, 3.8 µl liganded affinity beads, and 0.18 µl test compound (PBS/0.05% Tween 20/10 mM DTT/0.1% BSA/2 µg/ml sonicated salmon sperm DNA)]. Extracts were used directly in binding assays without any enzyme purification steps at a >10,000-fold overall stock dilution (final DNA-tagged enzyme concentration <0.1 nM). Extracts were loaded with DNA-tag and diluted into the binding reaction in a two step process. First extracts were diluted 1:100 in 1× binding buffer (PBS/0.05% Tween 20/10 mM DTT/0.1% BSA/2 µg/ml sonicated salmon sperm DNA) containing 10 nM DNA-tag. This dilution was allowed to equilibrate at room temperature for 15 minutes and then subsequently diluted 1:100 in 1× binding buffer. Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. All reactions performed in polypropylene 384-well plates. Each was a final volume of 0.02 mL. Assays were incubated with shaking for 1 hour at room temperature. Then the beads were pelleted and washed with wash buffer (1×PBS, 0.05% Tween 20) to remove displaced kinase and test compound. The washed based were re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR. qPCR reactions were assembled by adding 2.5 µL of kinase eluate to 7.5 µL of qPCR master mix containing 0.15 µM amplicon primers and 0.15 µM amplicon probe. The qPCR protocol consisted of a 10 minute hot start at 95° C., followed by 35 cycles of 95° C. for 15 seconds, 60° C. for 1 minute.

Test compound Handling. Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. The $K_d$s were determined using a compound top concentration of 30,000 nM. $K_d$ measurements were performed in duplicate.

Binding Constant($K_d$) calculation. Binding constants ($K_d$s) were calculated with a standard dose-response curve using the Hill equation:

$$\text{Response} = \text{Background} + \frac{(\text{Signal} - \text{Background})}{\left(1 + \left(\frac{Kd^{Hill\ Slope}}{\text{Dose}^{Hill\ Slope}}\right)\right)}$$

The Hill Slope was set to −1. Curves were fitted using a non-linear least square fit with the Levenberg-Marquardt algorithm (Levenberg, K., A method for the solution of certain non-linear problems in least squares, Q. Appl. Math. 2, 164-168 (1944)). See also Fabian, M. A. et al. A small molecule-kinase interaction map for clinical kinase inhibitors. Nat. Biotechnol. 23, 329-336 (2005); Wodicka, L. M. et al. Activation state-dependent binding of small molecule kinase inhibitors: structural insights from biochemistry. Chem Biol. 17, 1241-9 (2010).

Compounds with lower dissociation constants bind with more affinity to the target. Compounds disclosed herein, particularly (but not exclusively) those with with lower dissociation constants, can be expected to inhibit target activity and to be useful in the treatment of DLK-mediated disease.

Phospho-cJun Cellular Assay

HEK293 cells stably transfected with a Dox-inducible human DLK were plated into a 384-well plate in 20 µl (400,000 cells/well) of DMEM medium (without phenol red) containing 10% fetal bovine serum, 1.5 µg/ml doxycycline and 1 µg/ml puromycin. The cells as negative control were grown in the absence of doxycycline. The plate was incubated at 37° C., 5% $CO_2$ for 20 h, before DMSO (control) or compounds diluted in medium were added. The cells were incubated at 37° C. for an additional 5 h, followed by lysis and the addition detection antibodies from p-cJun (Ser63) cellular assay kit (Cisbio) per manufacturer protocol. The standard dose response curves were fitted by Genedata Screener software using the variable-slope model: $\text{Signal} = \text{Signal}_{negative\ control} + (\text{Signal}_{DMSO\ control} - \text{Signal}_{negative\ control})/(1+(IC_{50}/\text{Dose})^{\text{Hill slope}})$. Only signal and dose in the equation were treated as known values.

For comparison, data for DLK inhibitors 13, 14, 14b, 15, and 16 are included with the pharmacokinetic and pharmacodynamic disclosure below. Synthesis of the compounds is disclosed in the WIPO publication WO2018107072A1, with 13, 14, 15, and 16 corresponding to 63b, 59, 7a, and 8a, respectively in the aforementioned publication.

TABLE 1

Additional DLK inhibitors

| 13 | (R)-1-(4-(6-amino-5-(trifluoromethoxy)-pyridin-3-yl)-1-(bicyclo[1.1.1]pentan-1-yl)-1H-imidazol-2-yl)-2,2,2-trifluoroethan-1-ol |
| 14 | 1-(4-(6-amino-5-(trifluoromethyl)pyridin-3-yl)-1-(bicyclo[1.1.1]pentan-1-yl)-1H-imidazol-2-yl)-2-methylpropan-1-ol |
| 14b | (S)-1-(4-(6-amino-5-(trifluoromethyl)pyridin-3-yl)-1-(bicyclo[1.1.1]pentan-1-yl)-1H-imidazol-2-yl)-2-methylpropan-1-ol |
| 15 | (S)-1-(4-(6-amino-5-(trifluoromethoxy)pyridin-3-yl)-1-(3-morpholinobicyclo[1.1.1]pentan-1-yl)-1H-imidazol-2-yl)-2-methylpropan-1-ol |
| 16 | (R)-1-(4-(6-amino-5-(trifluoromethoxy)pyridin-3-yl)-1-(3-morpholinobicyclo[1.1.1]pentan-1-yl)-1H-imidazol-2-yl)-2,2,2-trifluoroethan-1-ol |

TABLE 2

DLK activity

| Ex. | Kd, nM | Cell IC50 |
|---|---|---|
| 1a | 2.2 | 104.87 |
| 1b | 120 | 938.5 |
| 2a | 4.4 | 126.69 |
| 2b | ND | 1058.5 |
| 3a | ND | 1118 |
| 3b | 0.24 | 26.26 |
| 4a | ND | 1595.50 |
| 4b | 0.29 | 25.26 |
| 5 | 5.2 | 247.8 |
| 6 | 7.7 | 272.5 |
| 7a | 0.21 | 25.655 |
| 7b | ND | 925.7 |

TABLE 2-continued

DLK activity

| Ex. | Kd, nM | Cell IC50 |
|---|---|---|
| 8a | 0.5 | 26.83 |
| 8b | ND | 624.05 |
| 9a | ND | 837.35 |
| 9b | 1 | 42.78 |
| 10a | 0.62 | 64.67 |
| 10b | ND | 1328.5 |
| 11 | 3.1 | 198.4 |
| 12 | 2.9 | 110.26 |
| 13 | 1.6 | 43.6 |
| 14 | 0.3 | 20.9 |
| 14b | 0.12 | ND |
| 15 | 0.29 | 21 |
| 16 | 0.36 | 25 |

Metabolic Stability in Liver Microsome Preparations

The test compound was incubated with liver microsomes (0.5 mg/mL) from CD-1 mouse, Sprague Dawley rat, Beagle dog, Cynomolgus monkey, and human in the presence of NADPH for 45 minutes at 37° C. The % parent remaining over time was determined by LC-MS/MS, using peak area ratios. Half-life ($t_{1/2}$) was calculated using the following equation: $t_{1/2}$=ln2/k, where k is the rate constant of parent decay over time (slope of the plot of log[% parent remaining] versus time).

TABLE 3

Observed Half-Lives in Various Animal Liver Microsomes.

| Half-life in liver microsomes ($t_{1/2}$, minutes) | 13 | 1a | 8a | 9b | 14 | 14b | 4b | 7a | 15 | 16 |
|---|---|---|---|---|---|---|---|---|---|---|
| Mouse | 221 | 378 | 322 | 240 | ND | 16 | 71 | ND | 1842 | 1045 |
| Rat | 77 | 154 | 201 | 581 | 27 | 23 | 30 | 566 | 2998 | 1498 |
| Dog | 109 | 287 | ND | 240 | ND | 154 | 355 | ND | ND | ND |
| Monkey | 56 | 182 | ND | 331 | ND | 7 | 22 | ND | ND | ND |
| Human | 121 | 558 | 297 | 297 | 41 | 26 | 213 | 70 | 80 | 260 |

The instant compounds in this invention show unexpected improvements in in vitro microsomal stability relative to the compounds disclosed in WO2018207072. As shown above in Table 3, addition of a fluorine (examples 1a and 4b) or a 4,4'-difluoropiperidine (example 9b) to the bicyclo[1.1.1]pentane moiety of comparator compounds 13 or 14/14b results in improvements to microsomal stability (compare 1a and 9b to 13; compare 4b to 14/14b). While the compounds corresponding to examples 15 and 16 from WO2018207072, which possess a morpholine-substituted bicyclo[1.1.1]pentane, also show improved microsomal stability, these examples have other liabilities that are addressed by the instant compounds in this new invention, as described in the next section and Table 5.

Pharmacokinetics

Pharmacokinetics for compounds 13, 1a, and 9b were determined using single dosage of Wistar Han rats using techniques that are well known in the art. Clearance, $V_{ss}$ and $t_{1/2}$ values were determined from an IV dose (1 mg/kg), formulated in 20% DMSO+60% PEG400+20% water. $C_{max}$, $AUC_{last}$ and % F values were determined from an oral dose (3 mg/kg), formulated in 0.5% aqueous methylcellulose. The results of these studies are shown in Table 4.

TABLE 4

Rat pharmacokinetic data.

| PK Parameters | 13 | 1a | 9b |
|---|---|---|---|
| Clearance (mL/min/kg) | 12.1 | 5.9 | 2.8 |
| $V_{ss}$ (L/kg) | 7.9 | 4.9 | 4.7 |
| $t_{1/2}$ (h) | 9.94 | 11.5 | 22.7 |
| $C_{max}$ (µM) | 0.909 | 1.31 | 1.05 |
| $AUC_{last}$ (h*µM) | 7.59 | 16.8 | 19.2 |
| % F | 86.3 | 103 | 95.9 |

Pharmacokinetics for compounds 1a, 4b, 8a, 9b, 13, 14b, 15, and 16 were determined using single dosage of male C57BL/6 mice using techniques that are well known in the art. Clearance, $V_{ss}$ and $t_{1/2}$ values were determined from an IV dose (0.3 mg/kg for compounds 1a, 4b, 13, 14b, and 16, 1 mg/kg for compound 15), formulated in 20% DMSO+60% PEG400+20% water. $C_{max}$, $AUC_{last}$ % F and brain/plasma ratio values (based on AUC) were determined from an oral dose (10 mg/kg), formulated in 0.5% aqueous methylcellulose. The results of these studies are shown in Table 5.

TABLE 5

Mouse Pharmacokinetic Data.

| PK Parameters | 1a | 4b | 8a | 9b | 13 | 14b | 15 | 16 |
|---|---|---|---|---|---|---|---|---|
| Clearance (mL/min/kg) | 4.3 | 24.5 | 7.0 | 3.9 | 14.1 | 76.7 | 12 | 4.4 |
| $V_{ss}$ (L/kg) | 4.5 | 3.30 | 3.8 | 4.8 | 4.6 | 3.72 | 4.1 | 1.8 |
| $t_{1/2}$ (h) | 12.7 | 1.86 | 6.7 | 15.9 | 3.53 | 0.70 | 5.4 | 5.2 |
| $C_{max}$ (µM) | 6.36 | 5.42 | 3.54 | 2.31 | 1.95 | 3.38 | ND | 11.9 |
| $AUC_{last}$ (h*µM) | 111 | 8.67 | 41.4 | 39.6 | 14.4 | 3.62 | ND | 70.3 |
| % F | 154 | 49.2 | 106 | 70.5 | 51 | 61.2 | ND | 92.1 |
| Brain/Plasma Ratio | 1.77 | 1.72 | 0.82 | 0.70 | 2.97 | ND | 0.24 | 0.21 |
| Free Brain/Plasma Ratio | 0.92 | 1.06 | 0.38 | 0.31 | 1.54 | ND | 0.16 | 0.16 |

The instant compounds in this invention show improved in vivo pharmacokinetics relative to compounds disclosed in WO2018207072. As shown above in Table 4, addition of a fluorine (example 1a) or a 4,4'-difluoropiperidine (example 9b) to the bicyclo[1.1.1] moiety of comparator compound 13 results in a reduced clearance and a longer half-life in rats. As shown in Table 5, addition of a fluorine (examples 1a and 4b) or a 4,4'-difluoropiperidine (example 9b) to the bicyclo[1.1.1]pentane moiety of comparator compounds 13 or 14b results in reduced clearance and a longer half-life in mice (compare 1a and 9b to 13; compare 4b to 14b). While examples 15 and 16 from WO2018207072, which possess a morpholine-substituted bicyclo[1.1.1]pentane, also show reduced clearances and longer half-lives in mouse relative to examples 13 or 14b, these examples also show reduced brain penetration relative to 13 and 14b, as well as to the comparable instant compounds in this invention 1a, 4b, 8a and 9b. (See last two rows of Table 5.)

In summary, the compounds of the claimed invention show improved microsomal stability, reduced clearance, and longer half lives compared to the compounds disclosed in WO2018207072, and also maintain acceptable levels of brain penetration.

Crystal Structures of DLK Bound to Compounds of Formula (I)

Protein Expression

Residues E115 to T402 of DLK were cloned with a C-terminal hexahistidine tag (MGS-115EDL . . . EGT402-

GNSHHHHHH, SEQ ID NO:2) into the pTriEx4 vector. Protein was expressed in *Trichoplusia ni* (*T. ni*) insect cells. *T. ni* insect cells (p30) were prepared from cultures in logarithmic phase growth and >98% viability. Cells were seeded into 4×2.5 L of ESF921 medium (containing 5 μg/ml Gentimicin) in a 5 L Optimum Growth Flask at $0.7×10^6$ cells/mL and allowed to reach cell density of $1.2×10^6$ cells overnight. The overnight cultures were counted and then infected at MOI-5 with P2-BIICs (Sf21). The infected cultures were incubated for 48 h at 27° C. on an orbital shaker at 110 rpm. The culture was harvested by centrifugation at 3,500×g, 15 min., 4° C. and stored at −80° C.

Protein Purification

Cells (e.g., 185 g wet weight corresponding to 10 L culture) were lysed in 25 mM Tris/HCl, 250 mM NaCl, 5 mM beta-mercapto-ethanol, 0.1% Triton X-100, 10% glycerol, 10 mM MgCl2, 25 mM imidazole; pH 8.0 with protease inhibitor cocktail (Roche Complete) and benzonase added according to manufacturer's recommendations. After clearance by centrifugation, the protein was subjected to IMAC using a 5 mL HisTrap crude FF column and a flow rate of 4 ml/min. After a 100 ml wash at 20 mM imidazole the highly purified protein was eluted in a gradient from 20 to 300 mM imidazole over 20 CV. The pooled protein was then subjected, at a concentration not higher than 3.5 mg/ml, to a gel filtration step using a S200 26/60pg column equilibrated in 25 mM Tris/HCl, 5% glycerol, 50 mM NaCl, 1 mM TCEP, pH 8.0. The protein was then further polished using ion exchange chromatography on a HiTrap Q HP column with the load and wash buffer being 25 mM Tris/HCl, 5% glycerol, 1 mM TCEP, pH 8.0 and the elution buffer containing 1 M of NaCl. The flow rate used was 5 ml/min and the gradient was extended over 10 CV. The final protein buffer was estimated to be 25 mM TrisHCl pH 8, 5% glycerol, 90 mM NaCl, 1 mM TCEP. The protein was concentrated using Amicon Ultra centrifugal filters with a 30 kDa MWCO to a concentration of approximately 3 mg/ml before snap freezing in small aliquots with liquid nitrogen and stored at −80° C.

Crystallization

Protein crystallized readily at 2 to 3.5 mg/ml as thin plates when mixed at equal volumes with 100 mM HEPES/NaOH pH 7.5-8.2, 200 mM magnesium acetate, 8%-16% PEG3350 (hanging drops vapour diffusion format). Crystal growth benefited from streak seeding right after drop mixing. For compound soaking trials crystals were transferred to a new drop containing 25% PEG3350, 250 mM magnesium acetate, 100 mM HEPES/NaOH pH 7.8, 15% ethylene glycol and 2 mM of compound. After incubation for 4 to 18 hrs crystals were harvested and plunge cooled in liquid nitrogen before data collection.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula (I')

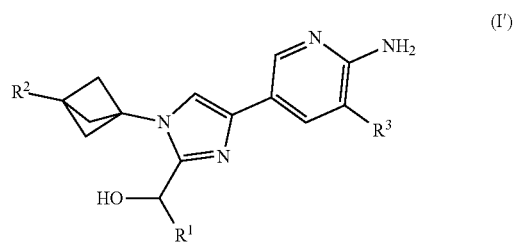

or a salt thereof wherein:

$R^1$ is chosen from alkyl and cycloalkyl, either of which is optionally substituted with one or more $R^4$;

$R^2$ is chosen from fluoro and $NR^{5a}R^{5b}$;

$R^3$ is chosen from trifluoromethyl and trifluoromethoxy;

R⁴ is halo;
R⁵ᵃ and R⁵ᵇ combine to form alkylene which, together to the intervening nitrogen, forms a monocyclic heterocycloalkyl which is optionally substituted with one or more R⁶; and
each R⁶ is independently chosen from cyano, halo, and hydroxyl
provided that R² is not a morpholine.

2. The compound of claim 1 having Formula (II):

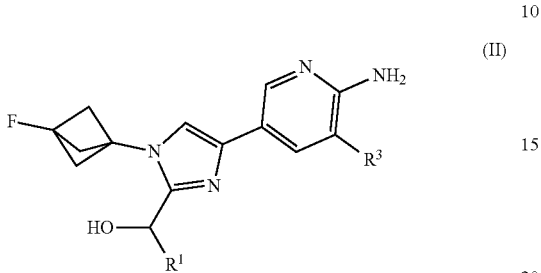

or a salt thereof wherein:
R¹ is chosen from alkyl and cycloalkyl, either of which is optionally substituted with one or more R⁴;
R³ is chosen from methoxy and trifluoromethoxy; and
R⁴ is halo.

3. The compound of claim 1 having Formula (III'):

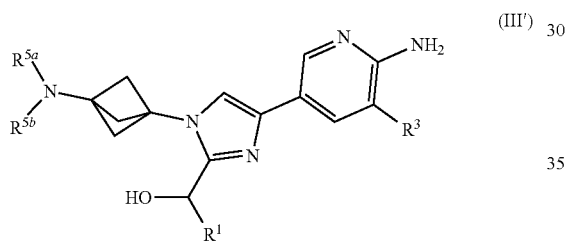

or a salt thereof wherein:
R¹ is chosen from alkyl and cycloalkyl, either of which is optionally substituted with one or more R⁴;
R³ is chosen from methoxy and trifluoromethoxy;
R⁴ is halo;
R⁵ᵃ and R⁵ᵇ combine to form alkylene which, together to the intervening nitrogen, forms a monocyclic heterocycloalkyl which is optionally substituted with one or more R⁶; and
each R⁶ is independently chosen from cyano, halo, and hydroxyl
provided R⁵ᵃ and R⁵ᵇ when combined do not form a morpholine group.

4. The compound as recited in claim 1 wherein each R⁶ is fluoro.

5. The compound as recited in claim 3, wherein the monocyclic heterocycloalkyl formed by R⁵ᵃ, R⁵ᵇ and the intervening nitrogen comprise exactly one —CF₂—.

6. The compound as recited in claim 5, wherein the monocyclic heterocycloalkyl formed by R⁵ᵃ, R⁵ᵇ and the intervening nitrogen is chosen from 3,3-difluoropiperidin-1-yl and 4,4-difluoropiperidin-1-yl.

7. The compound as recited in claim 6, wherein the monocyclic heterocycloalkyl formed by R⁵ᵃ, R⁵ᵇ and the intervening nitrogen is 4,4-difluoropiperidin-1-yl.

8. The compound as recited in claim 3, wherein R¹ is chosen from $C_{1-6}$alkyl and $C_{3-7}$cycloalkyl, either of which is optionally substituted with one, two, or three R⁴.

9. The compound as recited in claim 8, wherein each R⁴ is halo.

10. The compound as recited in claim 8, wherein R¹ is chosen from isopropyl, trifluoromethyl, and cyclopropyl.

11. The compound as recited in claim 1, wherein the compound is chosen from:

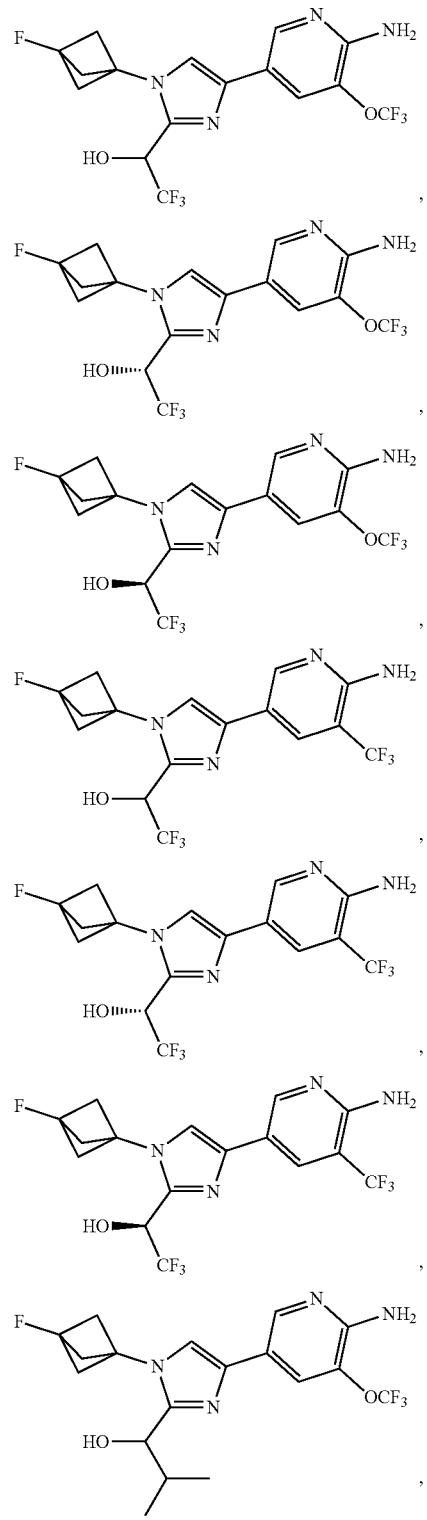

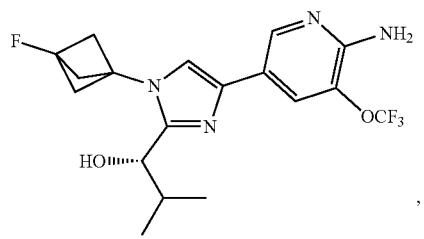
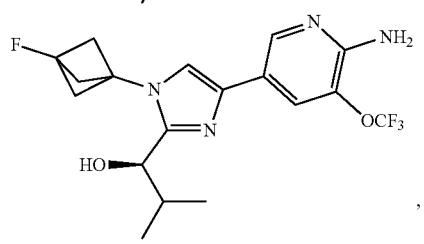
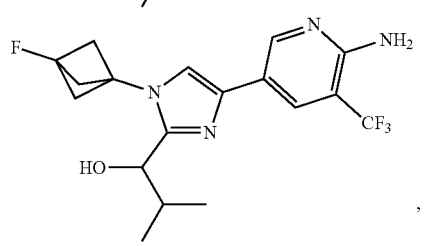
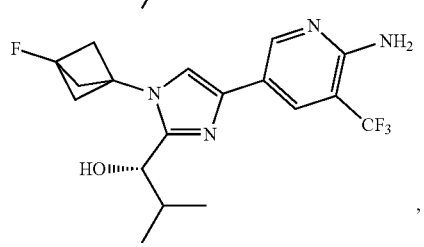
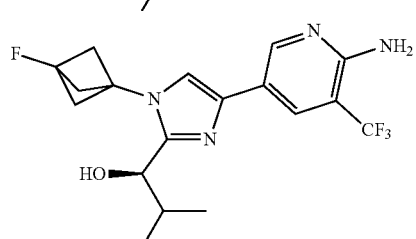
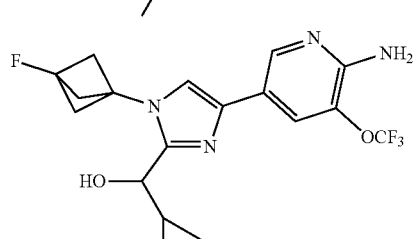
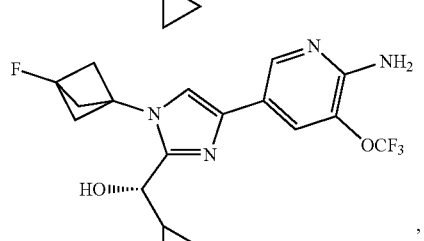
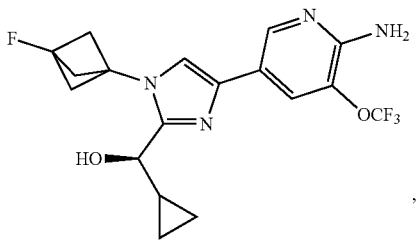
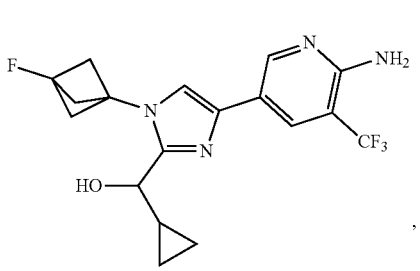
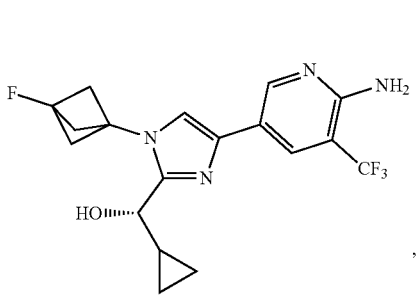
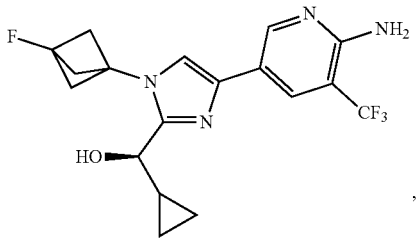
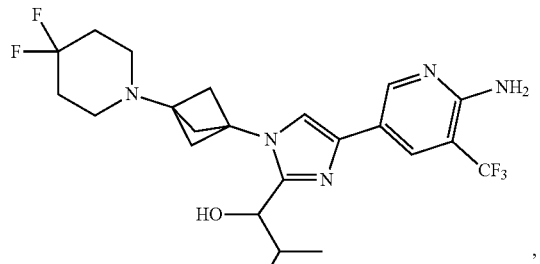
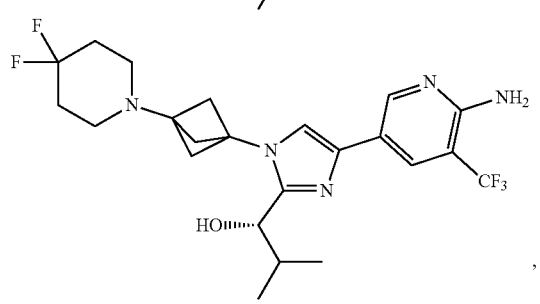

101
-continued
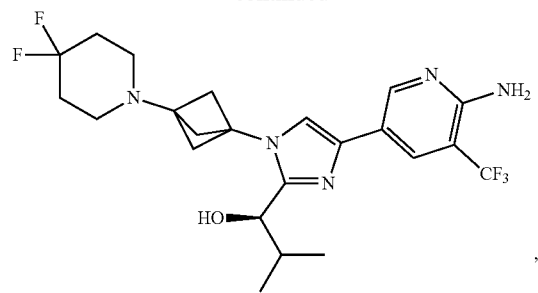
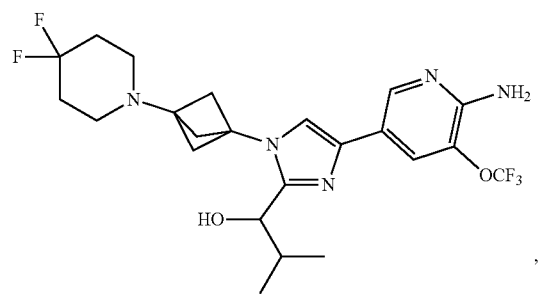
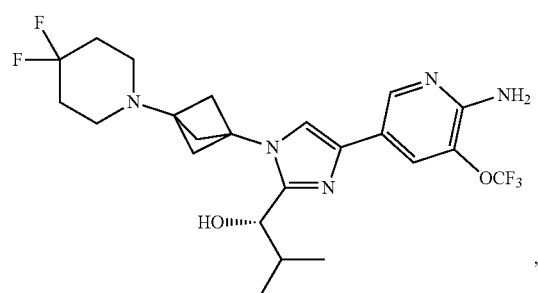
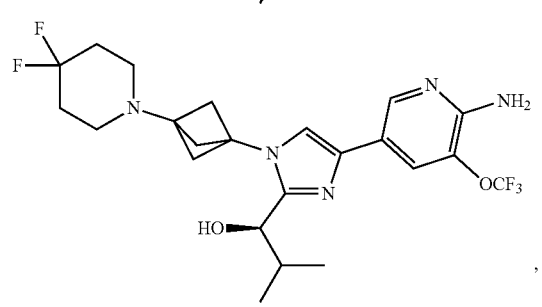
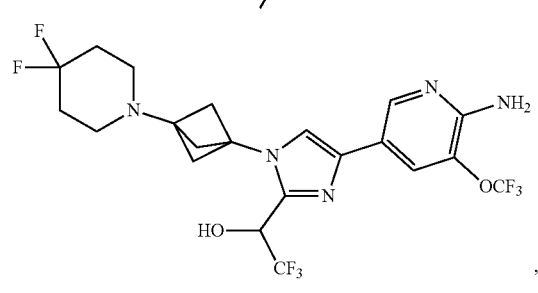
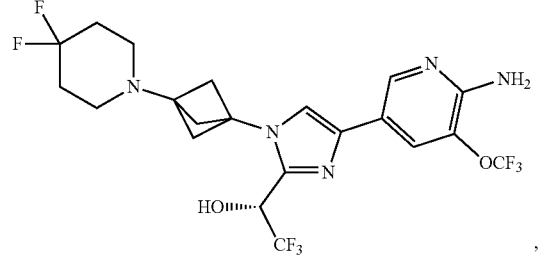
102
-continued
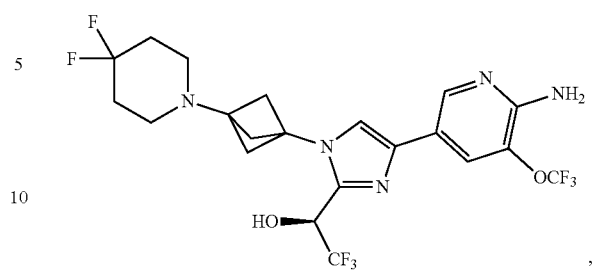
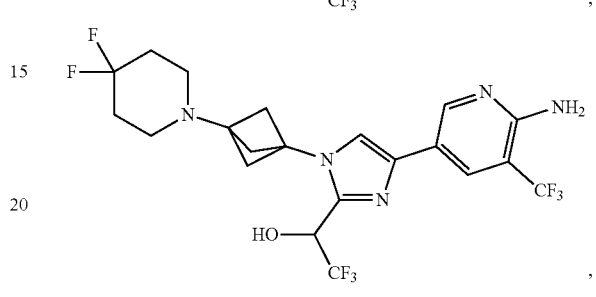
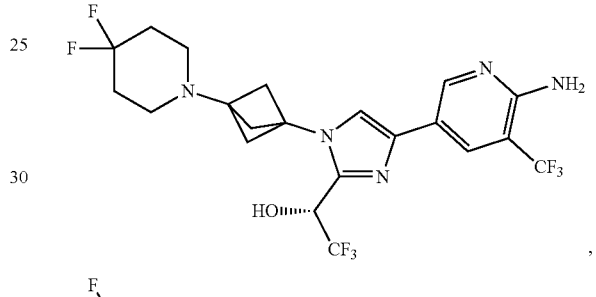
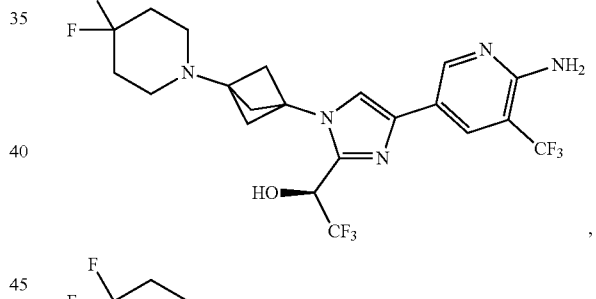
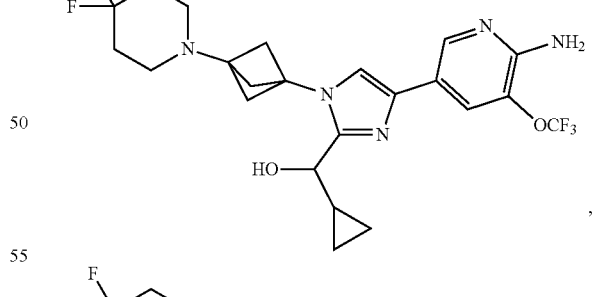
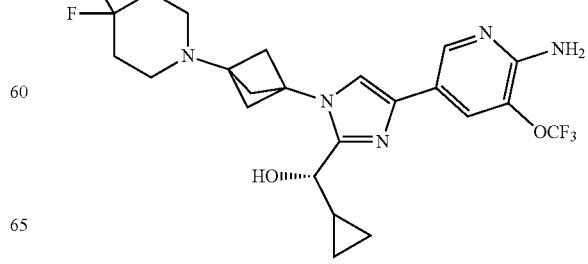

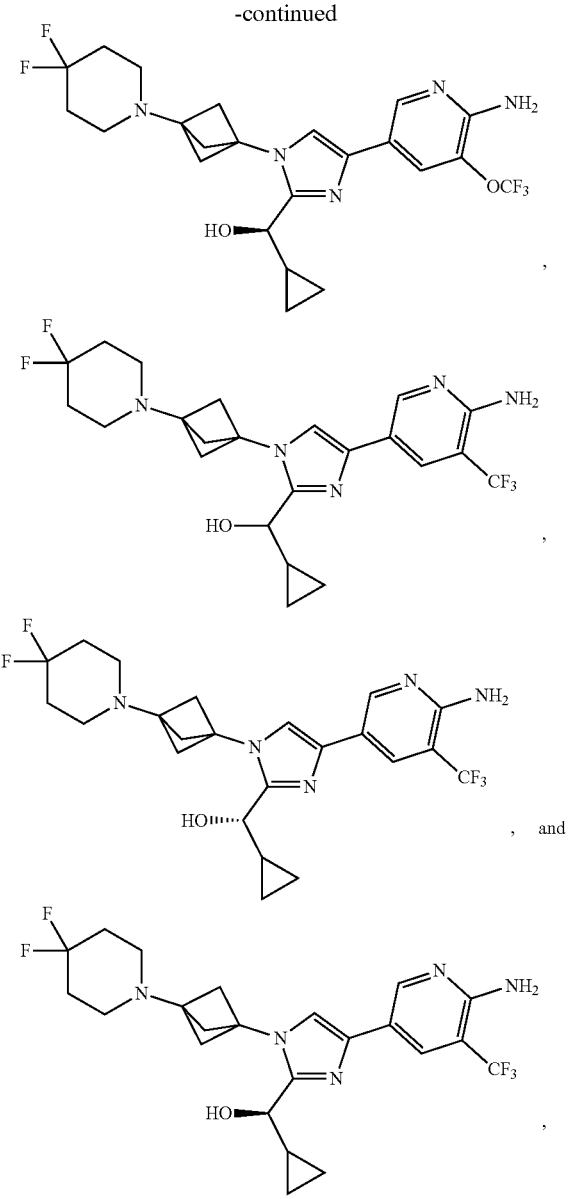

or a salt thereof.

12. A pharmaceutical composition comprising a compound as recited in claim 1, or a salt thereof, together with a pharmaceutically acceptable carrier.

13. A method of inhibition of DLK comprising contacting DLK with a compound, or a salt thereof, as recited in claim 1.

14. A method of treatment of a DLK-mediated disease comprising the administration of a therapeutically effective amount of a compound as recited claim 1, or a salt thereof, to a patient in need thereof.

15. The method as recited in claim 14 wherein said disease is a neurological disease.

16. The method as recited in claim 15 wherein said neurological disease results from traumatic injury to central nervous system or peripheral nervous system neurons.

17. The method as recited in claim 16 wherein said traumatic injury is chosen from stroke, traumatic brain injury, and spinal cord injury.

18. The method as recited in claim 15 wherein said neurological disease results from a chronic neurodegenerative condition.

19. The method as recited in claim 18 wherein said chronic neurodegenerative condition is chosen from Alzheimer's disease, frontotemporal dementia, Parkinson's disease, Huntington's disease, amyotrophic lateral sclerosis, spinocerebellar ataxia, progressive supranuclear palsy, Lewy body disease, and Kennedy's disease.

20. The method as recited in claim 15 wherein said neurological disease results from a neuropathy resulting from neurological damage.

21. The method as recited in claim 20 wherein said neurological damage is chosen from chemotherapy-induced peripheral neuropathy and diabetic neuropathy.

22. The method as recited in claim 15 wherein said disease is a cognitive disorder.

23. The method as recited in claim 22 wherein said cognitive disorder is caused by pharmacological intervention.

24. A method of treatment of a DLK-mediated disease comprising the administration of:
   a. a therapeutically effective amount of a compound as recited in claim 1, or a salt thereof; and
   b. another therapeutic agent.

* * * * *

SEQUENCE LISTING

```
<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
<223> OTHER INFORMATION: NFkB binding site

<400> SEQUENCE: 1
gggaattccc                                                          10

<210> SEQ ID NO 2
<211> LENGTH: 9
<212> TYPE: PRT
<213> ORGANISM: Artificial Sequence
<220> FEATURE:
<223> OTHER INFORMATION: C-terminal hexahistidine tag

<400> SEQUENCE: 2

Gly Asn Ser His His His His His His
1               5
```